(12) United States Patent
Bayer et al.

(10) Patent No.: US 6,225,349 B1
(45) Date of Patent: May 1, 2001

(54) HYDROXIMIC ACID HALOGENIDES, METHOD FOR THE PRODUCTION AND USE THEREOF

(75) Inventors: Herbert Bayer; Hubert Sauter, both of Mannheim; Bernd Müller, Frankenthal; Wassilios Grammenos, Ludwigshafen; Reinhard Kirstgen, Neustadt; Andreas Gypser, Mannheim; Arne Ptock, Ludwigshafen; Thomas Grote; Franz Röhl, both of Schifferstadt; Michael Rack, Heidelberg; Roland Götz, Rothenburg; Gisela Lorenz, Neustadt; Eberhard Ammermann, Heppenheim; Siegfried Strathmann, Limburgerhof; Volker Harries, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/355,278

(22) PCT Filed: Feb. 12, 1998

(86) PCT No.: PCT/EP98/00782

§ 371 Date: Jul. 28, 1999

§ 102(e) Date: Jul. 28, 1999

(87) PCT Pub. No.: WO98/38857

PCT Pub. Date: Sep. 11, 1998

(30) Foreign Application Priority Data

Mar. 5, 1997 (DE) ............................................. 197 08 940

(51) Int. Cl.[7] ......................... A01N 37/50; A01N 37/12; A01N 37/18; A01N 37/20; C07C 233/05

(52) U.S. Cl. ........................... 514/538; 514/539; 514/619; 560/35; 564/163

(58) Field of Search ................................ 560/35; 564/163; 514/538, 539, 619

(56) References Cited

FOREIGN PATENT DOCUMENTS

| 95/18789 | 7/1995 | (WO) | |
|---|---|---|---|
| WO 95/21153 | * 8/1995 | (WO) | ............................. C07C/251/34 |

* cited by examiner

Primary Examiner—Johann Richter
Assistant Examiner—Brian J. Davis
(74) Attorney, Agent, or Firm—Keil & Weinkauf

(57) ABSTRACT

Hydroximic acid halides of the formula I

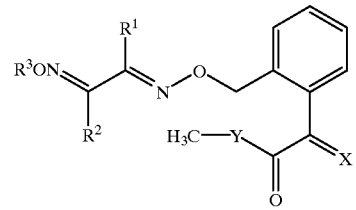

(I)

where the substituents have the following meanings:

X is $NOCH_3$, $CHOCH_3$ or $CHCH_3$;

Y is O or NH;

$R^1$ is halogen;

$R^2$ is unsubstituted or substituted alkyl, alkenyl, alkynyl, cycloalkyl or aryl;

$R^3$ is unsubstituted or substituted alkyl, alkoxyalkyl, cycloalkyl-alkyl, alkenyl and alkynyl, their salts, processes for their preparation, and their use.

12 Claims, No Drawings

HYDROXIMIC ACID HALOGENIDES, METHOD FOR THE PRODUCTION AND USE THEREOF

This application is a 371 of PCT/EP98/00782 filed Feb. 12, 1998.

TECHNICAL FIELD

The present invention relates to hydroximic acid halides of the formula I

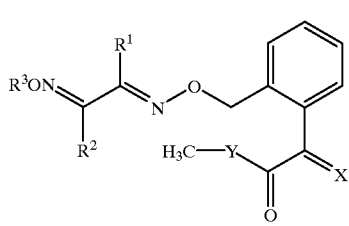

where the substituents have the following meanings:
X is $NOCH_3$, $CHOCH_3$ or $CHCH_3$;
Y is O or NH;
$R^1$ is halogen;
$R^2$ is $C_2$–$C_6$-alkyl, $C_2$–$C_6$-alkenyl and $C_2$–$C_6$-alkynyl, it being possible for these groups to be partially or fully halogenated and/or to have attached to them one or two of the following radicals: cyano, $C_1$–$C_4$-alkoxy, $C_1$–$C_4$-haloalkoxy and phenyl, it being possible for the phenyl, in turn, to be partially or fully halogenated and/or to have attached to it one to three of the following groups: cyano, nitro, $C_1$–$C_4$-alkyl, $C_1$–$C_4$-haloalkyl, $C_1$–$C_4$-alkoxy and $C_1$–$C_4$-haloalkoxy;
methyl which is partially or fully halogenated and/or has attached to it one of the following radicals: cyano, $C_1$–$C_4$-alkoxy or $C_1$–$C_4$-haloalkoxy;
$C_5$–$C_6$-cycloalkyl which can be partially or fully halogenated and/or can have attached to it one to three $C_1$–$C_4$-alkyl groups;
aryl or arylmethylene which can be partially or fully halogenated in the aryl moiety and/or can have attached to it one to three of the following radicals: cyano, nitro, $C_1$–$C_4$-alkyl, $C_1$–$C_4$-haloalkyl, $C_1$–$C_4$-alkoxy and $C_1$–$C_4$-haloalkoxy;
$R^3$ is $C_1$–$C_6$-alkyl, $C_1$–$C_3$-alkoxy-$C_1$–$C_6$-alkyl, $C_3$–$C_6$-cycloalkyl-$C_1$–$C_6$-alkyl, $C_3$–$C_6$-alkenyl and $C_3$–$C_6$-alkynyl, it being possible for these groups to be partially or fully halogenated and it being possible for the cycloalkyl groups additionally to have attached to them one to three $C_1$–$C_4$-alkyl radicals,
and to the salts thereof.

Furthermore the invention relates to processes for the preparation of the compounds I, to compositions comprising them and to their use for controlling animal pests and harmful fungi.

BACKGROUND ART

Phenylacetic acid derivatives which act against animal pests and harmful fungi and whose general structure embraces the structure of the present compounds are known from the literature (WO-A 95/21,153; WO-A 95/21,154). Moreover, WO-A 95/18,789 describes compounds of similar structures which are active against animal pests and harmful fungi.

Against this background, it was an object of the present invention to provide compounds which have improved properties regarding their action.

We have found that this object is achieved by the compounds I defined at the outset. Moreover, there have been found processes and intermediates for their preparation, compositions comprising them, and their use against animal pests and harmful fungi.

The present compounds I differ from the compounds known from WO-A 95/21,153 and WO-A 95/21,154 by the particular combination of the groups $R^1$ to $R^3$. In particular, it has been found that compounds of the known structural type have an improved activity when a halogen is bonded in the position of the radical $R^1$ and a sterically demanding group which increases the lipophilicity of the compound is bonded in the position of the radical $R^2$, and when the position of the radical $R^3$ is not taken up by hydrogen.

DISCLOSURE OF INVENTION

In general, the compounds I can be obtained by the processes described in the literature cited at the outset.

The compounds I are especially advantageously obtained by first converting a carboxylic ester IIa with hydroxylamine to give the corresponding hydroxamic acid IIc, subsequently reacting IIc with a benzyl compound IIIa to give the corresponding hydroxamic ester IV and converting IV with a halogenating agent [HAL] to give I.

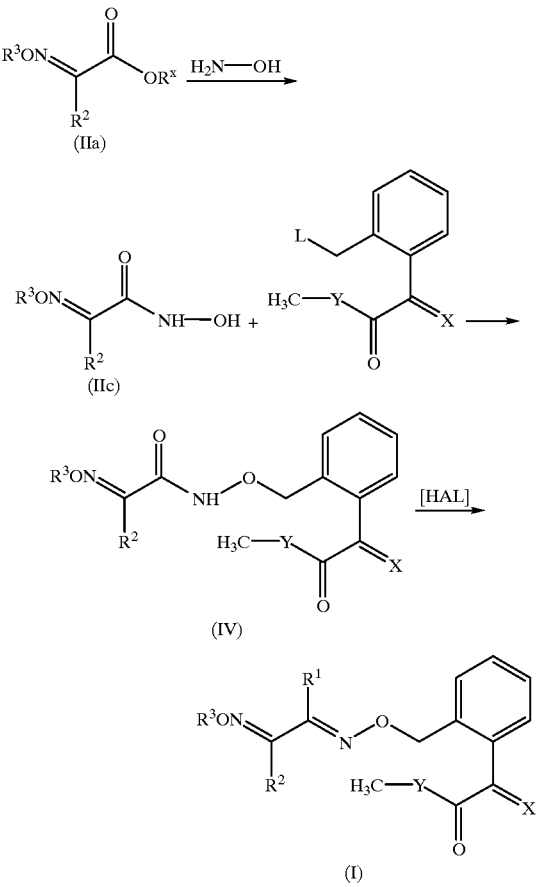

$R^x$ in formula IIa is the radical of a customary leaving group. Customary leaving groups for the purposes of the present reaction are to be understood as meaning especially the following groups: $C_1$–$C_4$-alkyl (especially methyl or ethyl) or phenyl.

L in formula IIIa is a nucleofugic leaving group. For the purposes of the present reaction, this is to be understood as meaning especially the following: halogen, alkyl sulfonate or aryl sulfonate, especially chlorine, bromine, iodine, mesylate, tosylate and triflate.

The reaction of the carboxylic ester IIa with hydroxylamine is normally carried out at from −20° C. to 50° C., preferably 0° C. to 20° C., in an inert organic solvent, preferably in the presence of a base (cf. literature: Houben-Weyl, 4th Edition, Vol. E5, p. 1141 et seq.).

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, alcohols such as methanol, ethanol, n-propanol, isopropanol, n-butanol and tert-butanol, and also dimethyl sulfoxide, dimethylformamide and dimethylacetamide, especially preferably alcohols such as methanol and ethanol. Mixtures of these may also be used.

Bases which are generally suitable are inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal carbonates and alkaline earth metal carbonates such as lithium carbonate and calcium carbonate, and also alkali metal alkoxides and alkaline earth metal alkoxides such as sodium methoxide, sodium ethoxide, potassium ethoxide, potassium tert-butoxide and dimethoxymagnesium, and furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. The following are especially preferred: alkali metal hydroxides such as sodium hydroxide and potassium hydroxide, and also alkali metal alkoxides such as sodium methoxide and sodium ethoxide.

In general, the bases are used in equimolar amounts or in an excess.

In general, the starting materials are reacted with each other in equimolar amounts. It may be advantageous for the yield to employ an excess of hydroxylamine based on IIa.

The carboxylic esters IIa required for the preparation of the compounds I which are not already known from the literature [DE-A 28 08 317; DE-A 22 65 234; J. Chem. Soc. PT 1 (1975), 2340 et seq.; Chem. Ber. 16 (1883), 2987 et seq.; J. Org. Chem. 37 (1972), 139] can be prepared in accordance with the literature cited.

The reaction of the hydroxamic acid IIc with the benzyl compound IIIa is normally carried out at from 0° C. to 130° C., preferably 10° C. to 60° C., in an inert organic solvent in the presence of a base [cf. literature: Liebigs Ann. Chem. 1992, 997 et seq.; Synth. Commun. 19, (1989), 339 et seq.].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethylformamide and dimethylacetamide, especially preferably tetrahydrofuran, acetonitrile and dimethylformamide. Mixtures of these may also be used.

Bases which are generally suitable are inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate, potassium carbonate and calcium carbonate, and also alkali metal hydrogen carbonates such as sodium hydrogen carbonate, organometallic compounds, in particular alkali metal alkyls such as methyllithium, butyl-lithium and phenyllithium, alkylmagnesium halides such as methylmagnesium chloride, alkali metal alkoxides and alkaline earth metal alkoxides such as sodium methoxide, sodium ethoxide, potassium ethoxide, potassium tert-butoxide and dimethoxymagnesium, and furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. The following are especially preferred: sodium methoxide, potassium carbonate and sodium hydride.

In general, the bases are used in equimolar amounts or in an excess or, if appropriate, as the solvent.

In general, the starting materials are reacted with each other in equimolar amounts. It may be advantageous for the yield to employ an excess of IIc based on IIIa.

Those benzyl compounds required for this reaction which are not known from the literature cited at the outset can be prepared in accordance with this literature.

The halogenation of the hydroxamic esters IV is normally carried out at from −20° C. to 100° C., preferably −10° C. to 80° C., in an inert organic solvent [cf. literature: Houben-Weyl, 4th Edition, Vol. E5, p. 631 et seq.; J. Org. Chem. 36 (1971), 233; Synthesis 9 (1991), 750 et seq.; Tetrahedron 52(1) (1996), 233 et seq.].

Halogenating agents which are suitable for this reaction are the customary inorganic and organic halogenating agents, eg. thionyl chloride, oxalyl chloride, phosphorus tribromide, phosphorus trichloride, phosphorus pentachloride, phosphorus oxychloride, phosphorus triiodide, triphenylphosphine/$CCl_4$, triphenylphosphine/$CBr_4$, triphenylphosphine/iodine, preferably thionyl chloride or the abovementioned triphenylphosphine reagents.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide, dimethylformamide and dimethylacetamide, especially preferably acetonitrile, toluene and tetrahydrofuran. Mixtures of these may also be used.

The halogenating agents are generally employed in at least equimolar amounts. It may be advantageous for the yield to employ them in an excess of up to 10 mol based on 1 mol of IV, preferably up to 5 mol, in particular up to 3 mol.

Alternatively, the compounds IV can also be obtained by reacting a carboxylic acid IIb with a benzylhydroxylamine IIIb.

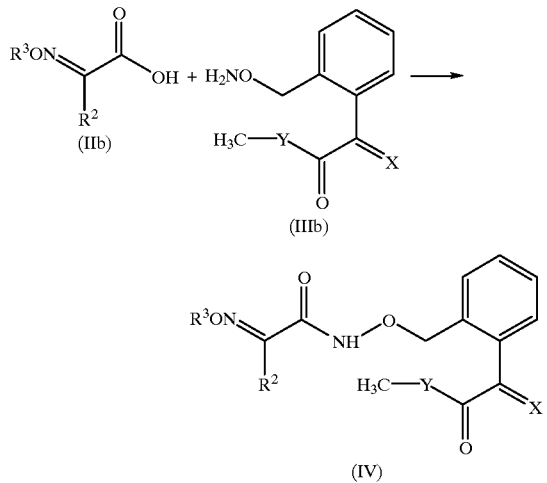

This reaction is normally carried out at from −10° C. to 120° C., preferably 0° C. to 50° C., in an inert organic solvent in the presence of an activating reagent [cf. literature: Houben-Weyl, 4th Ed. Vol. E5 p. 1141 et seq.; J. Antibiot. 39 (1986), 1382].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide, dimethylformamide and dimethylacetamide, especially preferably tetrahydrofuran and methylene chloride. Mixtures of these may also be used.

Suitable activating reagents are acid halide formers such as phosgene, phosphorus tribromide, phosphorus trichloride, phosphorus pentachloride, phosphorus oxychloride, thionyl chloride or oxalyl chloride; anhydride formers such as ethyl chloroformate or methanesulfonyl chloride; carbodiimides such as N,N'-dicyclohexylcarbodiimide or other customary agents such as N,N'-carbonyldiimidazole or triphenylphosphine in $CCl_4$. The following are especially preferred: thionyl chloride, oxalyl chloride and N,N'-carbonyldiimidazole.

In general, the activating reagents are used in equimolar amounts or in excess.

In general, the starting materials are reacted with each other in equimolar amounts. It may be advantageous for the yield to employ an excess of IIb based on IIIb.

Those carboxylic acids IIb required for this reaction which are not already known from the literature [J. Pharm. Sci. 57 (1968), 688 et seq.; DE-A 22 23 375; DE-A 22 65 234] can be prepared in accordance with the literature cited.

Moreover, the compounds IV are also obtained by reacting a carboxylic ester of the formula IIa with the benzylhydroxylamine IIIb under the conditions described above for the reaction of IIa to IIc.

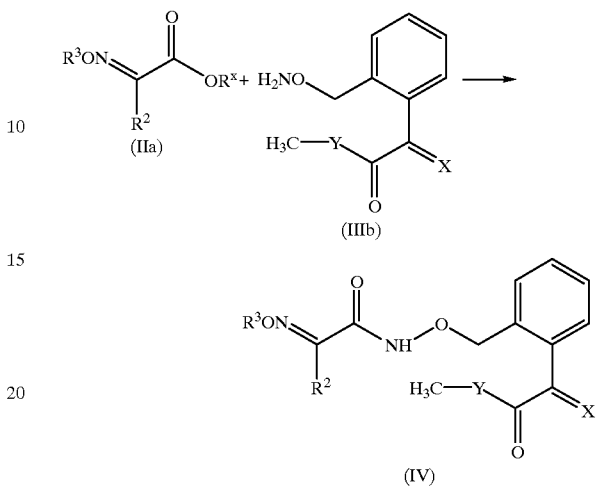

In a further process, the compounds I are advantageously obtained by converting an amidoxime IId with a benzyl compound IIIa to give the corresponding compound of the formula V and exchanging the amino group of V for halogen via a diazotization reaction.

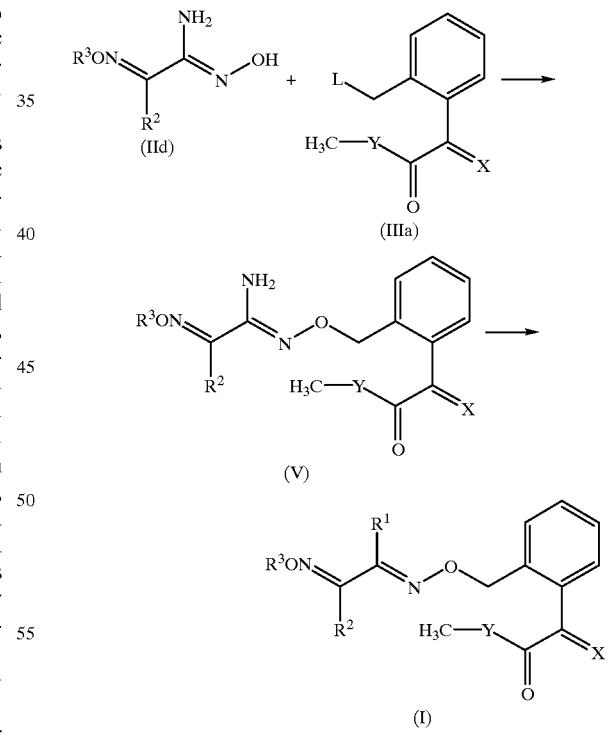

The reaction of the amidoxime IId with the benzyl compound IIIa is normally carried out at from 0° C. to 130° C., preferably 10° C. to 60° C., in an inert organic solvent in the presence of a base [cf. literature: Heterocycles 36 (1993), 1027 et seq.].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethylformamide and dimethylacetamide, especially preferably tetrahydrofuran, acetonitrile and dimethylformamide. Mixtures of these may also be used.

Bases which are generally suitable are inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate, potassium carbonate and calcium carbonate, and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride, alkali metal alkoxides and alkaline earth metal alkoxides such as sodium methoxide, sodium ethoxide, potassium ethoxide, potassium tert-butoxide and dimethoxymagnesium, and furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. The following are especially preferred: sodium methoxide, potassium carbonate and sodium hydride.

In general, the bases are used in equimolar amounts or in an excess.

In general, the starting materials are reacted with each other in equimolar amounts. It may be advantageous for the yield to employ an excess of IId based on IIIa.

The amidoximes IId required for the preparation of the compounds I which are not yet known from the literature [DE-A 44 42 732; Gazz. Chim. Ital. 55 (1925), 327] can be prepared in accordance with the literature cited.

The diazotization and halogenation of V to give I is normally carried at from −20° C. to 50° C., preferably 0° C. to 20° C., in water or in an aqueous inert organic solvent [cf. lit. J. Org. Chem. 45 (1980), 4144 et seq.; Chem. Ber. 26 (1893), 1567 et seq.].

Halogenating agents used in this reaction are hydrogen fluoride, hydrogen chloride, hydrogen bromide and hydrogen iodide, in particular hydrogen chloride.

In general, the halogenating agents are used in an excess or, if appropriate, as the solvent.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethylformamide and dimethylacetamide, especially preferably are, besides water, mixtures of dioxane and water and/or tetrahydrofuran and water.

The reaction mixtures are worked up in the customary manner, for example by mixing with water, phase separation and, if appropriate, chromatographic purification of the crude products. In some cases, the intermediates and end products are obtained in the form of colorless or pale brown viscous oils, which are purified or freed from volatile components under reduced pressure and at moderately elevated temperature. If the intermediates and end products are obtained as solids, they can also be purified by recrystallization or digestion.

Due to the C=C and C=N double bonds, the compounds I can be obtained from their preparation in the form of E/Z isomer mixtures, it being possible for these mixtures to be separated into the pure isomers in the customary manner, for example by crystallization or chromatography.

However, if the synthesis yields isomer mixtures, separation is generally not absolutely necessary since in some cases the individual isomers can be converted into each other during formulation for use or upon use (for example when exposed to light, acids or bases). Similar conversions can also take place after use, for example in the case of the treatment of plants in the treated plants or in the harmful fungus or the animal pests to be controlled.

As regards the C=X double bond, the E isomers of the compounds I are preferred with a view to their activity (configuration based on the $OCH_3$ or $CH_3$ group relative to the $COYCH_3$ group).

As regards the $CR^2=NOR^3$ double bond, the cis isomers of the compounds I are generally preferred with a view to their activity (configuration based on the radical $R^2$ relative to the $OR^3$ group).

In the definitions of the symbols given in the above formulae, collective terms were used which generally represent the following substituents:

Halogen: fluorine, chlorine, bromine and iodine;

Alkyl: saturated, straight-chain or branched hydrocarbon radicals having 1 to 4 or 6 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 4 carbon atoms (as mentioned above), it being possible for the hydrogen atoms in these groups to be partially or fully replaced by halogen atoms as mentioned above, eg. $C_1$–$C_2$-haloalkyl such as chloromethyl, bromomethyl, dichloromethyl, trichloromethyl, fluoromethyl, difluoromethyl, trifluoromethyl, chlorfluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 3 or 4 carbon atoms (as mentioned above) which are bonded to the skeleton via an oxygen atom (—O—);

Haloalkoxy: straight-chain or branched haloalkyl groups having 1 to 4 carbon atoms (as mentioned above) which are bonded to the skeleton via an oxygen atom (—O—);

Alkenyl: unsaturated, straight-chain or branched hydrocarbon radicals having 2 to 6 carbon atoms and a double bond in any position, eg. ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched hydrocarbon groups having 2 to 6 carbon atoms and a triple bond in any position, eg. ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Cycloalkyl: monocyclic, saturated hydrocarbon groups having 3 to 6 or 5 to 6 carbon ring members, eg. cyclopropyl, cyclobutyl, cyclopentyl and cyclohexyl;

Aryl: a mono- to trinuclear aromatic ring system containing 6 to 14 carbon ring members, eg. phenyl, naphthyl and anthracenyl.

The term "partially or fully halogenated" is intended to express that in groups characterized thus some or all of the hydrogen atoms of the hydrocarbon radicals can be replaced by halogen atoms as mentioned above, especially fluorine, chlorine or bromine, in particular fluorine or chlorine.

Preferred with a view to their biological activity are compounds I where Y is oxygen and X is $NOCH_3$, $CHOCH_3$ or $CHCH_3$.

Equally preferred are compounds I where Y is NH and X is $NOCH_3$.

Additionally preferred compounds I are those where $R^1$ is chlorine or bromine, in particular chlorine.

Furthermore, preferred compounds I are those where $R^2$ is one of the following groups:

$C_2$–$C_6$-alkyl which can be partially or fully halogenated and/or can have attached to it one or two of the following radicals: cyano, $C_1$–$C_4$-alkoxy, $C_1$–$C_4$-haloalkoxy and phenyl, it being possible for the phenyl, in turn, to be partially or fully halogenated and/or to have attached to it one to three of the following groups: cyano, nitro, $C_1$–$C_4$-alkyl, $C_1$–$C_4$-haloalkyl, $C_1$–$C_4$-alkoxy and $C_1$–$C_4$-haloalkoxy;

phenyl or benzyl which can be partially or fully halogenated in the aryl moiety and/or can have attached to it one to three of the following radicals: cyano, nitro, $C_1$–$C_4$-alkyl, $C_1$–$C_4$-haloalkyl, $C_1$–$C_4$-alkoxy and $C_1$–$C_4$-haloalkoxy.

In particular, preferred compounds I are those where $R^2$ is one of the following groups:

$C_2$–$C_6$-alkyl which can be partially or fully halogenated and/or can have attached to it one or two $C_1$–$C_4$-alkoxy radicals;

phenyl or benzyl, which can be partially or fully halogenated in the aryl moiety and/or can have attached to it one to three of the following radicals: cyano, $C_1$–$C_4$-alkyl, $C_1$–$C_4$-haloalkyl, $C_1$–$C_4$-alkoxy and $C_1$–$C_4$-haloalkoxy.

Furthermore preferred compounds I are those where $R^3$ is one of the following groups:

$C_1$–$C_6$-alkyl, $C_1$–$C_3$-alkoxy-$C_1$–$C_2$-alkyl, $C_3$–$C_6$-alkenyl and $C_3$–$C_6$-alkynyl, it being possible for these groups to be partially or fully halogenated.

In particular, preferred compounds I are those where $R^3$ is one of the following groups:

$C_1$–$C_6$-alkyl, $C_1$–$C_3$-alkoxy-$C_1$–$C_2$-alkyl, $C_3$–$C_6$-alkenyl and $C_3$–$C_6$-alkynyl.

Especially preferred are, in particular, compounds I where $R^3$ is $C_1$–$C_3$-alkyl, $C_1$–$C_3$-alkoxyethyl, $C_3$–$C_4$-alkenyl or $C_3$–$C_4$-alkynyl.

Compounds I which are preferred with a view to the biological activity are, in particular, those where the substituents have the following meanings:

X is $NOCH_3$, $CHOCH_3$ or $CHCH_3$;

Y is O or NH;

$R^1$ is chlorine or bromine;

$R^2$ is $C_2$–$C_6$-alkyl;

phenyl or benzyl which can be partially or fully halogenated in the phenyl moiety and/or can have attached to it one to three of the following radicals: cyano, $C_1$–$C_4$-alkyl, $C_1$–$C_4$-haloalkyl, $C_1$–$C_4$-alkoxy and $C_1$–$C_4$-haloalkoxy;

$R^3$ is $C_1$–$C_6$-alkyl, $C_3$–$C_6$-alkenyl and $C_3$–$C_6$-alkynyl, it being possible for these groups to be partially halogenated.

Especially preferred with a view to their biological activity are the compounds I compiled in the Tables which follow. In addition, the groups mentioned in the Tables for a substituent are, on their own and independently of the combination in which they are mentioned, an especially preferred embodiment of the substituent in question.

TABLE 1

Compounds of the formula I.A where $R^1$ is chlorine, $R^3$ is methyl and the radical $R^2$ for a given compound corresponds to a group of Table A

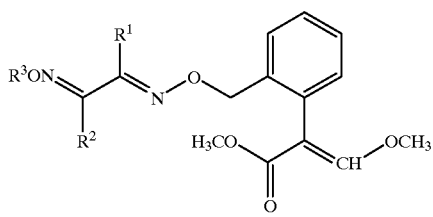

(I.A)

TABLE 2
Compounds of the formula I.B where $R^1$ is chlorine, $R^3$ is methyl and the radical $R^2$ for a given compound corresponds to a group of Table A

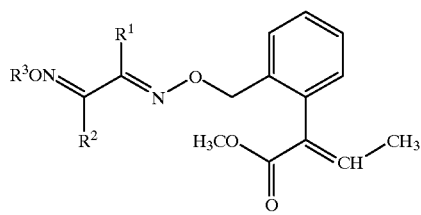

(I.B)

TABLE 3
Compounds of the formula I.C where $R^1$ is chlorine, $R^3$ is methyl and the radical $R^2$ for a given compound corresponds to a group of Table A

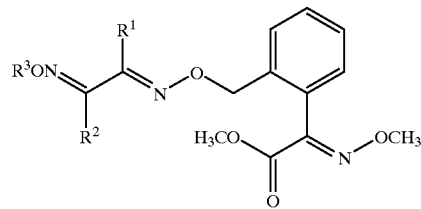

(I.C)

TABLE 4
Compounds of the formula I.D where $R^1$ is chlorine, $R^3$ is methyl and the radical $R^2$ for a given compound corresponds to a group of Table A

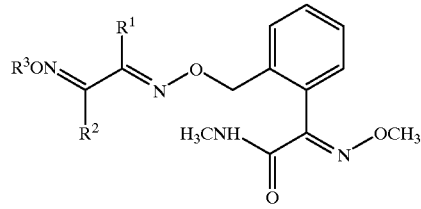

(I.D)

TABLE 5
Compounds of the formula I.A where $R^1$ is fluorine, $R^3$ is methyl and the radical $R^2$ for a given compound corresponds to a group of Table B

TABLE 6
Compounds of the formula I.B where $R^1$ is fluorine, $R^3$ is methyl and the radical $R^2$ for a given compound corresponds to a group of Table B

TABLE 7
Compounds of the formula I.C where $R^1$ is fluorine, $R^3$ is methyl and the radical $R^2$ for a given compound corresponds to a group of Table B

TABLE 8
Compounds of the formula I.D where $R^1$ is fluorine, $R^3$ is methyl and the radical $R^2$ for a given compound corresponds to a group of Table B

TABLE 9
Compounds of the formula I.A where $R^1$ is bromine, $R^3$ is methyl and the radical $R^2$ for a given compound corresponds to a group of Table A

TABLE 10
Compounds of the formula I.B where $R^1$ is bromine, $R^3$ is methyl and the radical $R^2$ for a given compound corresponds to a group of Table A

TABLE 11
Compounds of the formula I.C where $R^1$ is bromine, $R^3$ is methyl and the radical $R^2$ for a given compound corresponds to a group of Table A

TABLE 12
Compounds of the formula I.D where $R^1$ is bromine, $R^3$ is methyl and the radical $R^2$ for a given compound corresponds to a group of Table A

TABLE 13
Compounds of the formula I.A where $R^1$ is iodine, $R^3$ is methyl and the radical $R^2$ for a given compound corresponds to a group of Table B

TABLE 14
Compounds of the formula I.B where $R^1$ is iodine, $R^3$ is methyl and the radical $R^2$ for a given compound corresponds to a group of Table B

TABLE 15
Compounds of the formula I.C where $R^1$ is iodine, $R^3$ is methyl and the radical $R^2$ for a given compound corresponds to a group of Table B

TABLE 16
Compounds of the formula I.D where $R^1$ is iodine, $R^3$ is methyl and the radical $R^2$ for a given compound corresponds to a group of Table B

TABLE 17
Compounds of the formula I.A where $R^1$ is chlorine, $R^3$ is ethyl and the radical $R^2$ for a given compound corresponds to a group of Table A

TABLE 18
Compounds of the formula I.B where $R^1$ is chlorine, $R^3$ is ethyl and the radical $R^2$ for a given compound corresponds to a group of Table A

TABLE 19

Compounds of the formula I.C where $R^1$ is chlorine, $R^3$ is ethyl and the radical $R^2$ for a given compound corresponds to a group of Table A

TABLE 20

Compounds of the formula I.D where $R^1$ is chlorine, $R^3$ is ethyl and the radical $R^2$ for a given compound corresponds to a group of Table A

TABLE 21

Compounds of the formula I.A where $R^1$ is fluorine, $R^3$ is ethyl and the radical $R^2$ for a given compound corresponds to a group of Table B

TABLE 22

Compounds of the formula I.B where $R^1$ is fluorine, $R^3$ is ethyl and the radical $R^2$ for a given compound corresponds to a group of Table B

TABLE 23

Compounds of the formula I.C where $R^1$ is fluorine, $R^3$ is ethyl and the radical $R^2$ for a given compound corresponds to a group of Table B

TABLE 24

Compounds of the formula I.D where $R^1$ is fluorine, $R^3$ is ethyl and the radical $R^2$ for a given compound corresponds to a group of Table B

TABLE 25

Compounds of the formula I.A where $R^1$ is bromine, $R^3$ is ethyl and the radical $R^2$ for a given compound corresponds to a group of Table A

TABLE 26

Compounds of the formula I.B where $R^1$ is bromine, $R^3$ is ethyl and the radical $R^2$ for a given compound corresponds to a group of Table A

TABLE 27

Compounds of the formula I.C where $R^1$ is bromine, $R^3$ is ethyl and the radical $R^2$ for a given compound corresponds to a group of Table A

TABLE 28

Compounds of the formula I.D where $R^1$ is bromine, $R^3$ is ethyl and the radical $R^2$ for a given compound corresponds to a group of Table A

TABLE 29

Compounds of the formula I.A where $R^1$ is iodine, $R^3$ is ethyl and the radical $R^2$ for a given compound corresponds to a group of Table B

TABLE 30

Compounds of the formula I.B where $R^1$ is iodine, $R^3$ is ethyl and the radical $R^2$ for a given compound corresponds to a group of Table B

TABLE 31

Compounds of the formula I.C where $R^1$ is iodine, $R^3$ is ethyl and the radical $R^2$ for a given compound corresponds to a group of Table B

TABLE 32

Compounds of the formula I.D where $R^1$ is iodine, $R^3$ is ethyl and the radical $R^2$ for a given compound corresponds to a group of Table B

TABLE 33

Compounds of the formula I.A where $R^1$ is chlorine, $R^3$ is propyl and the radical $R^2$ for a given compound corresponds to a group of Table A

TABLE 34

Compounds of the formula I.B where $R^1$ is chlorine, $R^3$ is propyl and the radical $R^2$ for a given compound corresponds to a group of Table A

TABLE 35

Compounds of the formula I.C where $R^1$ is chlorine, $R^3$ is propyl and the radical $R^2$ for a given compound corresponds to a group of Table A

TABLE 36

Compounds of the formula I.D where $R^1$ is chlorine, $R^3$ is propyl and the radical $R^2$ for a given compound corresponds to a group of Table A

TABLE 37

Compounds of the formula I.A where $R^1$ is fluorine, $R^3$ is propyl and the radical $R^2$ for a given compound corresponds to a group of Table B

TABLE 38

Compounds of the formula I.B where $R^1$ is fluorine, $R^3$ is propyl and the radical $R^2$ for a given compound corresponds to a group of Table B

TABLE 39

Compounds of the formula I.C where $R^1$ is fluorine, $R^3$ is propyl and the radical $R^2$ for a given compound corresponds to a group of Table B

TABLE 40

Compounds of the formula I.D where $R^1$ is fluorine, $R^3$ is propyl and the radical $R^2$ for a given compound corresponds to a group of Table B

TABLE 41

Compounds of the formula I.A where $R^1$ is bromine, $R^3$ is propyl and the radical $R^2$ for a given compound corresponds to a group of Table A

TABLE 42

Compounds of the formula I.B where $R^1$ is bromine, $R^3$ is propyl and the radical $R^2$ for a given compound corresponds to a group of Table A

TABLE 43

Compounds of the formula I.C where $R^1$ is bromine, $R^3$ is propyl and the radical $R^2$ for a given compound corresponds to a group of Table A

TABLE 44

Compounds of the formula I.D where $R^1$ is bromine, $R^3$ is propyl and the radical $R^2$ for a given compound corresponds to a group of Table A

TABLE 45

Compounds of the formula I.A where $R^1$ is iodine, $R^3$ is propyl and the radical $R^2$ for a given compound corresponds to a group of Table B

TABLE 46

Compounds of the formula I.B where $R^1$ is iodine, $R^3$ is propyl and the radical $R^2$ for a given compound corresponds to a group of Table B

TABLE 47

Compounds of the formula I.C where $R^1$ is iodine, $R^3$ is propyl and the radical $R^2$ for a given compound corresponds to a group of Table B

TABLE 48

Compounds of the formula I.D where $R^1$ is iodine, $R^3$ is propyl and the radical $R^2$ for a given compound corresponds to a group of Table B

TABLE 49

Compounds of the formula I.A where $R^1$ is chlorine, $R^3$ is isopropyl and the radical $R^2$ for a given compound corresponds to a group of Table A

TABLE 50

Compounds of the formula I.B where $R^1$ is chlorine, $R^3$ is isopropyl and the radical $R^2$ for a given compound corresponds to a group of Table A

TABLE 51

Compounds of the formula I.C where $R^1$ is chlorine, $R^3$ is isopropyl and the radical $R^2$ for a given compound corresponds to a group of Table A

TABLE 52

Compounds of the formula I.D where $R^1$ is chlorine, $R^3$ is isopropyl and the radical $R^2$ for a given compound corresponds to a group of Table A

TABLE 53

Compounds of the formula I.A where $R^1$ is fluorine, $R^3$ is isopropyl and the radical $R^2$ for a given compound corresponds to a group of Table B

TABLE 54

Compounds of the formula I.B where $R^1$ is fluorine, $R^3$ is isopropyl and the radical $R^2$ for a given compound corresponds to a group of Table B

TABLE 55

Compounds of the formula I.C where $R^1$ is fluorine, $R^3$ is isopropyl and the radical $R^2$ for a given compound corresponds to a group of Table B

TABLE 56

Compounds of the formula I.D where $R^1$ is fluorine, $R^3$ is isopropyl and the radical $R^2$ for a given compound corresponds to a group of Table B

TABLE 57

Compounds of the formula I.A where $R^1$ is bromine, $R^3$ is isopropyl and the radical $R^2$ for a given compound corresponds to a group of Table A

TABLE 58

Compounds of the formula I.B where $R^1$ is bromine, $R^3$ is isopropyl and the radical $R^2$ for a given compound corresponds to a group of Table A

TABLE 59

Compounds of the formula I.C where $R^1$ is bromine, $R^3$ is isopropyl and the radical $R^2$ for a given compound corresponds to a group of Table A

TABLE 60

Compounds of the formula I.D where $R^1$ is bromine, $R^3$ is isopropyl and the radical $R^2$ for a given compound corresponds to a group of Table A

TABLE 61

Compounds of the formula I.A where $R^1$ is iodine, $R^3$ is isopropyl and the radical $R^2$ for a given compound corresponds to a group of Table B

TABLE 62

Compounds of the formula I.B where $R^1$ is iodine, $R^3$ is isopropyl and the radical $R^2$ for a given compound corresponds to a group of Table B

TABLE 63

Compounds of the formula I.C where $R^1$ is iodine, $R^3$ is isopropyl and the radical $R^2$ for a given compound corresponds to a group of Table B

TABLE 64

Compounds of the formula I.D where $R^1$ is iodine, $R^3$ is isopropyl and the radical $R^2$ for a given compound corresponds to a group of Table B

TABLE 65

Compounds of the formula I.A where $R^1$ is chlorine, $R^3$ is 2-methoxyethyl and the radical $R^2$ for a given compound corresponds to a group of Table A

TABLE 66

Compounds of the formula I.B where $R^1$ is chlorine, $R^3$ is 2-methoxyethyl and the radical $R^2$ for a given compound corresponds to a group of Table A

TABLE 67

Compounds of the formula I.C where $R^1$ is chlorine, $R^3$ is 2-methoxyethyl and the radical $R^2$ for a given compound corresponds to a group of Table A

TABLE 68

Compounds of the formula I.D where $R^1$ is chlorine, $R^3$ is 2-methoxyethyl and the radical $R^2$ for a given compound corresponds to a group of Table A

TABLE 69

Compounds of the formula I.A where $R^1$ is fluorine, $R^3$ is 2-methoxyethyl and the radical $R^2$ for a given compound corresponds to a group of Table B

TABLE 70

Compounds of the formula I.B where $R^1$ is fluorine, $R^3$ is 2-methoxyethyl and the radical $R^2$ for a given compound corresponds to a group of Table B

TABLE 71

Compounds of the formula I.C where $R^1$ is fluorine, $R^3$ is 2-methoxyethyl and the radical $R^2$ for a given compound corresponds to a group of Table B

TABLE 72

Compounds of the formula I.D where $R^1$ is fluorine, $R^3$ is 2-methoxyethyl and the radical $R^2$ for a given compound corresponds to a group of Table B

TABLE 73

Compounds of the formula I.A where $R^1$ is bromine, $R^3$ is 2-methoxyethyl and the radical $R^2$ for a given compound corresponds to a group of Table A

TABLE 74

Compounds of the formula I.B where $R^1$ is bromine, $R^3$ is 2-methoxyethyl and the radical $R^2$ for a given compound corresponds to a group of Table A

TABLE 75

Compounds of the formula I.C where $R^1$ is bromine, $R^3$ is 2-methoxyethyl and the radical $R^2$ for a given compound corresponds to a group of Table A

TABLE 76

Compounds of the formula I.D where $R^1$ is bromine, $R^3$ is 2-methoxyethyl and the radical $R^2$ for a given compound corresponds to a group of Table A

TABLE 77

Compounds of the formula I.A where $R^1$ is iodine, $R^3$ is 2-methoxyethyl and the radical $R^2$ for a given compound corresponds to a group of Table B

TABLE 78

Compounds of the formula I.B where $R^1$ is iodine, $R^3$ is 2-methoxyethyl and the radical $R^2$ for a given compound corresponds to a group of Table B

TABLE 79

Compounds of the formula I.C where $R^1$ is iodine, $R^3$ is 2-methoxyethyl and the radical $R^2$ for a given compound corresponds to a group of Table B

TABLE 80

Compounds of the formula I.D where $R^1$ is iodine, $R^3$ is 2-methoxyethyl and the radical $R^2$ for a given compound corresponds to a group of Table B

TABLE 81

Compounds of the formula I.A where $R^1$ is chlorine, $R^3$ is 2-ethoxyethyl and the radical $R^2$ for a given compound corresponds to a group of Table A

TABLE 82

Compounds of the formula I.B where $R^1$ is chlorine, $R^3$ is 2-ethoxyethyl and the radical $R^2$ for a given compound corresponds to a group of Table A

TABLE 83

Compounds of the formula I.C where $R^1$ is chlorine, $R^3$ is 2-ethoxyethyl and the radical $R^2$ for a given compound corresponds to a group of Table A

TABLE 84

Compounds of the formula I.D where $R^1$ is chlorine, $R^3$ is 2-ethoxyethyl and the radical $R^2$ for a given compound corresponds to a group of Table A

TABLE 85

Compounds of the formula I.A where $R^1$ is fluorine, $R^3$ is 2-ethoxyethyl and the radical $R^2$ for a given compound corresponds to a group of Table B

TABLE 86

Compounds of the formula I.B where $R^1$ is fluorine, $R^3$ is 2-ethoxyethyl and the radical $R^2$ for a given compound corresponds to a group of Table B

TABLE 87

Compounds of the formula I.C where $R^1$ is fluorine, $R^3$ is 2-ethoxyethyl and the radical $R^2$ for a given compound corresponds to a group of Table B

TABLE 88

Compounds of the formula I.D where $R^1$ is fluorine, $R^3$ is 2-ethoxyethyl and the radical $R^2$ for a given compound corresponds to a group of Table B

TABLE 89

Compounds of the formula I.A where $R^1$ is bromine, $R^3$ is 2-ethoxyethyl and the radical $R^2$ for a given compound corresponds to a group of Table A

TABLE 90

Compounds of the formula I.B where $R^1$ is bromine, $R^3$ is 2-ethoxyethyl and the radical $R^2$ for a given compound corresponds to a group of Table A

TABLE 91

Compounds of the formula I.C where $R^1$ is bromine, $R^3$ is 2-ethoxyethyl and the radical $R^2$ for a given compound corresponds to a group of Table A

TABLE 92

Compounds of the formula I.D where $R^1$ is bromine, $R^3$ is 2-ethoxyethyl and the radical $R^2$ for a given compound corresponds to a group of Table A

TABLE 93

Compounds of the formula I.A where $R^1$ is iodine, $R^3$ is 2-ethoxyethyl and the radical $R^2$ for a given compound corresponds to a group of Table B

TABLE 94

Compounds of the formula I.B where $R^1$ is iodine, $R^3$ is 2-ethoxyethyl and the radical $R^2$ for a given compound corresponds to a group of Table B

TABLE 95

Compounds of the formula I.C where $R^1$ is iodine, $R^3$ is 2-ethoxyethyl and the radical $R^2$ for a given compound corresponds to a group of Table B

TABLE 96

Compounds of the formula I.D where $R^1$ is iodine, $R^3$ is 2-ethoxyethyl and the radical $R^2$ for a given compound corresponds to a group of Table B

TABLE 97

Compounds of the formula I.A where $R^1$ is chlorine, $R^3$ is cyclopropylmethyl and the radical $R^2$ for a given compound corresponds to a group of Table A

TABLE 98

Compounds of the formula I.B where $R^1$ is chlorine, $R^3$ is cyclopropylmethyl and the radical $R^2$ for a given compound corresponds to a group of Table A

TABLE 99

Compounds of the formula I.C where $R^1$ is chlorine, $R^3$ is cyclopropylmethyl and the radical $R^2$ for a given compound corresponds to a group of Table A

TABLE 100

Compounds of the formula I.D where $R^1$ is chlorine, $R^3$ is cyclopropylmethyl and the radical $R^2$ for a given compound corresponds to a group of Table A

TABLE 101

Compounds of the formula I.A where $R^1$ is fluorine, $R^3$ is cyclopropylmethyl and the radical $R^2$ for a given compound corresponds to a group of Table B

TABLE 102

Compounds of the formula I.B where $R^1$ is fluorine, $R^3$ is cyclopropylmethyl and the radical $R^2$ for a given compound corresponds to a group of Table B

TABLE 103

Compounds of the formula I.C where $R^1$ is fluorine, $R^3$ is cyclopropylmethyl and the radical $R^2$ for a given compound corresponds to a group of Table B

TABLE 104

Compounds of the formula I.D where $R^1$ is fluorine, $R^3$ is cyclopropylmethyl and the radical $R^2$ for a given compound corresponds to a group of Table B

TABLE 105

Compounds of the formula I.A where $R^1$ is bromine, $R^3$ is cyclopropylmethyl and the radical $R^2$ for a given compound corresponds to a group of Table A

TABLE 106

Compounds of the formula I.B where $R^1$ is bromine, $R^3$ is cyclopropylmethyl and the radical $R^2$ for a given compound corresponds to a group of Table A

TABLE 107

Compounds of the formula I.C where $R^1$ is bromine, $R^3$ is cyclopropylmethyl and the radical $R^2$ for a given compound corresponds to a group of Table A

TABLE 108

Compounds of the formula I.D where $R^1$ is bromine, $R^3$ is cyclopropylmethyl and the radical $R^2$ for a given compound corresponds to a group of Table A

TABLE 109

Compounds of the formula I.A where $R^1$ is iodine, $R^3$ is cyclopropylmethyl and the radical $R^2$ for a given compound corresponds to a group of Table B

TABLE 110

Compounds of the formula I.B where $R^1$ is iodine, $R^3$ is cyclopropylmethyl and the radical $R^2$ for a given compound corresponds to a group of Table B

TABLE 111

Compounds of the formula I.C where $R^1$ is iodine, $R^3$ is cyclopropylmethyl and the radical $R^2$ for a given compound corresponds to a group of Table B

TABLE 112

Compounds of the formula I.D where $R^1$ is iodine, $R^3$ is cyclopropylmethyl and the radical $R^2$ for a given compound corresponds to a group of Table B

TABLE 113

Compounds of the formula I.A where $R^1$ is chlorine, $R^3$ is allyl and the radical $R^2$ for a given compound corresponds to a group of Table A

TABLE 114

Compounds of the formula I.B where $R^1$ is chlorine, $R^3$ is allyl and the radical $R^2$ for a given compound corresponds to a group of Table A

TABLE 115

Compounds of the formula I.C where $R^1$ is chlorine, $R^3$ is allyl and the radical $R^2$ for a given compound corresponds to a group of Table A

TABLE 116

Compounds of the formula I.D where $R^1$ is chlorine, $R^3$ is allyl and the radical $R^2$ for a given compound corresponds to a group of Table A

TABLE 117

Compounds of the formula I.A where $R^1$ is fluorine, $R^3$ is allyl and the radical $R^2$ for a given compound corresponds to a group of Table B

TABLE 118

Compounds of the formula I.B where $R^1$ is fluorine, $R^3$ is allyl and the radical $R^2$ for a given compound corresponds to a group of Table B

TABLE 119

Compounds of the formula I.C where $R^1$ is fluorine, $R^3$ is allyl and the radical $R^2$ for a given compound corresponds to a group of Table B

TABLE 120

Compounds of the formula I.D where $R^1$ is fluorine, $R^3$ is allyl and the radical $R^2$ for a given compound corresponds to a group of Table B

TABLE 121

Compounds of the formula I.A where $R^1$ is bromine, $R^3$ is allyl and the radical $R^2$ for a given compound corresponds to a group of Table A

TABLE 122

Compounds of the formula I.B where $R^1$ is bromine, $R^3$ is allyl and the radical $R^2$ for a given compound corresponds to a group of Table A

TABLE 123

Compounds of the formula I.C where $R^1$ is bromine, $R^3$ is allyl and the radical $R^2$ for a given compound corresponds to a group of Table A

TABLE 124

Compounds of the formula I.D where $R^1$ is bromine, $R^3$ is allyl and the radical $R^2$ for a given compound corresponds to a group of Table A

TABLE 125

Compounds of the formula I.A where $R^1$ is iodine, $R^3$ is allyl and the radical $R^2$ for a given compound corresponds to a group of Table B

TABLE 126

Compounds of the formula I.B where $R^1$ is iodine, $R^3$ is allyl and the radical $R^2$ for a given compound corresponds to a group of Table B

TABLE 127

Compounds of the formula I.C where $R^1$ is iodine, $R^3$ is allyl and the radical $R^2$ for a given compound corresponds to a group of Table B

TABLE 128

Compounds of the formula I.D where $R^1$ is iodine, $R^3$ is allyl and the radical $R^2$ for a given compound corresponds to a group of Table B

TABLE 129

Compounds of the formula I.A where $R^1$ is chlorine, $R^3$ is trans-3-chloroallyl and the radical $R^2$ for a given compound corresponds to a group of Table A

TABLE 130

Compounds of the formula I.B where $R^1$ is chlorine, $R^3$ is trans-3-chloroallyl and the radical $R^2$ for a given compound corresponds to a group of Table A

TABLE 131

Compounds of the formula I.C where $R^1$ is chlorine, $R^3$ is trans-3-chloroallyl and the radical $R^2$ for a given compound corresponds to a group of Table A

TABLE 132

Compounds of the formula I.D where $R^1$ is chlorine, $R^3$ is trans-3-chloroallyl and the radical $R^2$ for a given compound corresponds to a group of Table A

TABLE 133

Compounds of the formula I.A where $R^1$ is fluorine, $R^3$ is trans-3-chloroallyl and the radical $R^2$ for a given compound corresponds to a group of Table B

TABLE 134

Compounds of the formula I.B where $R^1$ is fluorine, $R^3$ is trans-3-chloroallyl and the radical $R^2$ for a given compound corresponds to a group of Table B

TABLE 135

Compounds of the formula I.C where $R^1$ is fluorine, $R^3$ is trans-3-chloroallyl and the radical $R^2$ for a given compound corresponds to a group of Table B

TABLE 136

Compounds of the formula I.D where $R^1$ is fluorine, $R^3$ is trans-3-chloroallyl and the radical $R^2$ for a given compound corresponds to a group of Table B

TABLE 137

Compounds of the formula I.A where $R^1$ is bromine, $R^3$ is trans-3-chloroallyl and the radical $R^2$ for a given compound corresponds to a group of Table A

TABLE 138

Compounds of the formula I.B where $R^1$ is bromine, $R^3$ is trans-3-chloroallyl and the radical $R^2$ for a given compound corresponds to a group of Table A

TABLE 139

Compounds of the formula I.C where $R^1$ is bromine, $R^3$ is trans-3-chloroallyl and the radical $R^2$ for a given compound corresponds to a group of Table A

TABLE 140

Compounds of the formula I.D where $R^1$ is bromine, $R^3$ is trans-3-chloroallyl and the radical $R^2$ for a given compound corresponds to a group of Table A

TABLE 141

Compounds of the formula I.A where $R^1$ is iodine, $R^3$ is trans-3-chloroallyl and the radical $R^2$ for a given compound corresponds to a group of Table B

TABLE 142

Compounds of the formula I.B where $R^1$ is iodine, $R^3$ is trans-3-chloroallyl and the radical $R^2$ for a given compound corresponds to a group of Table B

TABLE 143

Compounds of the formula I.C where $R^1$ is iodine, $R^3$ is trans-3-chloroallyl and the radical $R^2$ for a given compound corresponds to a group of Table B

TABLE 144

Compounds of the formula I.D where $R^1$ is iodine, $R^3$ is trans-3-chloroallyl and the radical $R^2$ for a given compound corresponds to a group of Table B

TABLE 145

Compounds of the formula I.A where $R^1$ is chlorine, $R^3$ is trans-butenyl and the radical $R^2$ for a given compound corresponds to a group of Table A

TABLE 146

Compounds of the formula I.B where $R^1$ is chlorine, $R^3$ is trans-butenyl and the radical $R^2$ for a given compound corresponds to a group of Table A

TABLE 147

Compounds of the formula I.C where $R^1$ is chlorine, $R^3$ is trans-butenyl and the radical $R^2$ for a given compound corresponds to a group of Table A

TABLE 148

Compounds of the formula I.D where $R^1$ is chlorine, $R^3$ is trans-butenyl and the radical $R^2$ for a given compound corresponds to a group of Table A

TABLE 149
Compounds of the formula I.A where $R^1$ is fluorine, $R^3$ is trans-butenyl and the radical $R^2$ for a given compound corresponds to a group of Table B

TABLE 150
Compounds of the formula I.B where $R^1$ is fluorine, $R^3$ is trans-butenyl and the radical $R^2$ for a given compound corresponds to a group of Table B

TABLE 151
Compounds of the formula I.C where $R^1$ is fluorine, $R^3$ is trans-butenyl and the radical $R^2$ for a given compound corresponds to a group of Table B

TABLE 152
Compounds of the formula I.D where $R^1$ is fluorine, $R^3$ is trans-butenyl and the radical $R^2$ for a given compound corresponds to a group of Table B

TABLE 153
Compounds of the formula I.A where $R^1$ is bromine, $R^3$ is trans-butenyl and the radical $R^2$ for a given compound corresponds to a group of Table A

TABLE 154
Compounds of the formula I.B where $R^1$ is bromine, $R^3$ is trans-butenyl and the radical $R^2$ for a given compound corresponds to a group of Table A

TABLE 155
Compounds of the formula I.C where $R^1$ is bromine, $R^3$ is trans-butenyl and the radical $R^2$ for a given compound corresponds to a group of Table A

TABLE 156
Compounds of the formula I.D where $R^1$ is bromine, $R^3$ is trans-butenyl and the radical $R^2$ for a given compound corresponds to a group of Table A

TABLE 157
Compounds of the formula I.A where $R^1$ is iodine, $R^3$ is trans-butenyl and the radical $R^2$ for a given compound corresponds to a group of Table A

TABLE 158
Compounds of the formula I.B where $R^1$ is iodine, $R^3$ is trans-butenyl and the radical $R^2$ for a given compound corresponds to a group of Table B

TABLE 159
Compounds of the formula I.C where $R^1$ is iodine, $R^3$ is trans-butenyl and the radical $R^2$ for a given compound corresponds to a group of Table B

TABLE 160
Compounds of the formula I.D where $R^1$ is iodine, $R^3$ is trans-butenyl and the radical $R^2$ for a given compound corresponds to a group of Table B

TABLE 161
Compounds of the formula I.A where $R^1$ is chlorine, $R^3$ is propargyl and the radical $R^2$ for a given compound corresponds to a group of Table A

TABLE 162
Compounds of the formula I.B where $R^1$ is chlorine, $R^3$ is propargyl and the radical $R^2$ for a given compound corresponds to a group of Table A

TABLE 163
Compounds of the formula I.C where $R^1$ is chlorine, $R^3$ is propargyl and the radical $R^2$ for a given compound corresponds to a group of Table A

TABLE 164
Compounds of the formula I.D where $R^1$ is chlorine, $R^3$ is propargyl and the radical $R^2$ for a given compound corresponds to a group of Table A

TABLE 165
Compounds of the formula I.A where $R^1$ is fluorine, $R^3$ is propargyl and the radical $R^2$ for a given compound corresponds to a group of Table B

TABLE 166
Compounds of the formula I.B where $R^1$ is fluorine, $R^3$ is propargyl and the radical $R^2$ for a given compound corresponds to a group of Table B

TABLE 167
Compounds of the formula I.C where $R^1$ is fluorine, $R^3$ is propargyl and the radical $R^2$ for a given compound corresponds to a group of Table B

TABLE 168
Compounds of the formula I.D where $R^1$ is fluorine, $R^3$ is propargyl and the radical $R^2$ for a given compound corresponds to a group of Table B

TABLE 169
Compounds of the formula I.A where $R^1$ is bromine, $R^3$ is propargyl and the radical $R^2$ for a given compound corresponds to a group of Table A

TABLE 170
Compounds of the formula I.B where $R^1$ is bromine, $R^3$ is propargyl and the radical $R^2$ for a given compound corresponds to a group of Table A

TABLE 171
Compounds of the formula I.C where $R^1$ is bromine, $R^3$ is propargyl and the radical $R^2$ for a given compound corresponds to a group of Table A

TABLE 172
Compounds of the formula I.D where $R^1$ is bromine, $R^3$ is propargyl and the radical $R^2$ for a given compound corresponds to a group of Table A

TABLE 173
Compounds of the formula I.A where $R^1$ is iodine, $R^3$ is propargyl and the radical $R^2$ for a given compound corresponds to a group of Table B

TABLE 174
Compounds of the formula I.B where $R^1$ is iodine, $R^3$ is propargyl and the radical $R^2$ for a given compound corresponds to a group of Table B

TABLE 175

Compounds of the formula I.C where $R^1$ is iodine, $R^3$ is propargyl and the radical $R^2$ for a given compound corresponds to a group of Table B

TABLE 176

Compounds of the formula I.D where $R^1$ is iodine, $R^3$ is propargyl and the radical $R^2$ for a given compound corresponds to a group of Table B

TABLE 177

Compounds of the formula I.A where $R^1$ is chlorine, $R^3$ is 3-bromopropargyl and the radical $R^2$ for a given compound corresponds to a group of Table A

TABLE 178

Compounds of the formula I.B where $R^1$ is chlorine, $R^3$ is 3-bromopropargyl and the radical $R^2$ for a given compound corresponds to a group of Table A

TABLE 179

Compounds of the formula I.C where $R^1$ is chlorine, $R^3$ is 3-bromopropargyl and the radical $R^2$ for a given compound corresponds to a group of Table A

TABLE 180

Compounds of the formula I.D where $R^1$ is chlorine, $R^3$ is 3-bromopropargyl and the radical $R^2$ for a given compound corresponds to a group of Table A

TABLE 181

Compounds of the formula I.A where $R^1$ is fluorine, $R^3$ is 3-bromopropargyl and the radical $R^2$ for a given compound corresponds to a group of Table B

TABLE 182

Compounds of the formula I.B where $R^1$ is fluorine, $R^3$ is 3-bromopropargyl and the radical $R^2$ for a given compound corresponds to a group of Table B

TABLE 183

Compounds of the formula I.C where $R^1$ is fluorine, $R^3$ is 3-bromopropargyl and the radical $R^2$ for a given compound corresponds to a group of Table B

TABLE 184

Compounds of the formula I.D where $R^1$ is fluorine, $R^3$ is 3-bromopropargyl and the radical $R^2$ for a given compound corresponds to a group of Table B

TABLE 185

Compounds of the formula I.A where $R^1$ is bromine, $R^3$ is 3-bromopropargyl and the radical $R^2$ for a given compound corresponds to a group of Table A

TABLE 186

Compounds of the formula I.B where $R^1$ is bromine, $R^3$ is 3-bromopropargyl and the radical $R^2$ for a given compound corresponds to a group of Table A

TABLE 187

Compounds of the formula I.C where $R^1$ is bromine, $R^3$ is 3-bromopropargyl and the radical $R^2$ for a given compound corresponds to a group of Table A

TABLE 188

Compounds of the formula I.D where $R^1$ is bromine, $R^3$ is 3-bromopropargyl and the radical $R^2$ for a given compound corresponds to a group of Table A

TABLE 189

Compounds of the formula I.A where $R^1$ is iodine, $R^3$ is 3-bromopropargyl and the radical $R^2$ for a given compound corresponds to a group of Table B

TABLE 190

Compounds of the formula I.B where $R^1$ is iodine, $R^3$ is 3-bromopropargyl and the radical $R^2$ for a given compound corresponds to a group of Table B

TABLE 191

Compounds of the formula I.C where $R^1$ is iodine, $R^3$ is 3-bromopropargyl and the radical $R^2$ for a given compound corresponds to a group of Table B

TABLE 192

Compounds of the formula I.D where $R^1$ is iodine, $R^3$ is 3-bromopropargyl and the radical $R^2$ for a given compound corresponds to a group of Table B

TABLE 193

Compounds of the formula I.A where $R^1$ is chlorine, $R^3$ is but-3-yn-1-yl and the radical $R^2$ for a given compound corresponds to a group of Table A

TABLE 194

Compounds of the formula I.B where $R^1$ is chlorine, $R^3$ is but-3-yn-1-yl and the radical $R^2$ for a given compound corresponds to a group of Table A

TABLE 195

Compounds of the formula I.C where $R^1$ is chlorine, $R^3$ is but-3-yn-1-yl and the radical $R^2$ for a given compound corresponds to a group of Table A

TABLE 196

Compounds of the formula I.D where $R^1$ is chlorine, $R^3$ is but-3-yn-1-yl and the radical $R^2$ for a given compound corresponds to a group of Table A

TABLE 197

Compounds of the formula I.A where $R^1$ is fluorine, $R^3$ is but-3-yn-1-yl and the radical $R^2$ for a given compound corresponds to a group of Table B

TABLE 198

Compounds of the formula I.B where $R^1$ is fluorine, $R^3$ is but-3-yn-1-yl and the radical $R^2$ for a given compound corresponds to a group of Table B

TABLE 199

Compounds of the formula I.C where $R^1$ is fluorine, $R^3$ is but-3-yn-1-yl and the radical $R^2$ for a given compound corresponds to a group of Table B

TABLE 200

Compounds of the formula I.D where $R^1$ is fluorine, $R^3$ is but-3-yn-1-yl and the radical $R^2$ for a given compound corresponds to a group of Table B

TABLE 201
Compounds of the formula I.A where $R^1$ is bromine, $R^3$ is but-3-yn-1-yl and the radical $R^2$ for a given compound corresponds to a group of Table A

TABLE 202
Compounds of the formula I.B where $R^1$ is bromine, $R^3$ is but-3-yn-1-yl and the radical $R^2$ for a given compound corresponds to a group of Table A

TABLE 203
Compounds of the formula I.C where $R^1$ is bromine, $R^3$ is but-3-yn-1-yl and the radical $R^2$ for a given compound corresponds to a group of Table A

TABLE 204
Compounds of the formula I.D where $R^1$ is bromine, $R^3$ is but-3-yn-1-yl and the radical $R^2$ for a given compound corresponds to a group of Table A

TABLE 205
Compounds of the formula I.A where $R^1$ is iodine, $R^3$ is but-3-yn-1-yl and the radical $R^2$ for a given compound corresponds to a group of Table B

TABLE 206
Compounds of the formula I.B where $R^1$ is iodine, $R^3$ is but-3-yn-1-yl and the radical $R^2$ for a given compound corresponds to a group of Table B

TABLE 207
Compounds of the formula I.C where $R^1$ is iodine, $R^3$ is but-3-yn-1-yl and the radical $R^2$ for a given compound corresponds to a group of Table B

TABLE 208
Compounds of the formula I.D where $R^1$ is iodine, $R^3$ is but-3-yn-1-yl and the radical $R^2$ for a given compound corresponds to a group of Table B

TABLE 209
Compounds of the formula I.A where $R^1$ is chlorine, $R^3$ is fluoromethyl and the radical $R^2$ for a given compound corresponds to a group of Table A

TABLE 210
Compounds of the formula I.B where $R^1$ is chlorine, $R^3$ is fluoromethyl and the radical $R^2$ for a given compound corresponds to a group of Table A

TABLE 211
Compounds of the formula I.C where $R^1$ is chlorine, $R^3$ is fluoromethyl and the radical $R^2$ for a given compound corresponds to a group of Table A

TABLE 212
Compounds of the formula I.D where $R^1$ is chlorine, $R^3$ is fluoromethyl and the radical $R^2$ for a given compound corresponds to a group of Table A

TABLE 213
Compounds of the formula I.A where $R^1$ is fluorine, $R^3$ is fluoromethyl and the radical $R^2$ for a given compound corresponds to a group of Table B

TABLE 214
Compounds of the formula I.B where $R^1$ is fluorine, $R^3$ is fluoromethyl and the radical $R^2$ for a given compound corresponds to a group of Table B

TABLE 215
Compounds of the formula I.C where $R^1$ is fluorine, $R^3$ is fluoromethyl and the radical $R^2$ for a given compound corresponds to a group of Table B

TABLE 216
Compounds of the formula I.D where $R^1$ is fluorine, $R^3$ is fluoromethyl and the radical $R^2$ for a given compound corresponds to a group of Table B

TABLE 217
Compounds of the formula I.A where $R^1$ is bromine, $R^3$ is fluoromethyl and the radical $R^2$ for a given compound corresponds to a group of Table A

TABLE 218
Compounds of the formula I.B where $R^1$ is bromine, $R^3$ is fluoromethyl and the radical $R^2$ for a given compound corresponds to a group of Table A

TABLE 219
Compounds of the formula I.C where $R^1$ is bromine, $R^3$ is fluoromethyl and the radical $R^2$ for a given compound corresponds to a group of Table A

TABLE 220
Compounds of the formula I.D where $R^1$ is bromine, $R^3$ is fluoromethyl and the radical $R^2$ for a given compound corresponds to a group of Table A

TABLE 221
Compounds of the formula I.A where $R^1$ is iodine, $R^3$ is fluoromethyl and the radical $R^2$ for a given compound corresponds to a group of Table B

TABLE 222
Compounds of the formula I.B where $R^1$ is iodine, $R^3$ is fluoromethyl and the radical $R^2$ for a given compound corresponds to a group of Table B

TABLE 223
Compounds of the formula I.C where $R^1$ is iodine, $R^3$ is fluoromethyl and the radical $R^2$ for a given compound corresponds to a group of Table B

TABLE 224
Compounds of the formula I.D where $R^1$ is iodine, $R^3$ is fluoromethyl and the radical $R^2$ for a given compound corresponds to a group of Table B

TABLE 225
Compounds of the formula I.A where $R^1$ is chlorine, $R^3$ is difluoromethyl and the radical $R^2$ for a given compound corresponds to a group of Table A

TABLE 226
Compounds of the formula I.B where $R^1$ is chlorine, $R^3$ is difluoromethyl and the radical $R^2$ for a given compound corresponds to a group of Table A

TABLE 227
Compounds of the formula I.C where $R^1$ is chlorine, $R^3$ is difluoromethyl and the radical $R^2$ for a given compound corresponds to a group of Table A

TABLE 228
Compounds of the formula I.D where $R^1$ is chlorine, $R^3$ is difluoromethyl and the radical $R^2$ for a given compound corresponds to a group of Table A

TABLE 229
Compounds of the formula I.A where $R^1$ is fluorine, $R^3$ is difluoromethyl and the radical $R^2$ for a given compound corresponds to a group of Table B

TABLE 230
Compounds of the formula I.B where $R^1$ is fluorine, $R^3$ is difluoromethyl and the radical $R^2$ for a given compound corresponds to a group of Table B

TABLE 231
Compounds of the formula I.C where $R^1$ is fluorine, $R^3$ is difluoromethyl and the radical $R^2$ for a given compound corresponds to a group of Table B

TABLE 232
Compounds of the formula I.D where $R^1$ is fluorine, $R^3$ is difluoromethyl and the radical $R^2$ for a given compound corresponds to a group of Table B

TABLE 233
Compounds of the formula I.A where $R^1$ is bromine, $R^3$ is difluoromethyl and the radical $R^2$ for a given compound corresponds to a group of Table A

TABLE 234
Compounds of the formula I.B where $R^1$ is bromine, $R^3$ is difluoromethyl and the radical $R^2$ for a given compound corresponds to a group of Table A

TABLE 235
Compounds of the formula I.C where $R^1$ is bromine, $R^3$ is difluoromethyl and the radical $R^2$ for a given compound corresponds to a group of Table A

TABLE 236
Compounds of the formula I.D where $R^1$ is bromine, $R^3$ is difluoromethyl and the radical $R^2$ for a given compound corresponds to a group of Table A

TABLE 237
Compounds of the formula I.A where $R^1$ is iodine, $R^3$ is difluoromethyl and the radical $R^2$ for a given compound corresponds to a group of Table B

TABLE 238
Compounds of the formula I.B where $R^1$ is iodine, $R^3$ is difluoromethyl and the radical $R^2$ for a given compound corresponds to a group of Table B

TABLE 239
Compounds of the formula I.C where $R^1$ is iodine, $R^3$ is difluoromethyl and the radical $R^2$ for a given compound corresponds to a group of Table B

TABLE 240
Compounds of the formula I.D where $R^1$ is iodine, $R^3$ is difluoromethyl and the radical $R^2$ for a given compound corresponds to a group of Table B

TABLE 241
Compounds of the formula I.A where $R^1$ is chlorine, $R^3$ is 2,2,2-trifluoroethyl and the radical $R^2$ for a given compound corresponds to a group of Table A

TABLE 242
Compounds of the formula I.B where $R^1$ is chlorine, $R^3$ is 2,2,2-trifluoroethyl and the radical $R^2$ for a given compound corresponds to a group of Table A

TABLE 243
Compounds of the formula I.C where $R^1$ is chlorine, $R^3$ is 2,2,2-trifluoroethyl and the radical $R^2$ for a given compound corresponds to a group of Table A

TABLE 244
Compounds of the formula I.D where $R^1$ is chlorine, $R^3$ is 2,2,2-trifluoroethyl and the radical $R^2$ for a given compound corresponds to a group of Table A

TABLE 245
Compounds of the formula I.A where $R^1$ is fluorine, $R^3$ is 2,2,2-trifluoroethyl and the radical $R^2$ for a given compound corresponds to a group of Table B

TABLE 246
Compounds of the formula I.B where $R^1$ is fluorine, $R^3$ is 2,2,2-trifluoroethyl and the radical $R^2$ for a given compound corresponds to a group of Table B

TABLE 247
Compounds of the formula I.C where $R^1$ is fluorine, $R^3$ is 2,2,2-trifluoroethyl and the radical $R^2$ for a given compound corresponds to a group of Table B

TABLE 248
Compounds of the formula I.D where $R^1$ is fluorine, $R^3$ is 2,2,2-trifluoroethyl and the radical $R^2$ for a given compound corresponds to a group of Table B

TABLE 249
Compounds of the formula I.A where $R^1$ is bromine, $R^3$ is 2,2,2-trifluoroethyl and the radical $R^2$ for a given compound corresponds to a group of Table A

TABLE 250
Compounds of the formula I.B where $R^1$ is bromine, $R^3$ is 2,2,2-trifluoroethyl and the radical $R^2$ for a given compound corresponds to a group of Table A

TABLE 251
Compounds of the formula I.C where $R^1$ is bromine, $R^3$ is 2,2,2-trifluoroethyl and the radical $R^2$ for a given compound corresponds to a group of Table A

TABLE 252
Compounds of the formula I.D where $R^1$ is bromine, $R^3$ is 2,2,2-trifluoroethyl and the radical $R^2$ for a given compound corresponds to a group of Table A

TABLE 253

Compounds of the formula I.A where $R^1$ is iodine, $R^3$ is 2,2,2-trifluoroethyl and the radical $R^2$ for a given compound corresponds to a group of Table B

TABLE 254

Compounds of the formula I.B where $R^1$ is iodine, $R^3$ is 2,2,2-trifluoroethyl and the radical $R^2$ for a given compound corresponds to a group of Table B

TABLE 255

Compounds of the formula I.C where $R^1$ is iodine, $R^3$ is 2,2,2-trifluoroethyl and the radical $R^2$ for a given compound corresponds to a group of Table B

TABLE 256

Compounds of the formula I.D where $R^1$ is iodine, $R^3$ is 2,2,2-trifluoroethyl and the radical $R^2$ for a given compound corresponds to a group of Table B

TABLE A

| No. | $R^2$ | |
|---|---|---|
| A.1 | $CH_2CH_3$ | |
| A.2 | $CH_2CH_2$—CN | |
| A.3 | $CH_2CH_2$—O—$CH_3$ | |
| A.4 | $CH_2CH_2$—O—$CH_2CH_3$ | |
| A.5 | $CH_2CH_2CH_3$ | |
| A.6 | $CH(CH_3)_2$ | |
| A.7 | $CH_2CH_2CH_2CH_3$ | |
| A.8 | $CH(CH_3)CH_2CH_3$ | |
| A.9 | $CH_2CH(CH_3)_2$ | |
| A.10 | CH=$CH_2$ | |
| A.11 | CH=CH-$CH_3$ | (E) |
| A.12 | CH=CH—[$C_6H_5$] | (E) |
| A.13 | CH=CH—[2-CN—$C_6H_4$] | (E) |
| A.14 | CH=CH—[3-CN—$C_6H_4$] | (E) |
| A.15 | CH=CH—[4-CN—$C_6H_4$] | (E) |
| A.16 | CH=CH—[2-F—$C_6H_4$] | (E) |
| A.17 | CH=CH—[3-F—$C_6H_4$] | (E) |
| A.18 | CH=CH—[4-F—$C_6H_4$] | (E) |
| A.19 | CH=CH—[2,4-$F_2$—$C_6H_3$] | (E) |
| A.20 | CH=CH—[3,4-$F_2$—$C_6H_3$] | (E) |
| A.21 | CH=CH—[2,4,5-$F_3$—$C_6H_2$] | (E) |
| A.22 | CH=CH—[2,4,6-$F_3$—$C_6H_2$] | (E) |
| A.23 | CH=CH—[2-Cl—$C_6H_4$] | (E) |
| A.24 | CH=CH—(3-Cl—$C_6H_4$] | (E) |
| A.25 | CH=CH—[4-Cl—$C_6H_4$] | (E) |
| A.26 | CH=CH—[2,4-$Cl_2$—$C_6H_3$] | (E) |
| A.27 | CH=CH—[3,4-$Cl_2$—$C_6H_3$] | (E) |
| A.28 | CH=CH—[2,4,5-$Cl_3$—$C_6H_2$] | (E) |
| A.29 | CH=CH—[2,4,6-$Cl_3$—$C_6H_2$] | (E) |
| A.30 | CH=CH—[2-$CH_3$—$C_6H_4$] | (E) |
| A.31 | CH=CH—[3-$CH_3$—$C_6H_4$] | (E) |
| A.32 | CH=CH—[4-$CH_3$—$C_6H_4$] | (E) |
| A.33 | CH=CH—[2-F, 4-$CH_3$—$C_6H_3$] | (E) |
| A.34 | CH=CH—[2-$CH_3$, 4-F—$C_6H_3$] | (E) |
| A.35 | CH=CH—[3-F, 4-$CH_3$—$C_6H_3$] | (E) |
| A.36 | CH=CH—[3-$CH_3$, 4-F—$C_6H_3$] | (E) |
| A.37 | CH=CH—[2-Cl, 4-$CH_3$—$C_6H_3$] | (E) |
| A.38 | CH=CH—[2-$CH_3$, 4-Cl—$C_6H_3$] | (E) |
| A.39 | CH=CH—[3-Cl, 4-$CH_3$—$C_6H_3$] | (E) |
| A.40 | CH=CH—[3-$CH_3$, 4-Cl—$C_6H_3$] | (E) |
| A.41 | CH=CH—[2,4-$(CH_3)_2$—$C_6H_3$] | (E) |
| A.42 | CH=CH—[3,4-$(CH_3)_2$—$C_6H_3$] | (E) |
| A.43 | CH=CH—[2,4,5-$(CH_3)_3$—$C_6H_2$] | (E) |
| A.44 | CH=CH—[2,4,6-$(CH_3)_3$—$C_6H_2$] | (E) |
| A.45 | CH=CH—[2-$CF_3$—$C_6H_4$] | (E) |
| A.46 | CH=CH—[3-$CF_3$—$C_6H_4$] | (E) |
| A.47 | CH=CH—[4-$CF_3$—$C_6H_4$] | (E) |
| A.48 | CH=CH—[2-F, 4-$CF_3$—$C_6H_3$] | (E) |
| A.49 | CH=CH—[2-$CF_3$, 4-F—$C_6H_3$] | (E) |
| A.50 | CH=CH—[3-F, 4-$CF_3$—$C_6H_3$] | (E) |

TABLE A-continued

| No. | $R^2$ | |
|---|---|---|
| A.51 | CH=CH—[3-$CF_3$, 4-F—$C_6H_3$] | (E) |
| A.52 | CH=CH—[2-Cl, 4-$CF_3$—$C_6H_3$] | (E) |
| A.53 | CH=CH—[2-$CF_3$, 4-Cl—$C_6H_3$] | (E) |
| A.54 | CH=CH—[3-Cl, 4-$CF_3$—$C_6H_3$] | (E) |
| A.55 | CH=CH—[3-$CF_3$, 4-Cl—$C_6H_3$] | (E) |
| A.56 | CH=CH—[2,4-$(CF_3)_2$—$C_6H_3$] | (E) |
| A.57 | CH=CH—[3,4-$(CF_3)_2$—$C_6H_3$] | (E) |
| A.58 | CH=CH—[2,4,5-$(CF_3)_3$—$C_6H_2$] | (E) |
| A.59 | CH=CH—[2,4,6-$(CF_3)_3$—$C_6H_2$] | (E) |
| A.60 | CH=CH—[2-$OCH_3$—$C_6H_4$] | (E) |
| A.61 | CH=CH—[3-$OCH_3$—$C_6H_4$] | (E) |
| A.62 | CH=CH—[4-$OCH_3$—$C_6H_4$] | (E) |
| A.63 | CH=CH—[2-F, 4-$OCH_3$—$C_6H_3$] | (E) |
| A.64 | CH=CH—[2-$OCH_3$, 4-F—$C_6H_3$] | (E) |
| A.65 | CH=CH—[3-F, 4-$OCH_3$—$C_6H_3$] | (E) |
| A.66 | CH=CH—[3-$OCH_3$, 4-F—$C_6H_3$] | (E) |
| A.67 | CH=CH—[2-Cl, 4-$OCH_3$—$C_6H_3$] | (E) |
| A.68 | CH=CH—[2-$OCH_3$, 4-Cl—$C_6H_3$] | (E) |
| A.69 | CH=CH—[3-Cl, 4-$OCH_3$—$C_6H_3$] | (E) |
| A.70 | CH=CH—[3-$OCH_3$, 4-Cl—$C_6H_3$] | (E) |
| A.71 | CH=CH—[2,4-$(OCH_3)_2$—$C_6H_3$] | (E) |
| A.72 | CH=CH—[3,4-$(OCH_3)_2$—$C_6H_3$] | (E) |
| A.73 | CH=CH—[2,4,5-$(OCH_3)_3$—$C_6H_2$] | (E) |
| A.74 | CH=CH—[2,4,6-$(OCH_3)_3$—$C_6H_2$] | (E) |
| A.75 | CH=CH—[2-$OCHF_2$—$C_6H_4$] | (E) |
| A.76 | CH=CH—[3-$OCHF_2$—$C_6H_4$] | (E) |
| A.77 | CH=CH—[4-$OCHF_2$—$C_6H_4$] | (E) |
| A.78 | CH=CH—[2-F, 4-$OCHF_2$—$C_6H_3$] | (E) |
| A.79 | CH=CH—[2-$OCHF_2$, 4-F—$C_6H_3$] | (E) |
| A.80 | CH=CH—[3-F, 4-$OCHF_2$—$C_6H_3$] | (E) |
| A.81 | CH=CH—[3-$OCHF_2$, 4-F—$C_6H_3$] | (E) |
| A.82 | CH=CH—[2-Cl, 4-$OCHF_2$—$C_6H_3$] | (E) |
| A.83 | CH=CH—[2-$OCHF_2$, 4-Cl—$C_6H_3$] | (E) |
| A.84 | CH=CH—[3-Cl, 4-$OCHF_2$—$C_6H_3$] | (E) |
| A.85 | CH=CH—[3-$OCHF_2$, 4-Cl—$C_6H_3$] | (E) |
| A.86 | CH=CH—[2,4-$(OCHF_2)_2$—$C_6H_3$] | (E) |
| A.87 | CH=CH—[3,4-$(OCHF_2)_2$—$C_6H_3$] | (E) |
| A.88 | CH=CH—[2,4,5-$(OCHF_2)_3$—$C_6H_2$] | (E) |
| A.89 | CH=CH—[2,4,6-$(OCHF_2)_3$—$C_6H_2$] | (E) |
| A.90 | $CH_2$CH=$CH_2$ | |
| A.91 | $CH_2$CH=CH—Cl | (E) |
| A.92 | $CH_2$CH=CH—Br | (E) |
| A.93 | $CH_2$CH=CH—$CH_3$ | (E) |
| A.94 | C≡CH | |
| A.95 | C≡C—Cl | |
| A.96 | C≡C—Br | |
| A.97 | C≡C—$CH_3$ | |
| A.98 | C≡C—$C_6H_5$ | |
| A.99 | C≡C—[2-Cl—$C_6H_4$] | |
| A.100 | C≡C—[4-Cl—$C_6H_4$] | |
| A.101 | C≡C—[2,4-$Cl_2$—$C_6H_3$] | |
| A.102 | C≡C—[2-$CH_3$—$C_6H_4$] | |
| A.103 | C≡C—[4-$CH_3$—$C_6H_4$] | |
| A.104 | C≡C—[2,4-$(CH_3)_2$—$C_6H_3$] | |
| A.105 | C≡C—[2-Cl, 4-$CH_3$—$C_6H_3$] | |
| A.106 | C≡C—[2-$CH_3$, 4-Cl—$C_6H_3$] | |
| A.107 | C≡C—[3-$CF_3$—$C_6H_4$] | |
| A.108 | C≡C—[3-Cl, 5-$CF_3$—$C_6H_3$] | |
| A.109 | C≡C—[2-$OCH_3$—$C_6H_4$] | |
| A.110 | C≡C—[4-$OCH_3$—$C_6H_4$] | |
| A.111 | C≡C—[2,4-$(OCH_3)_2$—$C_6H_3$] | |
| A.112 | C≡C—[2-Cl, 4-$OCH_3$—$C_6H_3$] | |
| A.113 | C≡C—[2-$OCH_3$, 4-Cl—$C_6H_3$] | |
| A.114 | C≡C—[3-$OCHF_2$—$C_6H_4$] | |
| A.115 | C≡C—[3-Cl, 5-$OCHF_2$—$C_6H_3$] | |
| A.116 | cyclopentyl | |
| A.117 | 1-$CH_3$-cyclopentyl | |
| A.118 | 2-$CH_3$-cyclopentyl | |
| A.119 | 3-$CH_3$-cyclopentyl | |
| A.120 | 2,3-$(CH_3)_2$-cyclopentyl | |
| A.121 | 1-Cl-cyclopentyl | |
| A.122 | 2-Cl-cyclopentyl | |
| A.123 | 3-Cl-cyclopentyl | |
| A.124 | 2-$CH_3$, 3-Cl-cyclopentyl | |
| A.125 | 2,3-$Cl_2$-cyclopentyl | |
| A.126 | cyclohexyl | |
| A.127 | 1-$CH_3$-cyclohexyl | |

TABLE A-continued

| No. | R² |
|---|---|
| A.128 | 2-CH$_3$-cyclohexyl |
| A.129 | 3-CH$_3$-cyclohexyl |
| A.130 | 2,3-(CH$_3$)$_2$-cyclohexyl |
| A.131 | 3,3-(CH$_3$)$_2$-cyclohexyl |
| A.132 | 1-Cl-cyclohexyl |
| A.133 | 2-Cl-cyclohexyl |
| A.134 | 3-Cl-cyclohexyl |
| A.135 | 2-CH$_3$, 3-Cl-cyclohexyl |
| A.136 | 2,3-Cl$_2$—cyclohexyl |
| A.137 | C$_6$H$_5$ |
| A.138 | 2-CN—C$_6$H$_4$ |
| A.139 | 3-CN—C$_6$H$_4$ |
| A.140 | 4-CN—C$_6$H$_4$ |
| A.141 | 2-F—C$_6$H$_4$ |
| A.142 | 3-F—C$_6$H$_4$ |
| A.143 | 4-F—C$_6$H$_4$ |
| A.144 | 2,4-F$_2$—C$_6$H$_3$ |
| A.145 | 3,4-F$_2$—C$_6$H$_3$ |
| A.146 | 2,4,5-F$_3$—C$_6$H$_2$ |
| A.147 | 2,4,6-F$_3$—C$_6$H$_2$ |
| A.148 | 2-Cl—C$_6$H$_4$ |
| A.149 | 3-Cl—C$_6$H$_4$ |
| A.150 | 4-Cl—C$_6$H$_4$ |
| A.151 | 2,4-Cl$_2$—C$_6$H$_3$ |
| A.152 | 3,4-Cl$_2$—C$_6$H$_3$ |
| A.153 | 2,4,5-Cl$_3$—C$_6$H$_2$ |
| A.154 | 2,4,6-Cl$_3$—C$_6$H$_2$ |
| A.155 | 2-CH$_3$—C$_6$H$_4$ |
| A.156 | 3-CH$_3$—C$_6$H$_4$ |
| A.157 | 4-CH$_3$—C$_6$H$_4$ |
| A.158 | 2-F, 4-CH$_3$—C$_6$H$_3$ |
| A.159 | 2-CH$_3$, 4-F—C$_6$H$_3$ |
| A.160 | 3-F, 4-CH$_3$—C$_6$H$_3$ |
| A.161 | 3-CH$_3$, 4-F—C$_6$H$_3$ |
| A.162 | 2-Cl, 4-CH$_3$—C$_6$H$_3$ |
| A.163 | 2-CH$_3$, 4-Cl—C$_6$H$_3$ |
| A.164 | 3-Cl, 4-CH$_3$—C$_6$H$_3$ |
| A.165 | 3-CH$_3$, 4-Cl—C$_6$H$_3$ |
| A.166 | 2,4-(CH$_3$)$_2$—C$_6$H$_3$ |
| A.167 | 3,4-(CH$_3$)$_2$—C$_6$H$_3$ |
| A.168 | 2,4,5-(CH$_3$)$_3$—C$_6$H$_2$ |
| A.169 | 2,4,6-(CH$_3$)$_3$—C$_6$H$_2$ |
| A.170 | 2-CF$_3$—C$_6$H$_4$ |
| A.171 | 3-CF$_3$—C$_6$H$_4$ |
| A.172 | 4-CF$_3$—C$_6$H$_4$ |
| A.173 | 2-F, 4-CF$_3$—C$_6$H$_3$ |
| A.174 | 2-CF$_3$, 4-F—C$_6$H$_3$ |
| A.175 | 3-F, 4-CF$_3$—C$_6$H$_3$ |
| A.176 | 3-CF$_3$, 4-F—C$_6$H$_3$ |
| A.177 | 2-Cl, 4-CF$_3$—C$_6$H$_3$ |
| A.178 | 2-CF$_3$, 4-Cl—C$_6$H$_3$ |
| A.179 | 3-Cl, 4-CF$_3$—C$_6$H$_3$ |
| A.180 | 3-CF$_3$, 4-Cl—C$_6$H$_3$ |
| A.181 | 2,4-(CF$_3$)$_2$—C$_6$H$_3$ |
| A.182 | 3,4-(CF$_3$)$_2$—C$_6$H$_3$ |
| A.183 | 2,4,5-(CF$_3$)$_3$—C$_6$H$_2$ |
| A.184 | 2,4,6-(CF$_3$)$_3$—C$_6$H$_2$ |
| A.185 | 2-OCH$_3$—C$_6$H$_4$ |
| A.186 | 3-OCH$_3$—C$_6$H$_4$ |
| A.187 | 4-OCH$_3$—C$_6$H$_4$ |
| A.188 | 2-F, 4-OCH$_3$—C$_6$H$_3$ |
| A.189 | 2-OCH$_3$, 4-F—C$_6$H$_3$ |
| A.190 | 3-F, 4-OCH$_3$—C$_6$H$_3$ |
| A.191 | 3-OCH$_3$, 4-F—C$_6$H$_3$ |
| A.192 | 2-Cl, 4-OCH$_3$—C$_6$H$_3$ |
| A.193 | 2-OCH$_3$, 4-Cl—C$_6$H$_3$ |
| A.194 | 3-Cl, 4-OCH$_3$—C$_6$H$_3$ |
| A.195 | 3-OCH$_3$, 4-Cl—C$_6$H$_3$ |
| A.196 | 2,4-(OCH$_3$)$_2$—C$_6$H$_3$ |
| A.197 | 3,4-(OCH$_3$)$_2$—C$_6$H$_3$ |
| A.198 | 2,4,5-(OCH$_3$)$_3$—C$_6$H$_2$ |
| A.199 | 2,4,6-(OCH$_3$)$_3$—C$_6$H$_2$ |
| A.200 | 2-OCHF$_2$—C$_6$H$_4$ |
| A.201 | 3-OCHF$_2$—C$_6$H$_4$ |
| A.202 | 4-OCHF$_2$—C$_6$H$_4$ |
| A.203 | 2-F, 4-OCHF$_2$—C$_6$H$_3$ |
| A.204 | 2-OCHF$_2$, 4-F—C$_6$H$_3$ |
| A.205 | 3-F, 4-OCHF$_2$—C$_6$H$_3$ |
| A.206 | 3-OCHF$_2$, 4-F—C$_6$H$_3$ |
| A.207 | 2-Cl, 4-OCHF$_2$—C$_6$H$_3$ |
| A.208 | 2-OCHF$_2$, 4-Cl—C$_6$H$_3$ |
| A.209 | 3-Cl, 4-OCHF$_2$—C$_6$H$_3$ |
| A.210 | 3-OCHF$_2$, 4-Cl—C$_6$H$_3$ |
| A.211 | 2,4-(OCHF$_2$)$_2$—C$_6$H$_3$ |
| A.212 | 3,4-(OCHF$_2$)$_2$—C$_6$H$_3$ |
| A.213 | 2,4,5-(OCHF$_2$)$_3$—C$_6$H$_2$ |
| A.214 | 2,4,6-(OCHF$_2$)$_3$—C$_6$H$_2$ |
| A.215 | CH$_2$—C$_6$H$_5$ |
| A.216 | CH$_2$—[2-CN—C$_6$H$_4$] |
| A.217 | CH$_2$—[3-CN—C$_6$H$_4$] |
| A.218 | CH$_2$—[4-CN—C$_6$H$_4$] |
| A.219 | CH$_2$—[2-F—C$_6$H$_4$] |
| A.220 | CH$_2$—[3-F—C$_6$H$_4$] |
| A.221 | CH$_2$—[4-F—C$_6$H$_4$] |
| A.222 | CH$_2$—[2,4-F$_2$—C$_6$H$_3$] |
| A.223 | CH$_2$—[3,4-F$_2$—C$_6$H$_3$] |
| A.224 | CH$_2$—[2,4,5-F$_3$—C$_6$H$_2$] |
| A.225 | CH$_2$—[2,4,6-F$_3$—C$_6$H$_2$] |
| A.226 | CH$_2$—[2-Cl—C$_6$H$_4$] |
| A.227 | CH$_2$—[3-Cl—C$_6$H$_4$] |
| A.228 | CH$_2$—[4-Cl—C$_6$H$_4$] |
| A.229 | CH$_2$—[2,4-Cl$_2$—C$_6$H$_3$] |
| A.230 | CH$_2$—[3,4-Cl$_2$—C$_6$H$_3$] |
| A.231 | CH$_2$—[2,4,5-Cl$_3$—C$_6$H$_2$] |
| A.232 | CH$_2$—[2,4,6-Cl$_3$—C$_6$H$_2$] |
| A.233 | CH$_2$—[2-CH$_3$—C$_6$H$_4$] |
| A.234 | CH$_2$—[3-CH$_3$—C$_6$H$_4$] |
| A.235 | CH$_2$—[4-CH$_3$—C$_6$H$_4$] |
| A.236 | CH$_2$—[2-F, 4-CH$_3$—C$_6$H$_3$] |
| A.237 | CH$_2$—[2-CH$_3$, 4-F—C$_6$H$_3$] |
| A.238 | CH$_2$—[3-F, 4-CH$_3$—C$_6$H$_3$] |
| A.239 | CH$_2$—[3-CH$_3$, 4-F—C$_6$H$_3$] |
| A.240 | CH$_2$—[2-Cl, 4-CH$_3$—C$_6$H$_3$] |
| A.241 | CH$_2$—[2-CH$_3$, 4-Cl—C$_6$H$_3$] |
| A.242 | CH$_2$—[3-Cl, 4-CH$_3$—C$_6$H$_3$] |
| A.243 | CH$_2$—[3-CH$_3$, 4-Cl—C$_6$H$_3$] |
| A.244 | CH$_2$—[2,4-(CH$_3$)$_2$—C$_6$H$_3$] |
| A.245 | CH$_2$—[3,4-(CH$_3$)$_2$—C$_6$H$_3$] |
| A.246 | CH$_2$—[2,4,5-(CH$_3$)$_3$—C$_6$H$_2$] |
| A.247 | CH$_2$—[2,4,6-(CH$_3$)$_3$—C$_6$H$_2$] |
| A.248 | CH$_2$—[2-CF$_3$—C$_6$H$_4$] |
| A.249 | CH$_2$—[3-CF$_3$—C$_6$H$_4$] |
| A.250 | CH$_2$—[4-CF$_3$—C$_6$H$_4$] |
| A.251 | CH$_2$—[2-F, 4-CF$_3$—C$_6$H$_3$] |
| A.252 | CH$_2$—[2-CF$_3$, 4-F—C$_6$H$_3$] |
| A.253 | CH$_2$—[3-F, 4-CF$_3$—C$_6$H$_3$] |
| A.254 | CH$_2$—[3-CF$_3$, 4-F—C$_6$H$_3$] |
| A.255 | CH$_2$—[2-Cl, 4-CF$_3$—C$_6$H$_3$] |
| A.256 | CH$_2$—[2-CF$_3$, 4-Cl—C$_6$H$_3$] |
| A.257 | CH$_2$—[3-Cl, 4-CF$_3$—C$_6$H$_3$] |
| A.258 | CH$_2$—[3-CF$_3$, 4-Cl—C$_6$H$_3$] |
| A.259 | CH$_2$—[2,4-(CF$_3$)$_2$—C$_6$H$_3$] |
| A.260 | CH$_2$—[3,4-(CF$_3$)$_2$—C$_6$H$_3$] |
| A.261 | CH$_2$—[2,4,5-(CF$_3$)$_3$—C$_6$H$_2$] |
| A.262 | CH$_2$—[2,4,6-(CF$_3$)$_3$—C$_6$H$_2$] |
| A.263 | CH$_2$—[2-OCH$_3$—C$_6$H$_4$] |
| A.264 | CH$_2$—[3-OCH$_3$—C$_6$H$_4$] |
| A.265 | CH$_2$—[4-OCH$_3$—C$_6$H$_4$] |
| A.266 | CH$_2$—[2-F, 4-OCH$_3$—C$_6$H$_3$] |
| A.267 | CH$_2$—[2-OCH$_3$, 4-F—C$_6$H$_3$] |
| A.268 | CH$_2$—[3-F, 4-OCH$_3$—C$_6$H$_3$] |
| A.269 | CH$_2$—[3-OCH$_3$, 4-F—C$_6$H$_3$] |
| A.270 | CH$_2$—[2-Cl, 4-OCH$_3$—C$_6$H$_3$] |
| A.271 | CH$_2$—[2-OCH$_3$, 4-Cl—C$_6$H$_3$] |
| A.272 | CH$_2$—[3-Cl, 4-OCH$_3$—C$_6$H$_3$] |
| A.273 | CH$_2$—[3-OCH$_3$, 4-Cl—C$_6$H$_3$] |
| A.274 | CH$_2$—[2,4-(OCH$_3$)$_2$—C$_6$H$_3$] |
| A.275 | CH$_2$—[3,4-(OCH$_3$)$_2$—C$_6$H$_3$] |
| A.276 | CH$_2$—[2,4,5-(OCH$_3$)$_3$—C$_6$H$_2$] |
| A.277 | CH$_2$—[2,4,6-(OCH$_3$)$_3$—C$_6$H$_2$] |
| A.278 | CH$_2$—[2-OCHF$_2$—C$_6$H$_4$] |
| A.279 | CH$_2$—[3-OCHF$_2$—C$_6$H$_4$] |
| A.280 | CH$_2$—[4-OCHF$_2$—C$_6$H$_4$] |
| A.281 | CH$_2$—[2-F, 4-OCHF$_2$—C$_6$H$_3$] |

TABLE A-continued

| No. | R² |
|---|---|
| A.282 | CH₂—[2-OCHF₂, 4-F—C₆H₃] |
| A.283 | CH₂—[3-F, 4-OCHF₂—C₆H₃] |
| A.284 | CH₂—[3-OCHF₂, 4-F—C₆H₃] |
| A.285 | CH₂—[2-Cl, 4-OCHF₂—C₆H₃] |
| A.286 | CH₂—[2-OCHF₂, 4-Cl—C₆H₃] |
| A.287 | CH₂—[3-Cl, 4-OCHF₂—C₆H₃] |
| A.288 | CH₂—[3-OCHF₂, 4-Cl—C₆H₃] |
| A.289 | CH₂—[2,4-(OCHF₂)₂—C₆H₃] |
| A.290 | CH₂—[3,4-(OCHF₂)₂—C₆H₃] |
| A.291 | CH₂—[2,4,5-(OCHF₂)₃—C₆H₂] |
| A.292 | CH₂—[2,4,6-(OCHF₂)₃—C₆H₂] |
| A.293 | CH(CH₃)—C₆H₅ |
| A.294 | CH(CH₃)—[2-CN—C₆H₄] |
| A.295 | CH(CH₃)—[3-CN—C₆H₄] |
| A.296 | CH(CH₃)—[4-CN—C₆H₄] |
| A.297 | CH(CH₃)—[2-F—C₆H₄] |
| A.298 | CH(CH₃)—[3-F—C₆H₄) |
| A.299 | CH(CH₃)—[4-F—C₆H₄] |
| A.300 | CH(CH₃)—[2,4-F₂—C₆H₃] |
| A.301 | CH(CH₃)—[3,4-F₂—C₆H₃] |
| A.302 | CH(CH₃)—[2,4,5-F₃—C₆H₂] |
| A.303 | CH(CH₃)—[2,4,6-F₃—C₆H₂] |
| A.304 | CH(CH₃)—[2-Cl—C₆H₄] |
| A.305 | CH(CH₃)—[3-Cl—C₆H₄] |
| A.306 | CH(CH₃)—[4-Cl—C₆H₄] |
| A.307 | CH(CH₃)—[2,4-Cl₂—C₆H₃] |
| A.308 | CH(CH₃)—[3,4-Cl₂—C₆H₃] |
| A.309 | CH(CH₃)—[2,4,5-Cl₃—C₆H₂] |
| A.310 | CH(CH₃)—[2,4,6-Cl₃—C₆H₂] |
| A.311 | CH(CH₃)—[2-CH₃—C₆H₄] |
| A.312 | CH(CH₃)—[3-CH₃—C₆H₄] |
| A.313 | CH(CH₃)—[4-CH₃—C₆H₄] |
| A.314 | CH(CH₃)—[2-F, 4-CH₃—C₆H₃] |
| A.315 | CH(CH₃)—[2-CH₃, 4-F—C₆H₃] |
| A.316 | CH(CH₃)—[3-F, 4-CH₃—C₆H₃] |
| A.317 | CH(CH₃)—[3-CH₃, 4-F—C₆H₃] |
| A.318 | CH(CH₃)—[2-Cl, 4-CH₃—C₆H₃] |
| A.319 | CH(CH₃)—[2-CH₃, 4-Cl—C₆H₃] |
| A.320 | CH(CH₃)—[3-Cl, 4-CH₃—C₆H₃] |
| A.321 | CH(CH₃)—[3-CH₃, 4-Cl—C₆H₃] |
| A.322 | CH(CH₃)—[2,4-(CH₃)₂—C₆H₃] |
| A.323 | CH(CH₃)—[3,4-(CH₃)₂—C₆H₃] |
| A.324 | CH(CH₃)—[2,4,5-(CH₃)₃—C₆H₂] |
| A.325 | CH(CH₃)—[2,4,6-(CH₃)₃—C₆H₂] |
| A.326 | CH(CH₃)—[2-CF₃—C₆H₄] |
| A.327 | CH(CH₃)—[3-CF₃—C₆H₄] |
| A.328 | CH(CH₃)—[4-CF₃—C₆H₄] |
| A.329 | CH(CH₃)—[2-F, 4-CF₃—C₆H₃] |
| A.330 | CH(CH₃)—[2-CF₃, 4-F—C₆H₃] |
| A.331 | CH(CH₃)—[3-F, 4-CF₃—C₆H₃] |
| A.332 | CH(CH₃)—[3-CF₃, 4-F—C₆H₃] |
| A.333 | CH(CH₃)—[2-Cl, 4-CF₃—C₆H₃] |
| A.334 | CH(CH₃)—[2-CF₃, 4-Cl—C₆H₃] |
| A.335 | CH(CH₃)—[3-Cl, 4-CF₃—C₆H₃] |
| A.336 | CH(CH₃)—[3-CF₃, 4-Cl—C₆H₃] |
| A.337 | CH(CH₃)—[2,4-(CF₃)₂—C₆H₃] |
| A.338 | CH(CH₃)—[3,4-(CF₃)₂—C₆H₃] |
| A.339 | CH(CH₃)—[2,4,5-(CF₃)₃—C₆H₂] |
| A.340 | CH(CH₃)—[2,4,6-(CF₃)₃—C₆H₂] |
| A.341 | CH(CH₃)—[2-OCH₃—C₆H₄] |
| A.342 | CH(CH₃)—[3-OCH₃—C₆H₄] |
| A.343 | CH(CH₃)—[4-OCH₃—C₆H₄] |
| A.344 | CH(CH₃)—[2-F, 4-OCH₃—C₆H₃] |
| A.345 | CH(CH₃)—[2-OCH₃, 4-F—C₆H₃] |
| A.346 | CH(CH₃)—[3-F, 4-OCH₃—C₆H₃] |
| A.347 | CH(CH₃)—[3-OCH₃, 4-F—C₆H₃] |
| A.348 | CH(CH₃)—[2-Cl, 4-OCH₃—C₆H₃] |
| A.349 | CH(CH₃)—[2-OCH₃, 4-Cl—C₆H₃] |
| A.350 | CH(CH₃)—[3-Cl, 4-OCH₃—C₆H₃] |
| A.351 | CH(CH₃)—[3-OCH₃, 4-Cl—C₆H₃] |
| A.352 | CH(CH₃)—[2,4-(OCH₃)₂—C₆H₃] |
| A.353 | CH(CH₃)—[3,4-(OCH₃)₂—C₆H₃] |
| A.354 | CH(CH₃)—[2,4,5-(OCH₃)₃—C₆H₂] |
| A.355 | CH(CH₃)—[2,4,6-(OCH₃)₃—C₆H₂] |
| A.356 | CH(CH₃)—[2-OCHF₂—C₆H₄] |
| A.357 | CH(CH₃)—[3-OCHF₂—C₆H₄] |
| A.358 | CH(CH₃)—[4-OCHF₂—C₆H₄] |
| A.359 | CH(CH₃)—[2-F, 4-OCHF₂—C₆H₃] |
| A.360 | CH(CH₃)—[2-OCHF₂, 4-F—C₆H₃] |
| A.361 | CH(CH₃)—[3-F, 4-OCHF₂—C₆H₃] |
| A.362 | CH(CH₃)—[3-OCHF₂, 4-F—C₆H₃] |
| A.363 | CH(CH₃)—[2-Cl, 4-OCHF₂—C₆H₃] |
| A.364 | CH(CH₃)—[2-OCHF₂, 4-Cl—C₆H₃] |
| A.365 | CH(CH₃)—[3-Cl, 4-OCHF₂—C₆H₃] |
| A.366 | CH(CH₃)—[3-OCHF₂, 4-Cl—C₆H₃] |
| A.367 | CH(CH₃)—[2,4-(OCHF₂)₂—C₆H₃] |
| A.368 | CH(CH₃)—[3,4-(OCHF₂)₂—C₆H₃] |
| A.369 | CH(CH₃)—[2,4,5-(OCHF₂)₃—C₆H₂] |
| A.370 | CH(CH₃)—[2,4,6-(OCHF₂)₃—C₆H₂] |
| A.371 | CH₂F |
| A.372 | CHF₂ |
| A.373 | CF₃ |
| A.374 | CH₂—CN |
| A.375 | CH₂—OCH₃ |
| A.376 | CH₂—OCH₂CH₃ |
| A.377 | CH₂—OCH₂CH₂CH₃ |
| A.378 | CH₂—OCH(CH₃)₂ |
| A.379 | CH₂—OCH₂CH₂CH₂CH₃ |
| A.380 | CH₂—OCH(CH₃)CH₂CH₃ |
| A.381 | CH₂—OCH₂CH(CH₃)₂ |
| A.382 | CH₂—OC(CH₃)₃ |
| A.383 | CH₂—OCF₃ |
| A.384 | CH₂—OCH₂CF₃ |
| A.385 | CH₂CH₂—OCH₂CH₃ |
| A.386 | CH₂CH₂—OCH(CH₃)₂ |
| A.387 | CH₂CH₂—OCH₂CH₂CH₂CH₃ |
| A.388 | CH₂CH₂—OCH(CH₃)CH₂CH₃ |
| A.389 | CH₂CH₂—OCH₂CH(CH₃)₂ |
| A.390 | CH₂CH₂—OC(CH₃)₃ |
| A.391 | CH₂CH₂—OCF₃ |
| A.392 | CH₂CH₂—OCH₂CF₃ |
| A.393 | CH₂CH₂—[C₆H₅] |
| A.394 | CH₂CH₂—[2-CN—C₆H₄] |
| A.395 | CH₂CH₂—[3-CN—C₆H₄] |
| A.396 | CH₂CH₂—[4-CN—C₆H₄] |
| A.397 | CH₂CH₂—[2-F—C₆H₄] |
| A.398 | CH₂CH₂—[3-F—C₆H₄] |
| A.399 | CH₂CH₂—[4-F—C₆H₄] |
| A.400 | CH₂CH₂—[2,4-F₂—C₆H₃] |
| A.401 | CH₂CH₂—[3,4-F₂—C₆H₃] |
| A.402 | CH₂CH₂—[2,4,5-F₃—C₆H₂] |
| A.403 | CH₂CH₂—[2,4,6-F₃—C₆H₂] |
| A.404 | CH₂CH₂—[2-Cl—C₆H₄] |
| A.405 | CH₂CH₂—[3-Cl—C₆H₄] |
| A.406 | CH₂CH₂—[4-Cl—C₆H₄] |
| A.407 | CH₂CH₂—[2,4-Cl₂—C₆H₃] |
| A.408 | CH₂CH₂—[3,4-Cl₂—C₆H₃] |
| A.409 | CH₂CH₂—[2,4,5-Cl₃—C₆H₂] |
| A.410 | CH₂CH₂—[2,4,6-Cl₃—C₆H₂] |
| A.411 | CH₂CH₂—[2-CH₃—C₆H₄] |
| A.412 | CH₂CH₂—[3-CH₃—C₆H₄] |
| A.413 | CH₂CH₂—[4-CH₃—C₆H₄] |
| A.414 | CH₂CH₂—[2-F, 4-CH₃—C₆H₃] |
| A.415 | CH₂CH₂—[2-CH₃, 4-F—C₆H₃] |
| A.416 | CH₂CH₂—[3-F, 4-CH₃—C₆H₃] |
| A.417 | CH₂CH₂—[3-CH₃, 4-F—C₆H₃] |
| A.418 | CH₂CH₂—[2-Cl, 4-CH₃—C₆H₃] |
| A.419 | CH₂CH₂—[2-Cl, 4-CH₃—C₆H₃] |
| A.420 | CH₂CH₂—[3-Cl, 4-CH₃—C₆H₃] |
| A.421 | CH₂CH₂—[3-CH₃, 4-Cl—C₆H₃] |
| A.422 | CH₂CH₂—[2,4-(CH₃)₂—C₆H₃] |
| A.423 | CH₂CH₂—[3,4-(CH₃)₂—C₆H₃] |
| A.424 | CH₂CH₂—[2,4,5-(CH₃)₃—C₆H₂] |
| A.425 | CH₂CH₂—[2,4,6-(CH₃)₃—C₆H₂] |
| A.426 | CH₂CH₂—[2-CF₃—C₆H₄] |
| A.427 | CH₂CH₂—[3-CF₃—C₆H₄) |
| A.428 | CH₂CH₂—[4-CF₃—C₆H₄] |
| A.429 | CH₂CH₂—[2-F, 4-CF₃—C₆H₃] |
| A.430 | CH₂CH₂—[2-CF₃, 4-F—C₆H₃] |
| A.431 | CH₂CH₂—[3-F, 4-CF₃—C₆H₃] |
| A.432 | CH₂CH₂—[3-CF₃, 4-F—C₆H₃] |
| A.433 | CH₂CH₂—[2-Cl, 4-CF₃—C₆H₃] |
| A.434 | CH₂CH₂—[2-CF₃, 4-Cl—C₆H₃) |
| A.435 | CH₂CH₂—[3-Cl, 4-CF₃—C₆H₃] |

TABLE A-continued

| No. | R² | |
|---|---|---|
| A.436 | CH₂CH₂—[3-CF₃, 4-Cl—C₆H₃] | |
| A.437 | CH₂CH₂—[2,4-(CF₃)₂—C₆H₃] | |
| A.438 | CH₂CH₂—[3,4-(CF₃)₂—C₆H₃] | |
| A.439 | CH₂CH₂—[2,4,5-(CF₃)₃—C₆H₂] | |
| A.440 | CH₂CH₂—[2,4,6-(CF₃)₃—C₆H₂] | |
| A.441 | CH₂CH₂—[2-OCH₃—C₆H₄] | |
| A.442 | CH₂CH₂—[3-OCH₃—C₆H₄] | |
| A.443 | CH₂CH₂—[4-OCH₃—C₆H₄] | |
| A.444 | CH₂CH₂—[2-F, 4-OCH₃—C₆H₃] | |
| A.445 | CH₂CH₂—[2-OCH₃, 4-F—C₆H₃] | |
| A.446 | CH₂CH₂—[3-F, 4-OCH₃—C₆H₃] | |
| A.447 | CH₂CH₂—[3-OCH₃, 4-F—C₆H₃] | |
| A.448 | CH₂CH₂—[2-Cl, 4-OCH₃—C₆H₃] | |
| A.449 | CH₂CH₂—[2-OCH₃, 4-Cl—C₆H₃] | |
| A.450 | CH₂CH₂—[3-Cl, 4-OCH₃—C₆H₃] | |
| A.451 | CH₂CH₂—[3-OCH₃, 4-Cl—C₆H₃] | |
| A.452 | CH₂CH₂—[2,4-(OCH₃)₂—C₆H₃] | |
| A.453 | CH₂CH₂—[3,4-(OCH₃)₂—C₆H₃] | |
| A.454 | CH₂CH₂—[2,4,5-(OCH₃)₃—C₆H₂] | |
| A.455 | CH₂CH₂—[2,4,6-(OCH₃)₃—C₆H₂] | |
| A.456 | CH₂CH₂—[2-OCHF₂—C₆H₄] | |
| A.457 | CH₂CH₂—[3-OCHF₂—C₆H₄] | |
| A.458 | CH₂CH₂—[4-OCHF₂—C₆H₄] | |
| A.459 | CH₂CH₂—[2-F, 4-OCHF₂—C₆H₃] | |
| A.460 | CH₂CH₂—[2-OCHF₂, 4-F—C₆H₃] | |
| A.461 | CH₂CH₂—[3-F, 4-OCHF₂—C₆H₃] | |
| A.462 | CH₂CH₂—[3-OCHF₂, 4-F—C₆H₃] | |
| A.463 | CH₂CH₂—[2-Cl, 4-OCHF₂—C₆H₃] | |
| A.464 | CH₂CH₂—[2-OCHF₂, 4-Cl—C₆H₃] | |
| A.465 | CH₂CH₂—[3-Cl, 4-OCHF₂—C₆H₃] | |
| A.466 | CH₂CH₂—[3-OCHF₂, 4-Cl—C₆H₃] | |
| A.467 | CH₂CH₂—[2,4-(OCHF₂)₂—C₆H₃] | |
| A.468 | CH₂CH₂—[3,4-(OCHF₂)₂—C₆H₃] | |
| A.469 | CH₂CH₂—[2,4,5-(OCHF₂)₃—C₆H₂] | |
| A.470 | CH₂CH₂—[2,4,6-(OCHF₂)₃—C₆H₂]) | |
| A.471 | CH(CH₃)—CN | |
| A.472 | CH(CH₃)—OCH₃ | |
| A.473 | CH(CH₃)—OCH₂CH₃ | |
| A.474 | CH(CH₃)—OCH₂CH₂CH₃ | |
| A.475 | CH(CH₃)—OCH(CH₃)₂ | |
| A.476 | CH(CH₃)—OCH₂CH2CH₂CH₃ | |
| A.477 | CH(CH₃)—OCH(CH₃)CH₂CH₃ | |
| A.478 | CH(CH₃)—OCH₂CH(CH₃)₂ | |
| A.479 | CH(CH₃)—OC(CH₃)₃ | |
| A.480 | CH(CH₃)—OCF₃ | |
| A.481 | CH(CH₃)—OCH₂CF₃ | |
| A.482 | CH₂CH₂F | |
| A.483 | CH₂CHF₂ | |
| A.484 | CH₂CF₃ | |
| A.485 | CHFCH₃ | |
| A.486 | CF₂CH₃ | |
| A.487 | CHFCHF₂ | |
| A.488 | CHFCF₃ | |
| A.489 | CF₂CHF₂ | |
| A.490 | CF₂CF₃ | |
| A.491 | CF₂CHFCl | |
| A.492 | CH₂CH₂CH₂—CN | |
| A.493 | CH₂CH₂CH₂—OCH₃ | |
| A.494 | CH₂CH₂CH₂—OCH₂CH₃ | |
| A.495 | CH₂CH₂CH₂—OCH₂CH₂CH₃ | |
| A.496 | CH₂CH₂CH₂—OCH(CH₃)₂ | |
| A.497 | CH₂CH₂CH₂—OCF₃ | |
| A.498 | CH₂CH₂CH₂—OCH₂CF₃ | |
| A.499 | CH₂CH(CH₃)—CN | |
| A.500 | CH₂CH(CH₃)—OCH₃ | |
| A.501 | CH₂CH(CH₃)—OCH₂CH₃ | |
| A.502 | CH₂CH(CH₃)—OCH₂CH₂CH₃ | |
| A.503 | CH₂CH(CH₃)—OCH(CH₃)₂ | |
| A.504 | CH₂CH(CH₃)—OCF₃ | |
| A.505 | CH₂CH(CH₃)—OCH₂CF₃ | |
| A.506 | CH(CH₂CH₃)—CN | |
| A.507 | CH(CH₂CH₃)—OCH₃ | |
| A.508 | CH(CH₂CH₃)—OCH₂CH₃ | |
| A.509 | CH(CH₂CH₃)—OCH₂CH₂CH₃ | |
| A.510 | CH(CH₂CH₃)—OCH(CH₃)₂ | |
| A.511 | CH(CH₂CH₃)—OCF₃ | |
| A.512 | CH(CH₂CH₃)—OCH₂CF₃ | |
| A.513 | CH(CH₃)CH₂—CN | |
| A.514 | CH(CH₃)CH₂—OCH₃ | |
| A.515 | CH(CH₃)CH₂—OCH₂CH₃ | |
| A.516 | CH(CH₃)CH₂—OCH₂CH₂CH₃ | |
| A.517 | CH(CH₃)CH₂—OCH(CH₃)₂ | |
| A.518 | CH(CH₃)CH₂—OCF₃ | |
| A.519 | CH(CH₃)CH₂—OCH₂CF₃ | |
| A.520 | CH₂CH₂CF₃ | |
| A.521 | CH₂CF₂CF₃ | |
| A.522 | CHFCH₂CH₃ | |
| A.523 | CH(CF₃)CH₃ | |
| A.524 | CH(CF₃)₂ | |
| A.525 | CH₂CH₂CH₂CH₂—CN | |
| A.526 | CH₂CH₂CH₂CH₂—OCH₃ | |
| A.527 | CH₂CH₂CH₂CH₂—OCH₂CH₃ | |
| A.528 | CH₂CH₂CH₂CH₂—OCF₃ | |
| A.529 | CH(CN)—CH₂CH₂CH₃ | |
| A.530 | CH(OCH₃)—CH₂CH₂CH₃ | |
| A.531 | CH(OCH₂CH₃)—CH₂CH₂CH₃ | |
| A.532 | CH(OCF₃)—CH₂CH₂CH₃ | |
| A.533 | CH(OCH₂CF₃)—CH₂CH₂CH₃ | |
| A.534 | CH(CN)—CH₂CH(CH₃)₂ | |
| A.535 | CH(OCH₃)—CH₂CH(CH₃)₂ | |
| A.536 | CH(OCH₂CH₃)—CH₂CH(CH₃)₂ | |
| A.537 | CH(OCF₃)—CH₂CH(CH₃)₂ | |
| A.538 | CH(OCH₂CF₃)—CH₂CH(CH₃)₂ | |
| A.539 | CHFCH₂CH₂CH₃ | |
| A.540 | C(CH₃)=CH₂ | |
| A.541 | CH=CH—CH₃ | (Z) |
| A.542 | C(CH₂CH₃)=CH₂ | |
| A.543 | C(CH₃)=CH—CH₃ | (E) |
| A.544 | C(CH₃)=CH—CH₃ | (Z) |
| A.545 | C(CH₃)=C(CH₃)₂ | |
| A.546 | CH(CH₃)—CH=CH₂ | |
| A.547 | CH=C(CH₃)₂ | |
| A.548 | CH₂—C(CH₃)=CH₂ | |
| A.549 | CH(CH₃)—CH₂—CH=CH₂ | |
| A.550 | CH₂—CH(CH₃)—CH=CH₂ | |
| A.551 | CH₂—CCl=CH₂ | |
| A.552 | CH₂—CH=CH—Cl | (Z) |
| A.553 | CH₂—CCl=CH—Cl | (E) |
| A.554 | CH₂—CCl=CH—Cl | (Z) |
| A.555 | CH₂—CH=CCl₂ | |
| A.556 | CH₂—CCl=CCl₂ | |
| A.557 | CH₂—CBr=CH₂ | |
| A.558 | CH₂—CH=CH—Br | (Z) |
| A.559 | CH₂—CBr=CH—Br | (E) |
| A.560 | CH₂—CBr=CH—Br | (Z) |
| A.561 | CH₂—CH=CBr₂ | |
| A.562 | CH₂—CBr=CBr₂ | |
| A.563 | CH₂—CH=CH—CH₃ | (Z) |
| A.564 | CH₂—C(CH₃)=CH—CH₃ | (E) |
| A.565 | CH₂—C(CH₃)=CH—CH₃ | (Z) |
| A.566 | CH₂—CH=C(CH₃)₂ | |
| A.567 | CH₂—CH₂—CH=CH₂ | |
| A.568 | CH₂—CCl=CH—CH₃ | (E) |
| A.569 | CH₂—CCl=CH—CH₃ | (Z) |
| A.570 | CH₂—CH=CCl—CH₃ | (E) |
| A.571 | CH₂—CH=CCl—CH₃ | (Z) |
| A.572 | CH₂—C(CH₃)=C(CH₃)₂ | |
| A.573 | CH₂—CBr=CH—CH₃ | (E) |
| A.574 | CH₂—CBr=CH—CH₃ | (Z) |
| A.575 | CH₂—CH=CBr—CH₃ | (E) |
| A.576 | CH₂—CH=CBr—CH₃ | (Z) |
| A.577 | CH₂—CH=CH—CH₂Cl | (E) |
| A.578 | CH₂—CH=CH—CH₂Cl | (Z) |
| A.579 | CH₂—CH=CH—CH₂CH₃ | (E) |
| A.580 | CH₂—CH=CH—CH₂CH₃ | (Z) |
| A.581 | CH₂—CH=CH—CH₂Br | (E) |
| A.582 | CH₂—CH=CH—CH₂Br | (Z) |
| A.583 | CH₂—CCl=CCl—CH₂Cl | (E) |
| A.584 | CH₂—CCl=CCl—CH₂Cl | (Z) |
| A.585 | CH₂—CF=CH₂ | |
| A.586 | CH₂—CH=CH—F | (E) |
| A.587 | CH₂—CH=CH—F | (Z) |
| A.588 | CH₂—CH=CF₂ | |
| A.589 | CH₂—CF=CH—F | (E) |

TABLE A-continued

| No. | R² | |
|---|---|---|
| A.590 | CH₂—CF=CH—F | (Z) |
| A.591 | CH(CH₃)—CH=CH₂ | |
| A.592 | CH(CH₃)—CCl=CH₂ | |
| A.593 | CH(CH₃)—CH=CH—Cl | (E) |
| A.594 | CH(CH₃)—CH=CH—Cl | (Z) |
| A.595 | CH(CH₃)—CCl=CH—Cl | (E) |
| A.596 | CH(CH₃)—CCl=CH—Cl | (Z) |
| A.597 | CH(CH₃)—CH=CCl₂ | |
| A.598 | CH(CH₃)—CCl=CCl₂ | |
| A.599 | CH(CH₃)—CBr=CH₂ | |
| A.600 | CH(CH₃)—CH=CH—Br | (E) |
| A.601 | CH(CH₃)—CH=CH—Br | (Z) |
| A.602 | CH(CH₃)—CBr=CH—Br | (E) |
| A.603 | CH(CH₃)—CBr=CH—Br | (Z) |
| A.604 | CH(CH₃)—CH=CBr₂ | |
| A.605 | CH(CH₃)—CBr=CBr₂ | |
| A.606 | CH(CH₃)—C(CH₃)=CH₂ | |
| A.607 | CH(CH₃)—CH=CH—CH₃ | (E) |
| A.608 | CH(CH₃)—CH=CH—CH₃ | (Z) |
| A.609 | CH(CH₃)—C(CH₃)=CH—CH₃ | (E) |
| A.610 | CH(CH₃)—C(CH₃)=CH—CH₃ | (Z) |
| A.611 | CH(CH₃)—CH=C(CH₃)₂ | |
| A.612 | CH(CH₃)—CCl=CH—CH₃ | (E) |
| A.613 | CH(CH₃)—CCl=CH—CH₃ | (Z) |
| A.614 | CH(CH₃)—CH=CCl—CH₃ | (E) |
| A.615 | CH(CH₃)—CH=CCl—CH₃ | (Z) |
| A.616 | CH(CH₃)—CBr=CH—CH₃ | (E) |
| A.617 | CH(CH₃)—CBr=CH—CH₃ | (Z) |
| A.618 | CH(CH₃)—CH=CBr—CH₃ | (E) |
| A.619 | CH(CH₃)—CH=CBr—CH₃ | (Z) |
| A.620 | CH(CH₃)—CH=CH—CH₂Cl | (E) |
| A.621 | CH(CH₃)—CH=CH—CH₂Cl | (Z) |
| A.622 | CH(CH₃)—CH=CH—CH₂CH₃ | (E) |
| A.623 | CH(CH₃)—CH=CH—CH₂CH₃ | (Z) |
| A.624 | CH(CH₃)—CH=CH—CH₂Br | (E) |
| A.625 | CH(CH₃)—CH=CH—CH₂Br | (Z) |
| A.626 | CH(CH₃)—CCl=CCl—CH₂Cl | (E) |
| A.627 | CH(CH₃)—CCl=CCl—CH₂Cl | (Z) |
| A.628 | CH(CH₃)—CF=CH₂ | |
| A.629 | CH(CH₃)—CH=CH—F | (E) |
| A.630 | CH(CH₃)—CH=CH—F | (Z) |
| A.631 | CH(CH₃)—CH=CF₂ | |
| A.632 | CH(CH₃)—CF=CH—F | (E) |
| A.633 | CH(CH₃)—CF=CH—F | (Z) |
| A.634 | CH₂CHCl—CH=CH₂ | |
| A.635 | CH₂CH₂—CH=C(CH₃)₂ | |
| A.636 | CH₂CH₂—C(CH₃)=CH—CH₃ | (E) |
| A.637 | CH₂CH₂—C(CH₃)=CH—CH₃ | (Z) |
| A.638 | C(CH₃)=CH—[C₆H₅] | (E) |
| A.639 | C(CH₃)=CH—[2-CN—C₆H₄] | (E) |
| A.640 | C(CH₃)=CH—[3-CN—C₆H₄] | (E) |
| A.641 | C(CH₃)=CH—[4-CN—C₆H₄] | (E) |
| A.642 | C(CH₃)=CH—[2-F—C₆H₄] | (E) |
| A.643 | C(CH₃)=CH—[3-F—C₆H₄] | (E) |
| A.644 | C(CH₃)=CH—[4-F—C₆H₄] | (E) |
| A.645 | C(CH₃)=CH—[2,4-F₂—C₆H₃] | (E) |
| A.646 | C(CH₃)=CH—[3,4-F₂—C₆H₃] | (E) |
| A.647 | C(CH₃)=CH—[2,4,5-F₃—C₆H₂] | (E) |
| A.648 | C(CH₃)=CH—[2,4,6-F₃—C₆H₂] | (E) |
| A.649 | C(CH₃)=CH—[2-Cl—C₆H₄] | (E) |
| A.650 | C(CH₃)=CH—[3-Cl—C₆H₄] | (E) |
| A.651 | C(CH₃)=CH—[4-Cl—C₆H₄] | (E) |
| A.652 | C(CH₃)=CH—[2,4-Cl₂—C₆H₃] | (E) |
| A.653 | C(CH₃)=CH—[3,4-Cl₂—C₆H₃] | (E) |
| A.654 | C(CH₃)=CH—[2,4,5-Cl₃—C₆H₂] | (E) |
| A.655 | C(CH₃)=CH—[2,4,6-Cl₃—C₆H₂] | (E) |
| A.656 | C(CH₃)=CH—[2-CH₃—C₆H₄] | (E) |
| A.657 | C(CH₃)=CH—[3-CH₃—C₆H₄] | (E) |
| A.656 | C(CH₃)=CH—[4-CH₃—C₆H₄] | (E) |
| A.659 | C(CH₃)=CH—[2-F, 4-CH₃—C₆H₃] | (E) |
| A.660 | C(CH₃)=CH—[2-CH₃, 4-F—C₆H₃] | (E) |
| A.661 | C(CH₃)=CH—[3-F, 4-CH₃—C₆H₃] | (E) |
| A.662 | C(CH₃)=CH—[3-CH₃, 4-F—C₆H₃] | (E) |
| A.663 | C(CH₃)=CH—[2-Cl, 4-CH₃—C₆H₃] | (E) |
| A.664 | C(CH₃)=CH—[2-CH₃, 4-Cl—C₆H₃] | (E) |
| A.665 | C(CH₃)=CH—[3-Cl, 4-CH₃—C₆H₃] | (E) |
| A.666 | C(CH₃)=CH—[3-CH₃, 4-Cl—C₆H₃] | (E) |
| A.667 | C(CH₃)=CH—[2,4-(CH₃)₂—C₆H₃] | (E) |
| A.668 | C(CH₃)=CH—[3,4-(CH₃)₂—C₆H₃] | (E) |
| A.669 | C(CH₃)=CH—[2,4,5-(CH₃)₃—C₆H₂] | (E) |
| A.670 | C(CH₃)=CH—[2,4,6-(CH₃)₃—C₆H₂] | (E) |
| A.671 | C(CH₃)=CH—[2-CF₃—C₆H₄] | (E) |
| A.672 | C(CH₃)=CH—[3-CF₃—C₆H₄] | (E) |
| A.673 | C(CH₃)=CH—[4-CF₃—C₆H₄] | (E) |
| A.674 | C(CH₃)=CH—[2-F, 4-CF₃—C₆H₃] | (E) |
| A.675 | C(CH₃)=CH—[2-CF₃, 4-F—C₆H₃] | (E) |
| A.676 | C(CH₃)=CH—[3-F, 4-CF₃—C₆H₃] | (E) |
| A.677 | C(CH₃)=CH—[3-CF₃, 4-F—C₆H₃] | (E) |
| A.678 | C(CH₃)=CH—[2-Cl, 4-CF₃—C₆H₃] | (E) |
| A.679 | C(CH₃)=CH—[2-CF₃, 4-Cl—C₆H₃] | (E) |
| A.680 | C(CH₃)=CH—[3-Cl, 4-CF₃—C₆H₃] | (E) |
| A.681 | C(CH₃)=CH—[3-CF₃, 4-Cl—C₆H₃] | (E) |
| A.682 | C(CH₃)=CH—[2,4-(CF₃)₂—C₆H₃] | (E) |
| A.683 | C(CH₃)=CH—[3,4-(CF₃)₂—C₆H₃] | (E) |
| A.684 | C(CH₃)=CH—[2,4,5-(CF₃)₃—C₆H₂] | (E) |
| A.685 | C(CH₃)=CH—[2,4,6-(CF₃)₃—C₆H₂] | (E) |
| A.686 | C(CH₃)=CH—[2-OCH₃—C₆H₄] | (E) |
| A.687 | C(CH₃)=CH—[3-OCH₃—C₆H₄] | (E) |
| A.688 | C(CH₃)=CH—[4-OCH₃—C₆H₄] | (E) |
| A.689 | C(CH₃)=CH—[2-F, 4-OCH₃—C₆H₃] | (E) |
| A.690 | C(CH₃)=CH—[2-OCH₃, 4-F—C₆H₃] | (E) |
| A.691 | C(CH₃)=CH—[3-F, 4-OCH₃—C₆H₃] | (E) |
| A.692 | C(CH₃)=CH—[3-OCH₃, 4-F—C₆H₃] | (E) |
| A.693 | C(CH₃)=CH—[2-Cl, 4-OCH₃—C₆H₃] | (E) |
| A.694 | C(CH₃)=CH—[2-OCH₃, 4-Cl—C₆H₃] | (E) |
| A.695 | C(CH₃)=CH—[3-Cl, 4-OCH₃—C₆H₃] | (E) |
| A.696 | C(CH₃)=CH—[3-OCH₃, 4-Cl—C₆H₃] | (E) |
| A.697 | C(CH₃)=CH—[2,4-(OCH₃)₂—C₆H₃] | (E) |
| A.698 | C(CH₃)=CH—[3,4-(OCH₃)₂—C₆H₃] | (E) |
| A.699 | C(CH₃)=CH—(2,4,5-(OCH₃)₃—C₆H₂) | (E) |
| A.700 | C(CH₃)=CH—[2,4,6-(OCH₃)₃—C₆H₂] | (E) |
| A.701 | C(CH₃)=CH—[2-OCHF₂—C₆H₄] | (E) |
| A.702 | C(CH₃)=CH—[3-OCHF₂—C₆H₄] | (E) |
| A.703 | C(CH₃)=CH—[4-OCHF₂—C₆H₄] | (E) |
| A.704 | C(CH₃)=CH—[2-F, 4-OCHF₂—C₆H₃] | (E) |
| A.705 | C(CH₃)=CH—[2-OCHF₂, 4-F—C₆H₃] | (E) |
| A.706 | C(CH₃)=CH—[3-F, 4-OCHF₂—C₆H₃] | (E) |
| A.707 | C(CH₃)=CH—[3-OCHF₂, 4-F—C₆H₃] | (E) |
| A.708 | C(CH₃)=CH—[2-Cl, 4-OCHF₂—C₆H₃] | (E) |
| A.709 | C(CH₃)=CH—[2-OCHF₂, 4-Cl—C₆H₃] | (E) |
| A.710 | C(CH₃)=CH—[3-Cl, 4-OCHF₂—C₆H₃] | (E) |
| A.711 | C(CH₃)=CH—[3-OCHF₂, 4-Cl—C₆H₃] | (E) |
| A.712 | C(CH₃)=CH—[2,4-(OCHF₂)₂—C₆H₃] | (E) |
| A.713 | C(CH₃)=CH—[3,4-(OCHF₂)₂—C₆H₃] | (E) |
| A.714 | C(CH₃)=CH—[2,4,5-(OCHF₂)₃—C₆H₂] | (E) |
| A.715 | C(CH₃)=CH—[2,4,6-(OCHF₂)₃—C₆H₂] | (E) |
| A.716 | CH=C(CH₃)—[C₆H₅] | (E) |
| A.717 | CH=C(CH₃)—[2-CN—C₆H₄] | (E) |
| A.718 | CH=C(CH₃)—[3-CN—C₆H₄] | (E) |
| A.719 | CH=C(CH₃)—[4-CN—C₆H₄] | (E) |
| A.720 | CH=C(CH₃)—[2-F—C₆H₄] | (E) |
| A.721 | CH=C(CH₃)—[3-F—C₆H₄] | (E) |
| A.722 | CH=C(CH₃)—[4-F—C₆H₄] | (E) |
| A.723 | CH=C(CH₃)—[2,4-F₂—C₆H₃] | (E) |
| A.724 | CH=C(CH₃)—[3,4-F₂—C₆H₃] | (E) |
| A.725 | CH=C(CH₃)—[2,4,5-F₃—C₆H₂] | (E) |
| A.726 | CH=C(CH₃)—[2,4,6-F₃—C₆H₂] | (E) |
| A.727 | CH=C(CH₃)—[2-Cl—C₆H₄] | (E) |
| A.728 | CH=C(CH₃)—[3-Cl—C₆H₄] | (E) |
| A.729 | CH=C(CH₃)—[4-Cl—C₆H₄] | (E) |
| A.730 | CH=C(CH₃)—[2,4-Cl₂—C₆H₃] | (E) |
| A.731 | CH=C(CH₃)—[3,4-Cl₂—C₆H₃] | (E) |
| A.732 | CH=C(CH₃)—[2,4,5-Cl₃—C₆H₂] | (E) |
| A.733 | CH=C(CH₃)—[2,4,6-Cl₃—C₆H₂] | (E) |
| A.734 | CH=C(CH₃)—[2-CH₃—C₆H₄] | (E) |
| A.735 | CH=C(CH₃)—[3-CH₃—C₆H₄] | (E) |
| A.736 | CH=C(CH₃)—[4-CH₃—C₆H₄] | (E) |
| A.737 | CH=C(CH₃)—[2-F, 4-CH₃—C₆H₃] | (E) |
| A.738 | CH=C(CH₃)—[2-CH₃, 4-F—C₆H₃] | (E) |
| A.739 | CH=C(CH₃)—[3-F, 4-CH₃—C₆H₃] | (E) |
| A.740 | CH=C(CH₃)—[3-CH₃, 4-F—C₆H₃] | (E) |
| A.741 | CH=C(CH₃)—[2-Cl, 4-CH₃—C₆H₃] | (E) |
| A.742 | CH=C(CH₃)—[2-CH₃, 4-Cl—C₆H₃] | (E) |
| A.743 | CH=C(CH₃)—[3-Cl, 4-CH₃—C₆H₃] | (E) |

TABLE A-continued

| No. | R² | |
|---|---|---|
| A.744 | CH=C(CH₃)—[3-CH₃, 4-Cl—C₆H₃] | (E) |
| A.745 | CH=C(CH₃)—[2,4-(CH₃)₂—C₆H₃] | (E) |
| A.746 | CH=C(CH₃)—[3,4-(CH₃)₂—C₆H₃] | (E) |
| A.747 | CH=C(CH₃)—[2,4,5-(CH₃)₃—C₆H₂] | (E) |
| A.748 | CH=C(CH₃)—[2,4,6-(CH₃)₃—C₆H₂] | (E) |
| A.749 | CH=C(CH₃)—[2-CF₃—C₆H₄] | (E) |
| A.750 | CH=C(CH₃)—[3-CF₃—C₆H₄] | (E) |
| A.751 | CH=C(CH₃)—[4-CF₃—C₆H₄] | (E) |
| A.752 | CH=C(CH₃)—[2-F, 4-CF₃—C₆H₃] | (E) |
| A.753 | CH=C(CH₃)—[2-CF₃, 4-F—C₆H₃] | (E) |
| A.754 | CH=C(CH₃)—[3-F, 4-CF₃—C₆H₃] | (E) |
| A.755 | CH=C(CH₃)—[3-CF₃, 4-F—C₆H₃] | (E) |
| A.756 | CH=C(CH₃)—[2-Cl, 4-CF₃—C₆H₃] | (E) |
| A.757 | CH=C(CH₃)—[2-CF₃, 4-Cl—C₆H₃] | (E) |
| A.758 | CH=C(CH₃)—[3-Cl, 4-CF₃—C₆H₃] | (E) |
| A.759 | CH=C(CH₃)—[3-CF₃, 4-Cl—C₆H₃] | (E) |
| A.760 | CH=C(CH₃)—[2,4-(CF₃)₂—C₆H₃] | (E) |
| A.761 | CH=C(CH₃)—[3,4-(CF₃)₂—C₆H₃] | (E) |
| A.762 | CH=C(CH₃)—[2,4,5-(CF₃)₃—C₆H₂] | (E) |
| A.763 | CH=C(CH₃)—[2,4,6-(CF₃)₃—C₆H₂] | (E) |
| A.764 | CH=C(CH₃)—[2-OCH₃—C₆H₄] | (E) |
| A.765 | CH=C(CH₃)—[3-OCH₃—C₆H₄] | (E) |
| A.766 | CH=C(CH₃)—[4-OCH₃—C₆H₄] | (E) |
| A.767 | CH=C(CH₃)—[2-F, 4-OCH₃—C₆H₃] | (E) |
| A.768 | CH=C(CH₃)—[2-OCH₃, 4-F—C₆H₃] | (E) |
| A.769 | CH=C(CH₃)—[3-F, 4-OCH₃—C₆H₃] | (E) |
| A.770 | CH=C(CH₃)—[3-OCH₃, 4-F—C₆H₃] | (E) |
| A.771 | CH=C(CH₃)—[2-Cl, 4-OCH₃—C₆H₃] | (E) |
| A.772 | CH=C(CH₃)—[2-OCH₃, 4-Cl—C₆H₃] | (E) |
| A.773 | CH=C(CH₃)—[3-Cl, 4-OCH₃—C₆H₃] | (E) |
| A.774 | CH=C(CH₃)—[3-OCH₃, 4-Cl—C₆H₃] | (E) |
| A.775 | CH=C(CH₃)—[2,4-(OCH₃)₂—C₆H₃] | (E) |
| A.776 | CH=C(CH₃)—[3,4-(OCH₃)₂—C₆H₃] | (E) |
| A.777 | CH=C(CH₃)—[2,4,5-(OCH₃)₃—C₆H₂] | (E) |
| A.778 | CH=C(CH₃)—[2,4,6-(OCH₃)₃—C₆H₂] | (E) |
| A.779 | CH=C(CH₃)—[2-OCHF₂—C₆H₄] | (E) |
| A.780 | CH=C(CH₃)—[3-OCHF₂—C₆H₄] | (E) |
| A.781 | CH=C(CH₃)—[4-OCHF₂—C₆H₄] | (E) |
| A.782 | CH=C(CH₃)—[2-F, 4-OCHF₂—C₆H₃] | (E) |
| A.783 | CH=C(CH₃)—[2-OCHF₂, 4-F—C₆H₃] | (E) |
| A.784 | CH=C(CH₃)—[3-F, 4-OCHF₂—C₆H₃] | (E) |
| A.785 | CH=C(CH₃)—[3-OCHF₂, 4-F—C₆H₃] | (E) |
| A.786 | CH=C(CH₃)—[2-Cl, 4-OCHF₂—C₆H₃] | (E) |
| A.787 | CH=C(CH₃)—[2-OCHF₂, 4-Cl—C₆H₃] | (E) |
| A.788 | CH=C(CH₃)—[3-Cl, 4-OCHF₂—C₆H₃] | (E) |
| A.789 | CH=C(CH₃)—[3-OCHF₂, 4-Cl—C₆H₃] | (E) |
| A.790 | CH=C(CH₃)—[2,4-(OCHF₂)₂—C₆H₃] | (E) |
| A.791 | CH=C(CH₃)—[3,4-(OCHF₂)₂—C₆H₃] | (E) |
| A.792 | CH=C(CH₃)—[2,4,5-(OCHF₂)₃—C₆H₂] | (E) |
| A.793 | CH=C(CH₃)—[2,4,6-(OCHF₂)₃—C₆H₂] | (E) |
| A.794 | C≡C—I | |
| A.795 | CH₂—C≡C—H | |
| A.796 | CH₂—C≡C—Cl | |
| A.797 | CH₂—C≡C—Br | |
| A.798 | CH₂—C≡C—I | |
| A.799 | CH₂—C≡C—CH₃ | |
| A.800 | CH₂—C≡C—CH₂CH₃ | |
| A.801 | CH₂CH₂—C≡C—H | |
| A.802 | CH₂CH₂—C≡C—Cl | |
| A.803 | CH₂CH₂—C≡C—Br | |
| A.804 | CH₂CH₂—C≡C—I | |
| A.805 | CH₂CH₂—C≡C—CH₃ | |
| A.806 | CH₂CH₂CH₂—C≡C—H | |
| A.807 | CH₂CH₂CH₂—C≡C—Cl | |
| A.808 | CH₂CH₂CH₂—C≡C—Br | |
| A.809 | CH₂CH₂CH₂—C≡C—I | |
| A.810 | CH₂CH₂CH₂—C≡C—CH₃ | |
| A.811 | CH(CH₃)—C≡C—H | |
| A.812 | CH(CH₃)—C≡C—Cl | |
| A.813 | CH(CH₃)—C≡C—Br | |
| A.814 | CH(CH₃)—C≡C—I | |
| A.815 | CH(CH₃)—C≡C—CH₃ | |
| A.816 | C≡C—[4-F—C₆H₄] | |

TABLE B

| No. | R² | |
|---|---|---|
| B.1 | CH₂CH₃ | |
| B.2 | CH₂CH₂—CN | |
| B.3 | CH₂CH₂—O—CH₃ | |
| B.4 | CH₂CH₂—O—CH₂CH₃ | |
| B.5 | CH₂CH₂CH₃ | |
| B.6 | CH(CH₃)₂ | |
| B.7 | CH₂CH₂CH₂CH₃ | |
| B.8 | CH(CH₃)CH₂CH₃ | |
| B.9 | CH₂CH(CH₃)₂ | |
| B.10 | CH=CH₂ | |
| B.11 | CH=CH—CH₃ | (E) |
| B.12 | CH=CH—[C₆H₅] | (E) |
| B.13 | CH=CH—[2-CN—C₆H₄] | (E) |
| B.14 | CH=CH—[3-CN—C₆H₄] | (E) |
| B.15 | CH=CH—[4-CN—C₆H₄] | (E) |
| B.16 | CH=CH—[2-F—C₆H₄] | (E) |
| B.17 | CH=CH—[3-F—C₆H₄] | (E) |
| B.18 | CH=CH—[4-F—C₆H₄] | (E) |
| B.19 | CH=CH—[2,4-F₂—C₆H₃] | (E) |
| B.20 | CH=CH—[3,4-F₂—C₆H₃] | (E) |
| B.21 | CH=CH—[2,4,5-F₃—C₆H₂] | (E) |
| B.22 | CH=CH—[2,4,6-F₃—C₆H₂] | (E) |
| B.23 | CH=CH—[2-Cl—C₆H₄] | (E) |
| B.24 | CH=CH—[3-Cl—C₆H₄] | (E) |
| B.25 | CH=CH—[4-Cl—C₆H₄] | (E) |
| B.26 | CH=CH—[2,4-Cl₂—C₆H₃] | (E) |
| B.27 | CH=CH—[3,4-Cl₂—C₆H₃] | (E) |
| B.28 | CH=CH—[2,4,5-Cl₃—C₆H₂] | (E) |
| B.29 | CH=CH—[2,4,6-Cl₃—C₆H₂] | (E) |
| B.30 | CH=CH—[2-CH₃—C₆H₄] | (E) |
| B.31 | CH=CH—[3-CH₃—C₆H₄] | (E) |
| B.32 | CH=CH—[4-CH₃—C₆H₄] | (E) |
| B.33 | CH=CH—[2-F, 4-CH₃—C₆H₃] | (E) |
| B.34 | CH=CH—[2-CH₃, 4-F—C₆H₃] | (E) |
| B.35 | CH=CH—[3-F, 4-CH₃—C₆H₃] | (E) |
| B.36 | CH=CH—[3-CH₃, 4-F—C₆H₃] | (E) |
| B.37 | CH=CH—[2-Cl, 4-CH₃—C₆H₃] | (E) |
| B.38 | CH=CH—[2-CH₃, 4-Cl—C₆H₃] | (E) |
| B.39 | CH=CH—[3-Cl, 4-CH₃—C₆H₃] | (E) |
| B.40 | CH=CH—[3-CH₃, 4-Cl—C₆H₃] | (E) |
| B.41 | CH=CH—[2-CF₃—C₆H₄] | (E) |
| B.42 | CH=CH—[3-CF₃—C₆H₄] | (E) |
| B.43 | CH=CH—[4-CF₃—C₆H₄] | (E) |
| B.44 | CH=CH—[2-OCH₃—C₆H₄] | (E) |
| B.45 | CH=CH—[3-OCH₃—C₆H₄] | (E) |
| B.46 | CH=CH—[4-OCH₃—C₆H₄] | (E) |
| B.47 | CH=CH—[2-OCHF₂—C₆H₄] | (E) |
| B.48 | CH=CH—[3-OCHF₂—C₆H₄] | (E) |
| B.49 | CH=CH—[4-OCHF₂—C₆H₄] | (E) |
| B.50 | CH₂CH=CH₂ | |
| B.51 | CH₂CH=CH—Cl | (E) |
| B.52 | CH₂CH=CH—CH₃ | (E) |
| B.53 | C≡CH | |
| B.54 | C≡C—Cl | |
| B.55 | C≡C—Br | |
| B.56 | C≡C—CH₃ | |
| B.57 | C≡C—C₆H₅ | |
| B.58 | C≡C—[2-Cl—C₆H₄] | |
| B.59 | C≡C—[4-Cl—C₆H₄] | |
| B.60 | C≡C—[2,4-Cl₂—C₆H₃] | |
| B.61 | C≡C—[2-CH₃—C₆H₄] | |
| B.62 | C≡C—[4-CH₃—C₆H₄] | |
| B.63 | C≡C—[2,4-(CH₃)₂—C₆H₃] | |
| B.64 | C≡C—[2-Cl, 4-CH₃—C₆H₃] | |
| B.65 | C≡C—[2-CH₃, 4-Cl—C₆H₃] | |
| B.66 | C≡C—[3-CF₃—C₆H₄] | |
| B.67 | C≡C—[3-Cl, 5-CF₃—C₆H₃] | |
| B.68 | C≡C—[2-OCH₃—C₆H₄] | |
| B.69 | C≡C—[4-OCH₃—C₆H₄] | |
| B.70 | C≡C—[2,4-(OCH₃)₂—C₆H₃] | |
| B.71 | C≡C—[2-Cl, 4-OCH₃—C₆H₃] | |
| B.72 | C≡C—[2-OCH₃, 4-Cl—C₆H₃] | |
| B.73 | C≡C—[3-OCHF₂—C₆H₄] | |
| B.74 | C≡C—[3-Cl, 5-OCHF₂—C₆H₃] | |
| B.75 | cyclopentyl | |
| B.76 | 1-CH₃-cyclopentyl | |
| B.77 | 2-CH₃-cyclopentyl | |

TABLE B-continued

| No. | R² |
|---|---|
| B.78 | 3-CH₃-cyclopentyl |
| B.79 | 2,3-(CH₃)₂-cyclopentyl |
| B.80 | 1-Cl-cyclopentyl |
| B.81 | 2-Cl-cyclopentyl |
| B.82 | 3-Cl-cyclopentyl |
| B.83 | 2-CH₃, 3-Cl-cyclopentyl |
| B.84 | 2,3-Cl₂-cyclopentyl |
| B.85 | cyclohexyl |
| B.86 | 1-CH₃-cyclohexyl |
| B.87 | 2-CH₃-cyclohexyl |
| B.88 | 3-CH₃-cyclohexyl |
| B.89 | 2,3-(CH₃)₂-cyclohexyl |
| B.90 | 3,3-(CH₃)₂-cyclohexyl |
| B.91 | 1-Cl-cyclohexyl |
| B.92 | 2-Cl-cyclohexyl |
| B.93 | 3-Cl-cyclohexyl |
| B.94 | 2-CH₃, 3-Cl-cyclohexyl |
| B.95 | 2,3-Cl₂-cyclohexyl |
| B.96 | C₆H₅ |
| B.97 | 2-CN—C₆H₄ |
| B.98 | 3-CN—C₆H₄ |
| B.99 | 4-CN—C₆H₄ |
| B.100 | 2-F—C₆H₄ |
| B.101 | 3-F—C₆H₄ |
| B.102 | 4-F—C₆H₄ |
| B.103 | 2,4-F₂—C₆H₃ |
| B.104 | 3,4-F₂—C₆H₃ |
| B.105 | 2,4,5-F₃—C₆H₂ |
| B.106 | 2,4,6-F₃—C₆H₂ |
| B.107 | 2-Cl—C₆H₄ |
| B.108 | 3-Cl—C₆H₄ |
| B.109 | 4-Cl—C₆H₄ |
| B.110 | 2,4-Cl₂—C₆H₃ |
| B.111 | 3,4-Cl₂—C₆H₃ |
| B.112 | 2,4,5-Cl₃—C₆H₂ |
| B.113 | 2,4,6-Cl₃—C₆H₂ |
| B.114 | 2-CH₃—C₆H₄ |
| B.115 | 3-CH₃—C₆H₄ |
| B.116 | 4-CH₃—C₆H₄ |
| B.117 | 2-F, 4-CH₃—C₆H₃ |
| B.118 | 2-CH₃, 4-F—C₆H₃ |
| B.119 | 3-F, 4-CH₃—C₆H₃ |
| B.120 | 3-CH₃, 4-F—C₆H₃ |
| B.121 | 2-Cl, 4-CH₃—C₆H₃ |
| B.122 | 2-CH₃, 4-Cl—C₆H₃ |
| B.123 | 3-Cl, 4-CH₃—C₆H₃ |
| B.124 | 3-CH₃, 4-Cl—C₆H₃ |
| B.125 | 2,4-(CH₃)₂—C₆H₃ |
| B.126 | 3,4-(CH₃)₂—C₆H₃ |
| B.127 | 2,4,5-(CH₃)₃—C₆H₂ |
| B.128 | 2,4,6-(CH₃)₃—C₆H₂ |
| B.129 | 2-CF₃—C₆H₄ |
| B.130 | 3-CF₃—C₆H₄ |
| B.131 | 4-CF₃—C₆H₄ |
| B.132 | 2-F, 4-CF₃—C₆H₃ |
| B.133 | 2-CF₃, 4-F—C₆H₃ |
| B.134 | 3-F, 4-CF₃—C₆H₃ |
| B.135 | 3-CF₃, 4-F—C₆H₃ |
| B.136 | 2-Cl, 4-CF₃—C₆H₃ |
| B.137 | 2-CF₃, 4-Cl—C₆H₃ |
| B.138 | 3-Cl, 4-CF₃—C₆H₃ |
| B.139 | 3-CF₃, 4-Cl—C₆H₃ |
| B.140 | 2,4-(CF₃)₂—C₆H₃ |
| B.141 | 3,4-(CF₃)₂—C₆H₃ |
| B.142 | 2,4,5-(CF₃)₃—C₆H₂ |
| B.143 | 2,4,6-(CF₃)₃—C₆H₂ |
| B.144 | 2-OCH₃—C₆H₄ |
| B.145 | 3-OCH₃—C₆H₄ |
| B.146 | 4-OCH₃—C₆H₄ |
| B.147 | 2-F, 4-OCH₃—C₆H₃ |
| B.148 | 2-OCH₃, 4-F—C₆H₃ |
| B.149 | 3-F, 4-OCH₃—C₆H₃ |
| B.150 | 3-OCH₃, 4-F—C₆H₃ |
| B.151 | 2-Cl, 4-OCH₃—C₆H₃ |
| B.152 | 2-OCH₃, 4-Cl—C₆H₃ |
| B.153 | 3-Cl, 4-OCH₃—C₆H₃ |
| B.154 | 3-OCH₃, 4-Cl—C₆H₃ |
| B.155 | 2,4-(OCH₃)₂—C₆H₃ |
| B.156 | 3,4-(OCH₃)₂—C₆H₃ |
| B.157 | 2,4,5-(OCH₃)₃—C₆H₂ |
| B.158 | 2,4,6-(OCH₃)₃—C₆H₂ |
| B.159 | 2-OCHF₂—C₆H₄ |
| B.160 | 3-OCHF₂—C₆H₄ |
| B.161 | 4-OCHF₂—C₆H₄ |
| B.162 | 2-F, 4-OCHF₂—C₆H₃ |
| B.163 | 2-OCHF₂, 4-F—C₆H₃ |
| B.164 | 3-F, 4-OCHF₂—C₆H₃ |
| B.165 | 3-OCHF₂, 4-F—C₆H₃ |
| B.166 | 2-Cl, 4-OCHF₂—C₆H₃ |
| B.167 | 2-OCHF₂, 4-Cl—C₆H₃ |
| B.168 | 3-Cl, 4-OCHF₂—C₆H₃ |
| B.169 | 3-OCHF₂, 4-Cl—C₆H₃ |
| B.170 | 2,4-(OCHF₂)₂—C₆H₃ |
| B.171 | 3,4-(OCHF₂)₂—C₆H₃ |
| B.172 | 2,4,5-(OCHF₂)₃—C₆H₂ |
| B.173 | 2,4,6-(OCHF₂)₃—C₆H₂ |
| B.174 | CH₂—C₆H₅ |
| B.175 | CH₂—[2-CN—C₆H₄] |
| B.176 | CH₂—[3-CN—C₆H₄] |
| B.177 | CH₂—[4-CN—C₆H₄] |
| B.178 | CH₂—[2-F—C₆H₄] |
| B.179 | CH₂—[3-F—C₆H₄] |
| B.180 | CH₂—[4-F—C₆H₄] |
| B.181 | CH₂—[2,4-F₂—C₆H₃] |
| B.182 | CH₂—[3,4-F₂—C₆H₃] |
| B.183 | CH₂—[2,4,5-F₃—C₆H₂] |
| B.184 | CH₂—[2,4,6-F₃—C₆H₂] |
| B.185 | CH₂—[2-Cl—C₆H₄] |
| B.186 | CH₂—[3-Cl—C₆H₄] |
| B.187 | CH₂—[4-Cl—C₆H₄] |
| B.188 | CH₂—[2,4-Cl₂—C₆H₃] |
| B.189 | CH₂—[3,4-Cl₂—C₆H₃] |
| B.190 | CH₂—[2,4,5-Cl₃—C₆H₂] |
| B.191 | CH₂—[2,4,6-Cl₃—C₆H₂] |
| B.192 | CH₂—[2-CH₃—C₆H₄] |
| B.193 | CH₂—[3-CH₃—C₆H₄] |
| B.194 | CH₂—[4-CH₃—C₆H₄] |
| B.195 | CH₂—[2-F, 4-CH₃—C₆H₃] |
| B.196 | CH₂—[2-CH₃, 4-F—C₆H₃] |
| B.197 | CH₂—[3-F, 4-CH₃—C₆H₃] |
| B.198 | CH₂—[3-CH₃, 4-F—C₆H₃] |
| B.199 | CH₂—[2-Cl, 4-CH₃—C₆H₃] |
| B.200 | CH₂—[2-CH₃, 4-Cl—C₆H₃] |
| B.201 | CH₂—[3-Cl, 4-CH₃—C₆H₃] |
| B.202 | CH₂—[3-CH₃, 4-Cl—C₆H₃] |
| B.203 | CH₂—[2-CF₃—C₆H₄] |
| B.204 | CH₂—[3-CF₃—C₆H₄] |
| B.205 | CH₂—[4-CF₃—C₆H₄] |
| B.206 | CH₂—[2-OCH₃—C₆H₄] |
| B.207 | CH₂—[3-OCH₃—C₆H₄] |
| B.208 | CH₂—[4-OCH₃—C₆H₄] |
| B.209 | CH₂—[2-OCHF₂—C₆H₄] |
| B.210 | CH₂—[3-OCHF₂—C₆H₄] |
| B.211 | CH₂—[4-OCHF₂—C₆H₄] |
| B.212 | CH(CH₃)—C₆H₅ |
| B.213 | CH(CH₃)—[2-CN—C₆H₄] |
| B.214 | CH(CH₃)—[3-CN—C₆H₄] |
| B.215 | CH(CH₃)—[4-CN—C₆H₄] |
| B.216 | CH(CH₃)—[2-F—C₆H₄] |
| B.217 | CH(CH₃)—[3-F—C₆H₄] |
| B.218 | CH(CH₃)—[4-F—C₆H₄] |
| B.219 | CH(CH₃)—[2,4-F₂—C₆H₃] |
| B.220 | CH(CH₃)—[3,4-F₂—C₆H₃] |
| B.221 | CH(CH₃)—[2,4,5-F₃—C₆H₂] |
| B.222 | CH(CH₃)—[2,4,6-F₃—C₆H₂] |
| B.223 | CH(CH₃)—[2-Cl—C₆H₄] |
| B.224 | CH(CH₃)—[3-Cl—C₆H₄] |
| B.225 | CH(CH₃)—[4-Cl—C₆H₄] |
| B.226 | CH(CH₃)—[2,4-Cl₂—C₆H₃] |
| B.227 | CH(CH₃)—[3,4-Cl₂—C₆H₃] |
| B.228 | CH(CH₃)—[2,4,5-Cl₃—C₆H₂] |
| B.229 | CH(CH₃)—[2,4,6-Cl₃—C₆H₂] |
| B.230 | CH(CH₃)—[2-CH₃—C₆H₄] |
| B.231 | CH(CH₃)—[3-CH₃—C₆H₄] |

TABLE B-continued

| No. | R² | |
|---|---|---|
| B.232 | CH(CH₃)—[4-CH₃—C₆H₄] | |
| B.233 | CH(CH₃)—[2-F, 4-CH₃—C₆H₃] | |
| B.234 | CH(CH₃)—[2-CH₃, 4-F—C₆H₃] | |
| B.235 | CH(CH₃)—[3-F, 4-CH₃—C₆H₃] | |
| B.236 | CH(CH₃)—[3-CH₃, 4-F—C₆H₃] | |
| B.237 | CH(CH₃)—[2-Cl, 4-CH₃—C₆H₃] | |
| B.238 | CH(CH₃)—[2-CH₃, 4-Cl—C₆H₃] | |
| B.239 | CH(CH₃)—[3-Cl, 4-CH₃—C₆H₃] | |
| B.240 | CH(CH₃)—[3-CH₃, 4-Cl—C₆H₃] | |
| B.241 | CH(CH₃)—[2-CF₃—C₆H₄] | |
| B.242 | CH(CH₃)—[3-CF₃—C₆H₄] | |
| B.243 | CH(CH₃)—[4-CF₃—C₆H₄] | |
| B.244 | CH(CH₃)—[2-OCH₃—C₆H₄] | |
| B.245 | CH(CH₃)—[3-OCH₃—C₆H₄] | |
| B.246 | CH(CH₃)—[4-OCH₃—C₆H₄] | |
| B.247 | CH(CH₃)—[2-OCHF₂—C₆H₄] | |
| B.248 | CH(CH₃)—[3-OCHF₂—C₆H₄] | |
| B.249 | CH(CH₃)—[4-OCHF₂—C₆H₄] | |
| B.250 | CH₂F | |
| B.251 | CHF₂ | |
| B.252 | CF₃ | |
| B.253 | CH₂—CN | |
| B.254 | CH₂—OCH₃ | |
| B.255 | CH₂—OCH₂CH₃ | |
| B.256 | CH₂—OCH₂CH₂CH₃ | |
| B.257 | CH₂—OCH(CH₃)₂ | |
| B.258 | CH₂—OCH₂CH₂CH₂CH₃ | |
| B.259 | CH₂—OCH(CH₃)CH₂CH₃ | |
| B.260 | CH₂—OCH₂CH(CH₃)₂ | |
| B.261 | CH₂—OC(CH₃)₃ | |
| B.262 | CH₂—OCF₃ | |
| B.263 | CH₂—OCH₂CF₃ | |
| B.264 | CH₂CH₂—OCH₂CH₂CH₃ | |
| B.265 | CH₂CH₂—OCH(CH₃)₂ | |
| B.266 | CH₂CH₂—OCH₂CH₂CH₂CH₃ | |
| B.267 | CH₂CH₂—OCH(CH₃)CH₂CH₃ | |
| B.268 | CH₂CH₂—OCH₂CH(CH₃)₂ | |
| B.269 | CH₂CH₂—OC(CH₃)₃ | |
| B.270 | CH₂CH₂—OCF₃ | |
| B.271 | CH₂CH₂—OCH₂CF₃ | |
| B.272 | CH₂CH₂—[C₆H₅] | |
| B.273 | CH₂CH₂—[2-CN—C₆H₄] | |
| B.274 | CH₂CH₂—[3-CN—C₆H₄] | |
| B.275 | CH₂CH₂—[4-CN—C₆H₄] | |
| B.276 | CH₂CH₂—[2-F—C₆H₄] | |
| B.277 | CH₂CH₂—[3-F—C₆H₄] | |
| B.278 | CH₂CH₂—[4-F—C₆H₄] | |
| B.279 | CH₂CH₂—[2,4-F₂—C₆H₃] | |
| B.280 | CH₂CH₂—[3,4-F₂—C₆H₃] | |
| B.281 | CH₂CH₂—[2,4,5-F₃—C₆H₂] | |
| B.282 | CH₂CH₂—[2,4,6-F₃—C₆H₂] | |
| B.283 | CH₂CH₂—[2-Cl—C₆H₄] | |
| B.284 | CH₂CH₂—[3-Cl—C₆H₄] | |
| B.285 | CH₂CH₂—[4-Cl—C₆H₄] | |
| B.286 | CH₂CH₂—[2,4-Cl₂—C₆H₃] | |
| B.287 | CH₂CH₂—[3,4-Cl₂—C₆H₃] | |
| B.288 | CH₂CH₂—[2,4,5-Cl₃—C₆H₂] | |
| B.289 | CH₂CH₂—[2,4,6-Cl₃—C₆H₂] | |
| B.290 | CH₂CH₂—[2-CH₃—C₆H₄] | |
| B.291 | CH₂CH₂—[3-CH₃—C₆H₄] | |
| B.292 | CH₂CH₂—[4-CH₃—C₆H₄] | |
| B.293 | CH₂CH₂—[2-F, 4-CH₃—C₆H₃] | |
| B.294 | CH₂CH₂—[2-CH₃, 4-F—C₆H₃] | |
| B.295 | CH₂CH₂—[3-F, 4-CH₃—C₆H₃] | |
| B.296 | CH₂CH₂—[3-CH₃, 4-F—C₆H₃] | |
| B.297 | CH₂CH₂—[2-Cl, 4-CH₃—C₆H₃] | |
| B.298 | CH₂CH₂—[2-CH₃, 4-Cl—C₆H₃] | |
| B.299 | CH₂CH₂—[3-Cl, 4-CH₃—C₆H₃] | |
| B.300 | CH₂CH₂—[3-CH₃, 4-Cl—C₆H₃] | |
| B.301 | CH₂CH₂—[2-CF₃—C₆H₄] | |
| B.302 | CH₂CH₂—[3-CF₃—C₆H₄] | |
| B.303 | CH₂CH₂—[4-CF₃—C₆H₄] | |
| B.304 | CH₂CH₂—[2-OCH₃—C₆H₄] | |
| B.305 | CH₂CH₂—[3-OCH₃—C₆H₄] | |
| B.306 | CH₂CH₂—[4-OCH₃—C₆H₄] | |
| B.307 | CH₂CH₂—[2-OCHF₂—C₆H₄] | |
| B.308 | CH₂CH₂—[3-OCHF₂—C₆H₄] | |
| B.309 | CH₂CH₂—[4-OCHF₂—C₆H₄] | |
| B.310 | CH(CH₃)—CN | |
| B.311 | CH(CH₃)—OCH₃ | |
| B.312 | CH(CH₃)—OCH₂CH₃ | |
| B.313 | CH(CH₃)—OCH₂CH₂CH₃ | |
| B.314 | CH(CH₃)—OCH(CH₃)₂ | |
| B.315 | CH(CH₃)—OCH₂CH₂CH₂CH₃ | |
| B.316 | CH(CH₃)—OCH(CH₃)CH₂CH₃ | |
| B.317 | CH(CH₃)—OCH₂CH(CH₃)₂ | |
| B.318 | CH(CH₃)—OC(CH₃)₃ | |
| B.319 | CH(CH₃)—OCF₃ | |
| B.320 | CH(CH₃)—OCH₂CF₃ | |
| B.321 | CH₂CH₂F | |
| B.322 | CH₂CHF₂ | |
| B.323 | CH₂CF₃ | |
| B.324 | CHFCH₃ | |
| B.325 | CF₂CH₃ | |
| B.326 | CHFCHF₂ | |
| B.327 | CHFCF₃ | |
| B.328 | CF₂CHF₂ | |
| B.329 | CF₂CF₃ | |
| B.330 | CF₂CHFCl | |
| B.331 | CH₂CH₂CH₂—CN | |
| B.332 | CH₂CH₂CH₂—OCH₃ | |
| B.333 | CH₂CH₂CH₂—OCH₂CH₃ | |
| B.334 | CH₂CH₂CH₂—OCH₂CH₂CH₃ | |
| B.335 | CH₂CH₂CH₂—OCH(CH₃)₂ | |
| B.336 | CH₂CH₂CH₂—OCF₃ | |
| B.337 | CH₂CH₂CH₂—OCH₂CF₃ | |
| B.338 | CH₂CH(CH₃)—CN | |
| B.339 | CH₂CH(CH₃)—OCH₃ | |
| B.340 | CH₂CH(CH₃)—OCH₂CH₃ | |
| B.341 | CH₂CH(CH₃)—OCH₂CH₂CH₃ | |
| B.342 | CH₂CH(CH₃)—OCH(CH₃)₂ | |
| B.343 | CH₂CH(CH₃)—OCF₃ | |
| B.344 | CH₂CH(CH₃)—OCH₂CF₃ | |
| B.345 | CH(CH₂CH₃)—CN | |
| B.346 | CH(CH₂CH₃)—OCH₃ | |
| B.347 | CH(CH₂CH₃)—OCH₂CH₃ | |
| B.348 | CH(CH₂CH₃)—OCH₂CH₂CH₃ | |
| B.349 | CH(CH₂CH₃)—OCH(CH₃)₂ | |
| B.350 | CH(CH₂CH₃)—OCF₃ | |
| B.351 | CH(CH₂CH₃)—OCH₂CF₃ | |
| B.352 | CH(CH₃)CH₂—CN | |
| B.353 | CH(CH₃)CH₂—OCH₃ | |
| B.354 | CH(CH₃)CH₂—OCH₂CH₃ | |
| B.355 | CH(CH₃)CH₂—OCH₂CH₂CH₃ | |
| B.356 | CH(CH₃)CH₂—OCH(CH₃)₂ | |
| B.357 | CH(CH₃)CH₂—OCF₃ | |
| B.358 | CH(CH₃)CH₂—OCH₂CF₃ | |
| B.359 | CH₂CH₂CF₃ | |
| B.360 | CH₂CF₃CF₃ | |
| B.361 | CHFCH₂CH₃ | |
| B.362 | CH(CF₃)CH₃ | |
| B.363 | CH(CF₃)₂ | |
| B.364 | CH₂CH₂CH₂CH₂—CN | |
| B.365 | CH₂CH₂CH₂CH₂—OCH₃ | |
| B.366 | CH₂CH₂CH₂CH₂—OCH₂CH₃ | |
| B.367 | CH₂CH₂CH₂CH₂—OCF₃ | |
| B.368 | CH(CN)—CH₂CH₂CH₃ | |
| B.369 | CH(OCH₃)—CH₂CH₂CH₃ | |
| B.370 | CH(OCH₂CH₃)—CH₂CH₂CH₃ | |
| B.371 | CH(OCF₃)—CH₂CH₂CH₃ | |
| B.372 | CH(OCH₂CF₃)—CH₂CH₂CH₃ | |
| B.373 | CH(CN)—CH₂CH(CH₃)₂ | |
| B.374 | CH(OCH₃)—CH₂CH(CH₃)₂ | |
| B.375 | CH(OCH₂CH₃)—CH₂CH(CH₃)₂ | |
| B.376 | CH(OCF₃)—CH₂CH(CH₃)₂ | |
| B.377 | CH(OCH₂CF₃)—CH₂CH(CH₃)₂ | |
| B.378 | CHFCH₂CH₂CH₃ | |
| B.379 | C(CH₃)=CH₂ | |
| B.380 | CH=CH—CH₃ | (Z) |
| B.381 | C(CH₂CH₃)=CH₂ | |
| B.382 | C(CH₃)=CH—CH₃ | (E) |
| B.383 | C(CH₃)=CH—CH₃ | (Z) |
| B.384 | C(CH₃)=C(CH₃)₂ | |
| B.385 | CH(CH₃)—CH=CH₂ | |

TABLE B-continued

| No. | R² | |
|---|---|---|
| B.386 | CH=C(CH₃)₂ | |
| B.387 | CH₂—C(CH₃)=CH₂ | |
| B.388 | CH(CH₃)—CH₂—CH=CH₂ | |
| B.389 | CH₂—CH(CH₃)—CH=CH₂ | |
| B.390 | CH₂—CCl=CH₂ | |
| B.391 | CH₂—CH=CH—Cl | (Z) |
| B.392 | CH₂—CCl=CH—Cl | (E) |
| B.393 | CH₂—CCl=CH—Cl | (Z) |
| B.394 | CH₂—CH=CCl₂ | |
| B.395 | CH₂—CCl=CCl₂ | |
| B.396 | CH₂—CBr=CH₂ | |
| B.397 | CH₂—CH=CH—Br | (Z) |
| B.398 | CH₂—CBr=CH—Br | (E) |
| B.399 | CH₂—CBr=CH—Br | (Z) |
| B.400 | CH₂—CH=CBr₂ | |
| B.401 | CH₂—CBr=CBr₂ | |
| B.402 | CH₂—CH=CH—CH₃ | (Z) |
| B.403 | CH₂—C(CH₃)=CH—CH₃ | (E) |
| B.404 | CH₂—C(CH₃)=CH—CH₃ | (Z) |
| B.405 | CH₂—CH=C(CH₃)₂ | |
| B.406 | CH₂—CH—CH=CH₂ | |
| B.407 | CH₂—CCl=CH—CH₃ | (E) |
| B.408 | CH₂—CCl=CH—CH₃ | (Z) |
| B.409 | CH₂—CH=CCl—CH₃ | (E) |
| B.410 | CH₂—CH=CCl—CH₃ | (Z) |
| B.411 | CH₂—C(CH₃)=C(CH₃)₂ | |
| B.412 | CH₂—CBr=CH—CH₃ | (E) |
| B.413 | CH₂—CBr=CH—CH₃ | (Z) |
| B.414 | CH₂—CH=CBr—CH₃ | (E) |
| B.415 | CH₂—CH=CBr—CH₃ | (Z) |
| B.416 | CH₂—CH=CH—CH₂Cl | (E) |
| B.417 | CH₂—CH=CH—CH₂Cl | (Z) |
| B.418 | CH₂—CH=CH—CH₂CH₃ | (E) |
| B.419 | CH₂—CH=CH—CH₂CH₃ | (Z) |
| B.420 | CH₂—CH=CH—CH₂Br | (E) |
| B.421 | CH₂—CH=CH—CH₂Br | (Z) |
| B.422 | CH₂—CCl=CCl—CH₂Cl | (E) |
| B.423 | CH₂—CCl=CCl—CH₂Cl | (Z) |
| B.424 | CH₂—CF=CH₂ | |
| B.425 | CH₂—CH=CH—F | (E) |
| B.426 | CH₂—CH=CH—F | (Z) |
| B.427 | CH₂—CH=CF₂ | |
| B.428 | CH₂—CF=CH—F | (E) |
| B.429 | CH₂—CF=CH—F | (Z) |
| B.430 | CH(CH₃)—CH=CH₂ | |
| B.431 | CH(CH₃)—CCl=CH₂ | |
| B.432 | CH(CH₃)—CH=CH—Cl | (E) |
| B.433 | CH(CH₃)—CH=CH—Cl | (Z) |
| B.434 | CH(CH₃)—CCl=CH—Cl | (E) |
| B.435 | CH(CH₃)—CCl=CH—Cl | (Z) |
| B.436 | CH(CH₃)—CH=CCl₂ | |
| B.437 | CH(CH₃)—CCl=CCl₂ | |
| B.438 | CH(CH₃)—CBr=CH₂ | |
| B.439 | CH(CH₃)—CH=CH—Br | (E) |
| B.440 | CH(CH₃)—CH=CH—Br | (Z) |
| B.441 | CH(CH₃)—CBr=CH—Br | (E) |
| B.442 | CH(CH₃)—CBr=CH—Br | (Z) |
| B.443 | CH(CH₃)—CH=CBr₂ | |
| B.444 | CH(CH₃)—CBr=CBr₂ | |
| B.445 | CH(CH₃)—C(CH₃)=CH₂ | |
| B.446 | CH(CH₃)—CH=CH—CH₃ | (E) |
| B.447 | CH(CH₃)—CH=CH—CH₃ | (Z) |
| B.448 | CH(CH₃)—C(CH₃)=CH—CH₃ | (E) |
| B.449 | CH(CH₃)—C(CH₃)=CH—CH₃ | (Z) |
| B.450 | CH(CH₃)—CH=C(CH₃)₂ | |
| B.451 | CH(CH₃)—CCl=CH—CH₃ | (E) |
| B.452 | CH(CH₃)—CCl=CH—CH₃ | (Z) |
| B.453 | CH(CH₃)—CH=CCl—CH₃ | (E) |
| B.454 | CH(CH₃)—CH=CCl—CH₃ | (Z) |
| B.455 | CH(CH₃)—CBr=CH—CH₃ | (E) |
| B.456 | CH(CH₃)—CBr=CH—CH₃ | (Z) |
| B.457 | CH(CH₃)—CH=CBr—CH₃ | (E) |
| B.458 | CH(CH₃)—CH=CBr—CH₃ | (Z) |
| B.459 | CH(CH₃)—CH=CH—CH₂Cl | (E) |
| B.460 | CH(CH₃)—CH=CH—CH₂Cl | (Z) |
| B.461 | CH(CH₃)—CH=CH—CH₂CH₃ | (E) |
| B.462 | CH(CH₃)—CH=CH—CH₂CH₃ | (Z) |
| B.463 | CH(CH₃)—CH=CH—CH₂Br | (E) |
| B.464 | CH(CH₃)—CH=CH—CH₂Br | (Z) |
| B.465 | CH(CH₃)—CCl=CCl—CH₂Cl | (E) |
| B.466 | CH(CH₃)—CCl=CCl—CH₂Cl | (Z) |
| B.467 | CH(CH₃)—CF=CH₂ | |
| B.468 | CH(CH₃)—CH=CH—F | (E) |
| B.469 | CH(CH₃)—CH=CH—F | (Z) |
| B.470 | CH(CH₃)—CH=CF₂ | |
| B.471 | CH(CH₃)—CF=CH—F | (E) |
| B.472 | CH(CH₃)—CF=CH—F | (Z) |
| B.473 | CH₂CHCl—CH=CH₂ | |
| B.474 | CH₂CH₂—CH=C(CH₃)₂ | |
| B.475 | CH₂CH₂—C(CH₃)=CH—CH₃ | (E) |
| B.476 | CH₂CH₂—C(CH₃)=CH—CH₃ | (Z) |
| B.477 | C(CH₃)=CH—[C₆H₅] | (E) |
| B.478 | C(CH₃)=CH—[2-CN—C₆H₄] | (E) |
| B.479 | C(CH₃)=CH—[3-CN—C₆H₄] | (E) |
| B.480 | C(CH₃)=CH—[4-CN—C₆H₄] | (E) |
| B.481 | C(CH₃)=CH—[2-F—C₆H₄] | (E) |
| B.482 | C(CH₃)=CH—[3-F—C₆H₄] | (E) |
| B.483 | C(CH₃)=CH—[4-F—C₆H₄] | (E) |
| B.484 | C(CH₃)=CH—[2,4-F₂—C₆H₃] | (E) |
| B.485 | C(CH₃)=CH—[3,4-F₂—C₆H₃] | (E) |
| B.486 | C(CH₃)=CH—[2,4,5-F₃—C₆H₂] | (E) |
| B.487 | C(CH₃)=CH—[2,4,6-F₃—C₆H₂] | (E) |
| B.488 | C(CH₃)=CH—[2-Cl—C₆H₄] | (E) |
| B.489 | C(CH₃)=CH—[3-Cl—C₆H₄] | (E) |
| B.490 | C(CH₃)=CH—[4-Cl—C₆H₄] | (E) |
| B.491 | C(CH₃)=CH—[2,4-Cl₂—C₆H₃] | (E) |
| B.492 | C(CH₃)=CH—[3,4-Cl₂—C₆H₃] | (E) |
| B.493 | C(CH₃)=CH—[2,4,5-Cl₃—C₆H₂] | (E) |
| B.494 | C(CH₃)=CH—[2,4,6-Cl₃—C₆H₂] | (E) |
| B.495 | C(CH₃)=CH—[2-CH₃—C₆H₄] | (E) |
| B.496 | C(CH₃)=CH—[3-CH₃—C₆H₄] | (E) |
| B.497 | C(CH₃)=CH—[4-CH₃—C₆H₄] | (E) |
| B.498 | C(CH₃)=CH—[2-F, 4-CH₃—C₆H₃] | (E) |
| B.499 | C(CH₃)=CH—[2-CH₃, 4-F—C₆H₃] | (E) |
| B.500 | C(CH₃)=CH—[3-F, 4-CH₃—C₆H₃] | (E) |
| B.501 | C(CH₃)=CH—[3-CH₃, 4-F—C₆H₃] | (E) |
| B.502 | C(CH₃)=CH—[2-Cl, 4-CH₃—C₆H₃] | (E) |
| B.503 | C(CH₃)=CH—[2-CH₃, 4-Cl—C₆H₃] | (E) |
| B.504 | C(CH₃)=CH—[3-Cl, 4-CH₃—C₆H₃] | (E) |
| B.505 | C(CH₃)=CH—[3-CH₃, 4-Cl—C₆H₃] | (E) |
| B.506 | C(CH₃)=CH—[2-CF₃—C₆H₄] | (E) |
| B.507 | C(CH₃)=CH—[3-CF₃—C₆H₄] | (E) |
| B.508 | C(CH₃)=CH—[4-CF₃—C₆H₄] | (E) |
| B.509 | C(CH₃)=CH—[2-OCH₃—C₆H₄] | (E) |
| B.510 | C(CH₃)=CH—[3-OCH₃—C₆H₄] | (E) |
| B.511 | C(CH₃)=CH—[4-OCH₃—C₆H₄] | (E) |
| B.512 | C(CH₃)=CH—[2-OCHF₂—C₆H₄] | (E) |
| B.513 | C(CH₃)=CH—[3-OCHF₂—C₆H₄] | (E) |
| B.514 | C(CH₃)=CH—[4-OCHF₂—C₆H₄] | (E) |
| B.515 | CH=C(CH₃)—[C₆H₅] | (E) |
| B.516 | CH=C(CH₃)—[2-CN—C₆H₄] | (E) |
| B.517 | CH=C(CH₃)—[3-CN—C₆H₄] | (E) |
| B.518 | CH=C(CH₃)—[4-CN—C₆H₄] | (E) |
| B.519 | CH=C(CH₃)—[2-F—C₆H₄] | (E) |
| B.520 | CH=C(CH₃)—[3-F—C₆H₄] | (E) |
| B.521 | CH=C(CH₃)—[4-F—C₆H₄] | (E) |
| B.522 | CH=C(CH₃)—[2,4-F₂—C₆H₃] | (E) |
| B.523 | CH=C(CH₃)—[3,4-F₂—C₆H₃] | (E) |
| B.524 | CH=C(CH₃)—[2,4,5-F₃—C₆H₂] | (E) |
| B.525 | CH=C(CH₃)—[2,4,6-F₃—C₆H₂] | (E) |
| B.526 | CH=C(CH₃)—[2-Cl—C₆H₄] | (E) |
| B.527 | CH=C(CH₃)—[3-Cl—C₆H₄] | (E) |
| B.528 | CH=C(CH₃)—[4-Cl—C₆H₄] | (E) |
| B.529 | CH=C(CH₃)—[2,4-Cl₂—C₆H₃] | (E) |
| B.530 | CH=C(CH₃)—[3,4-Cl₂—C₆H₃] | (E) |
| B.531 | CH=C(CH₃)—[2,4,5-Cl₃—C₆H₂] | (E) |
| B.532 | CH=C(CH₃)—[2,4,6-Cl₃—C₆H₂] | (E) |
| B.533 | CH=C(CH₃)—[2-CH₃—C₆H₄] | (E) |
| B.534 | CH=C(CH₃)—[3-CH₃—C₆H₄] | (E) |
| B.535 | CH=C(CH₃)—[4-CH₃—C₆H₄] | (E) |
| B.536 | CH=C(CH₃)—[2-F, 4-CH₃—C₆H₃] | (E) |
| B.537 | CH=C(CH₃)—[2-CH₃, 4-F—C₆H₃] | (E) |
| B.538 | CH=C(CH₃)—[3-F, 4-CH₃—C₆H₃] | (E) |
| B.539 | CH=C(CH₃)—[3-CH₃, 4-F—C₆H₃] | (E) |

TABLE B-continued

| No. | R² | |
|---|---|---|
| B.540 | CH=C(CH₃)—[2-Cl, 4-CH₃—C₆H₃] | (E) |
| B.541 | CH=C(CH₃)—[2-CH₃, 4-Cl—C₆H₃] | (E) |
| B.542 | CH=C(CH₃)—[3-Cl, 4-CH₃—C₆H₃] | (E) |
| B.543 | CH=C(CH₃)—[3-CH₃, 4-Cl—C₆H₃] | (E) |
| B.544 | CH=C(CH₃)—[2-CF₃—C₆H₄] | (E) |
| B.545 | CH=C(CH₃)—[3-CF₃—C₆H₄] | (E) |
| B.546 | CH=C(CH₃)—[4-CF₃—C₆H₄] | (E) |
| B.547 | CH=C(CH₃)—[2-OCH₃—C₆H₄] | (E) |
| B.548 | CH=C(CH₃)—[3-OCH₃—C₆H₄] | (E) |
| B.549 | CH=C(CH₃)—[4-OCH₃—C₆H₄] | (E) |
| B.550 | CH=C(CH₃)—[2-OCHF₂—C₆H₄] | (E) |
| B.551 | CH=C(CH₃)—[3-OCHF₂—C₆H₄] | (E) |
| B.552 | CH=C(CH₃)—[4-OCHF₂—C₆H₄] | (E) |
| B.553 | C≡C—I | |
| B.554 | CH₂—C≡C—H | |
| B.555 | CH₂—C≡C—Cl | |
| B.556 | CH₂—C≡C—Br | |
| B.557 | CH₂—C≡C—I | |
| B.558 | CH₂—C≡C—CH₃ | |
| B.559 | CH₂—C≡C—CH₂CH₃ | |
| B.560 | CH₂CH₂—C≡C—H | |
| B.561 | CH₂CH₂—C≡C—Cl | |
| B.562 | CH₂CH₂—C≡C—Br | |
| B.563 | CH₂CH₂—C≡C—I | |
| B.564 | CH₂CH₂—C≡C—CH₃ | |
| B.565 | CH₂CH₂CH₂—C≡C—H | |
| B.566 | CH₂CH₂CH₂—C≡C—Cl | |
| B.567 | CH₂CH₂CH₂—C≡C—Br | |
| B.568 | CH₂CH₂CH₂—C≡C—I | |
| B.569 | CH₂CH₂CH₂—C≡C—CH₃ | |
| B.570 | CH(CH₃)—C≡C—H | |
| B.571 | CH(CH₃)—C≡C—Cl | |
| B.572 | CH(CH₃)—C≡C—Br | |
| B.573 | CH(CH₃)—C≡C—I | |
| B.574 | CH(CH₃)—C≡C—CH₃ | |
| B.575 | C≡C—[4-F—C₆H₄] | |

The compounds I are suitable as fungicides. They are distinguished by an outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,
Botrytis cinerea (gray mold) on strawberries, vegetables, ornamentals and grapevines,
Cercospora arachidicola on peanuts,
Erysiphe cichoracearum and Sphaerotheca fuliginea on cucurbits,
Erysiphe graminis (powdery mildew) on cereals,
Fusarium and Verticillium species on various plants,
Helminthosporium species on cereals,
Mycosphaerella species on bananas,
Phytophthora infestans on potatoes and tomatoes,
Plasmopara viticola on grapevines,
Podosphaera leucotricha on apples,
Pseudocercosporella herpotrichoides on wheat and barley,
Pseudocercosporella species on hops and cucumbers,
Puccinia species on cereals,
Pyricularia oryzae on rice,
Rhizoctonia species on cotton, rice and lawns,
Septoria nodorum on wheat,
Uncinula necator on grapevines,
Ustilago species on cereals and sugar cane, and
Venturia inaequalis (scab) on apples.

Moreover, the compounds I are suitable for controlling harmful fungi in the protection of materials (eg. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

Moreover, the compounds of the formula I are suitable for efficiently controlling animal pests from the classes of the insects, arachnids and nematodes. They can be employed in crop protection and in the hygiene, stored-product and veterinary sector for controlling animal pests. In particular, they are suitable for controlling the following animal pests: insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria*, dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*, thrips (Thysanoptera), eg. *Frankliniella fusca, Frankliniella occidentalis, Frankliniella tritici, Scirtothrips citri, Thrips oryzae, Thrips palmi* and *Thrips tabaci*, hymenopterans (Hymenoptera), eg. *Athalia rosae, Atta cephalotes, Atta sexdens, Atta texana, Hoplocampa minuta, Hoplocampa testudinea, Monomorium pharaonis, Solenopsis geminata* and *Solenopsis invicta*, heteropterans (Heteroptera), eg. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterans (Homoptera), eg. *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* termites (Isoptera), eg. *Calotermes flavicollis, Leucotermes flavipes, Reticulitermes lucifugus* und *Termes natalensis,* orthopterans (Orthoptera), eg. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,*

Arachnoidea, such as arachnids (Acarina), eg. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root knot nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The rate of application of active ingredient for controlling animal pests is from 0.1 to 2.0, preferably 0.2 to 1.0, kg/ha under field conditions.

The compounds I can be converted into the customary formulations, eg. solutions, emulsions, suspensions, dusts, powders, pastes and granules. The use form depends on the particular purpose; in any case, it should guarantee a fine and uniform distribution of the compound according to the invention.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These auxiliaries and agents can be admixed with the active ingredients according to the invention in a weight ratio of 1:10 to 10:1.

In the use form as fungicides, the compositions according to the invention can also be present together with other active ingredients, eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N'-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)phosphinyl]-3-phenyl-1,2,4-triazole, 2,3-dicyano-1,4-dithioanthraquinone, 2-thio-1,3-dithiolo [4,5-b]quinoxaline, methyl 1-(butylcarbamoyl)-2-benzimidazolecarbamate, 2-methoxycarbonylaminobenzimidazole, 2-(2-furyl)-benzimidazole, 2-(4-thiazolyl)-benzimidazole, N-(1,1,2,2-tetrachloroethylthio)tetrahydrophthalimide, N-trichloromethylthio-tetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichlorethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins such as methyl E-methoxyimino-[α-(o-tolyloxy)-o-tolyl]acetate, methyl E-2-{2-[6-(2-cyanophenoxy)pyrimidin-4-yloxy]-phenyl}-3-methoxyacrylate, N-methyl-E-methoxyimino-[α-(2-phenoxyphenyl)]-acetamide, N-methyl-E-methoxyimino-[α-(2,5-dimethylphenoxy)-o-tolyl]acetamide, anilinopyrimidines such as N-(4,6-dimethylpyrimidin-2-yl) aniline, N-[4-methyl-6-(1-propynyl)pyrimidin-2-yl]-aniline, N-[4-methyl-6-cyclopropylpyrimidin-2-yl] aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)methyl)-1H-1,2,4-triazole.

MODE(S) FOR CARRYINIG OUT THE INVENTION

SYNTHESIS EXAMPLES

With due modification of the starting compounds, the protocols shown in the synthesis examples below were used for obtaining further compounds I. The resulting compounds, together with physical data, are listed in the Tables which follow.

EXAMPLE 1

Preparation of

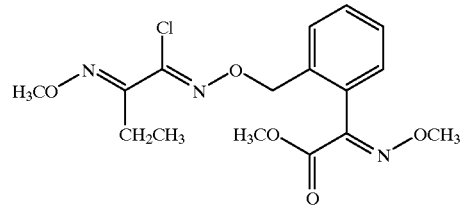

Stage 1:

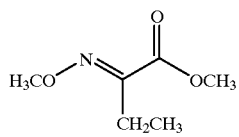

A solution of 50 g (0.49 mol) of 2-oxobutanoic acid in 300 ml of methanol was treated with 123 g (1.47 mol) of methoxyamine hydrochloride, a little at a time. After the reaction mixture had been stirred for 16 hours at room temperature (approximately 25° C.), it was freed from solvent under reduced pressure. The resulting residue was taken up in water and tert-butyl methyl ether. The ether phase was washed with saturated $NaHCO_3$ solution and with water, dried over $Na_2SO_4$ and subsequently concentrated under reduced pressure. This gave 47 g of the title compound as a colorless liquid.

$^1$H NMR ($CDCl_3$; δ in ppm): 1.06 (t, 3H); 2.57 (q, 2H); 3.85 (s, 3H); 4.04 (s, 3H)

Stage 2:

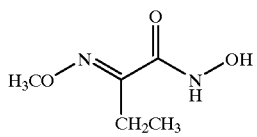

46 g (0.32 mol) of the compound of Example 1, Stage 1, were added dropwise at 10° C. to a solution of 33 g (0.48 mol) of hydroxylamine hydrochloride and 400 ml of methanol. 171 g of sodium methoxide solution (30% strength in methanol, 0.96 mol) were subsequently added to the resulting mixture in the course of 15 minutes with ice-cooling. The reaction mixture was then stirred for 60 hours at room temperature (approximately 25° C.), during which process a suspension formed. The suspension was poured into water; the resulting mixture was acidified with concentrated hydrochloric acid, with ice-cooling, until it had reached a pH of 6.5 and subsequently extracted repeatedly with methylene chloride. The organic phases were combined, washed with water, dried over $Na_2SO_4$ and freed from solvent under reduced pressure at 30° C. This gave 34.1 g of the title compound as a white powder; m.p.: 56–59° C.

ATTENTION: Hydroxamic acids of the type of the compound as given in Example 1., Stage 2, may be thermolabile and decompose explosively at higher temperatures!

$^1$H NMR ($CDCl_3$; δ in ppm): 1.03 (t, 3H); 2.53 (q, 2H); 3.93 (s, 3H); 8.95 (s, br, 2H)

Stage 3:

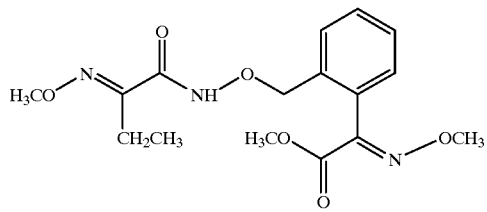

38.6 g of sodium methoxide solution (30% strength in methanol; 0.215 mol) were added dropwise with ice-cooling to a solution of 28.5 g (0.195 mol) of the compound of Example 1, Stage 2, 55.8 g (0.195 mol) of methyl E-2-methoxyimino-2-[2'-bromomethylphenyl]acetate (in accordance with EP-A 400 417) and 600 ml of N,N-dimethylformamide. After the reaction mixture had been stirred for 16 hours at room temperature (approximately 25° C.), it was stirred into cooled dilute hydrochloric acid, and the resulting mixture was extracted with tert-butyl methyl ether. The organic phase was washed with water, dried over $Na_2SO_4$ and freed from solvent under reduced pressure at approximately 35° C. The residue obtained was purified by chromatography (silica gel; eluent: tert-butyl methyl ether/cyclohexane). After the solid isolated had been washed with pentane, 50 g of the title compound were obtained as a pale yellow powder; m.p.: 63–65° C.

$^1$H NMR ($CDCl_3$; δ in ppm): 1.03 (t, 3H); 2.51 (q, 2H); 3.87 (s, 6H); 4.03 (s, 3H); 4.86 (s, 2H); 7.14–7.45 (m, 4H); 8.92 (s, 1H)

Stage 4:

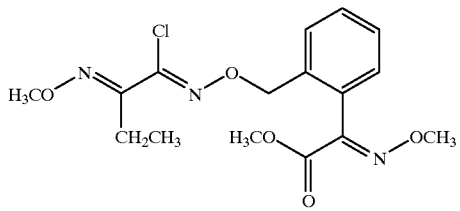

A mixture of 6.0 g (17.1 mmol) of the compound of Example 1, Stage 3, 22.4 g (85.5 mmol) of triphenylphosphine and 250 ml of acetonitrile was treated with 13.2 g (85.5 mmol) of tetrachloromethane, a little at a time. The resulting reaction mixture was refluxed for 60 hours and subsequently cooled to room temperature (approximately 25° C.). The solvent was distilled off under reduced pressure, and the residue which remained was purified by chromatography (silica gel, tert-butyl methyl ether/cyclohexane). This gave 2.3 g of the title compound as a beige powder; m.p.: 56–59° C.

$^1$H NMR ($CDCl_3$; δ in ppm): 0.97 (t, 3H); 2.55 (q, 2H); 3.85 (s, 3H); 3.99 (s, 3H); 4.04 (s, 3H); 5.13 (s, 2H); 7.15–7.50 (m, 4H)

EXAMPLE 2

Preparation of

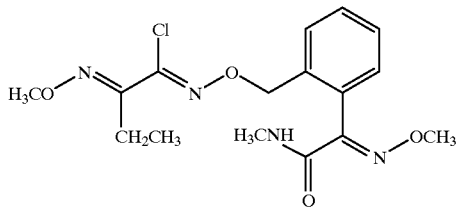

A solution of 15.5 g (42 mmol) of the compound of Example 1, Stage 4, and 100 ml of tetrahydrofuran was treated with 33 g of methylamine solution (40% strength in water). After 2 hours at room temperature (approximately 25° C.), the reaction mixture was poured into cooled dilute hydrochloric acid. The acidic solution was extracted with tert-butyl methyl ether. The organic phase was subsequently washed with water, dried over $Na_2SO_4$ and freed from solvent under reduced pressure. After the residue had been triturated with hexane/tert-butyl methyl ether, 11.5 g of the title compound were obtained as a beige powder; m.p.: 66–69° C.

¹H NMR (CDCl₃; δ in ppm): 0.97 (t, 3H); 2.54 (q, 2H); 2.85 (d, 3H); 3.91 (s, 3H); 3.97 (s, 3H); 5.15 (s, 2H); 6.80 (s, br, 1H); 7.18–7.43 (m, 4H)

EXAMPLE 3

Preparation of

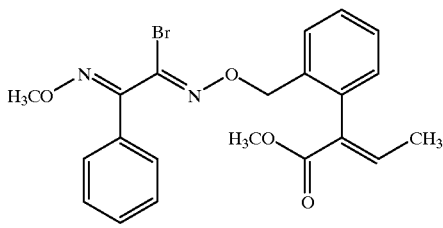

Stage 1:

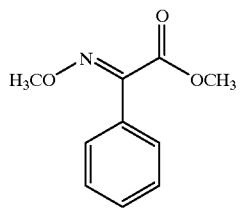

A solution of 388 g (4.65 mol) of methoxyamine hydrochloride and 1.5 l of methanol was first treated with 60 g of molecular sieve (3 Å) and subsequently, at 60° C., with 254 g (1.55 mol) of methyl phenylglyoxylate. After 6 hours at 60° C. and a further 60 hours at room temperature (approximately 25° C.), the reaction mixture was treated with water. The aqueous solution was extracted with tert-butyl methyl ether. The ether phase was washed with water, dried over Na₂SO₄ and freed from solvent under reduced pressure. The residue was purified by chromatography (silica gel; tert-butyl methyl ether/cyclohexane). This gave 66 g of the title compound as a pale yellow powder.

¹H NMR (CDCl₃; δ in ppm): 3.88 (s, 3H); 4.07 (s, 3H); 7.40 (s, 5H)

Stage 2:

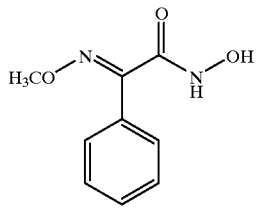

A solution of 36.1 g (0.52 mol) of hydroxylamine hydrochloride in 250 ml of methanol was added dropwise to a solution of 58.2 g (1.04 mol) of potassium hydroxide in 750 ml of methanol. After approximately 10 minutes, the precipitate formed was filtered off, and the resulting solution was treated with a solution of 100 g of the compound of Example 3, Stage 1, in 500 ml of methanol. After 24 hours at room temperature (approximately 25° C.), the reaction mixture was poured into water and extracted with tert-butyl methyl ether. The aqueous phase was acidified with dilute hydrochloric acid, with ice-cooling, to a pH of 6.5, during which process a precipitate formed. The precipitate was isolated and dried under reduced pressure. This gave 57 g of the title compound as a beige powder; m.p.: 142–144° C.

¹H NMR (d₆-DMSO; δ in ppm): 3.89 (s, 3H); 7.33–7.55 (m, 5H); 9.20 (s, br, 1H); 11.14 (s, br, 1H)

Stage 3:

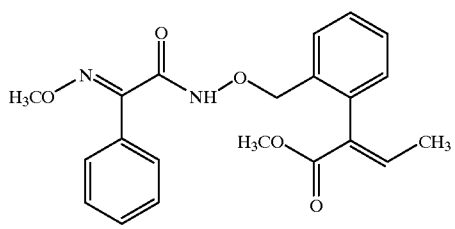

18 g of sodium methoxide solution (30% in methanol; 0.1 mol) was added dropwise with ice-cooling to a solution of 20 g (0.1 mol) of the compound of Example 3, Stage 2, 27 g (0.1 mol) of methyl E-3-methyl-2-[2'-bromomethylphenyl]acrylate (as described in EP-A 513 580) and 300 ml of N,N-dimethylformamide. After the reaction mixture had been stirred for 12 hours at room temperature (approximately 25° C.), it was stirred into ice-water and the resulting mixture was extracted with methylene chloride. The organic phase was washed with water, dried over Na₂SO₄ and freed from solvent under reduced pressure at approximately 35° C.

The residue obtained was crystallized from tert-butyl methyl ether/hexane/isopropanol. This gave 23.8 g of the title compound as colorless crystals; m.p.: 81–84° C.

¹H NMR (CDCl₃; δ in ppm): 1.63 (d, 3H); 3.70 (s, 3H); 3.92 (s, 3H); 4.83–4.92 (m, 2H); 7.08–7.53 (m, 10H); 9.07 (s, br, 1H)

Stage 4:

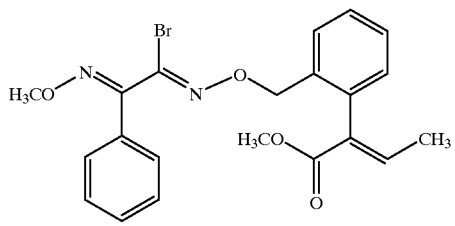

A mixture of 4.8 g (12.6 mmol) of the compound of Example 3, Stage 3, 10 g (38 mmol) of triphenylphosphine and 100 ml of acetonitrile was treated with 12.6 g (38 mmol) of tetrabromomethane, a little at a time. The resulting reaction mixture was refluxed for 100 hours and subsequently cooled to room temperature (approximately 25° C.). The solvent was distilled off under reduced pressure, and the residue which remained was purified by chromatography (silica gel, tert-butyl methyl ether/cyclohexane). This gave 2.4 g of the title compound as a colorless powder; m.p.: 60–61° C.

¹H NMR (CDCl₃; δ in ppm): 1.54 (d, 3H); 3.66 (s, 3H); 3.99 (s, 3H); 5.02 (s, 2H), 7.01–7.38 (m, 10H)

TABLE I

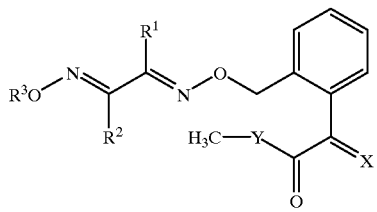

(I)

| No. | X | Y | | R¹ | R² | R³ | Physical data |
|---|---|---|---|---|---|---|---|
| I.1 | NOCH$_3$ | (E) | NH | Cl | C$_6$H$_5$ | CH$_3$ | IR (KBr): 3450, 2950, 1668, 1519, 1445, 1041, 1001, 980, 950, 930, 813, 699 cm$^{-1}$ |
| I.2 | CHCH$_3$ | (E) | O | Br | C$_6$H$_5$ | CH$_3$ | m.p.: 60–61° C. |
| I.3 | NOCH$_3$ | (E) | NH | Cl | CH$_2$CH$_3$ | CH$_3$ | m.p.: 66–69° C. |
| I.4 | NOCH$_3$ | (E) | O | Cl | CH$_2$CH$_3$ | CH$_3$ | m.p.: 56–59° C. |
| I.5 | NOCH$_3$ | (E) | O | Cl | CH$_2$CH$_3$ | CH$_2$CH$_3$ | m.p.: 81–84° C. |
| I.6 | NOCH$_3$ | (E) | NH | Br | CH$_2$CH$_3$ | CH$_2$CH$_3$ | m.p.: 68–70° C. |
| I.7 | NOCH$_3$ | (E) | NH | Cl | CH$_2$CH$_3$ | CH$_2$CH$_3$ | m.p.: 48–50° C. |
| I.8 | NOCH$_3$ | (E) | O | Br | CH$_2$CH$_3$ | CH$_2$CH$_3$ | m.p.: 42–45° C. |
| I.9 | NOCH$_3$ | (E) | O | Cl | 4-Cl—C$_6$H$_4$ | CH$_3$ | m.p.: 110–114° C. |
| I.10 | NOCH$_3$ | (E) | NH | Cl | 4-Cl—C$_6$H$_4$ | CH$_3$ | m.p.: 114–117° C. |
| I.11 | CHCH$_3$ | (E) | O | Cl | 4-Cl—C$_6$H$_4$ | CH$_3$ | IR(film): 1716, 1490, 1254, 1047, 1019, 1009, 956, 943, 808, 765 cm$^{-1}$ |
| I.12 | NOCH$_3$ | (E) | O | Cl | 4-F—C$_6$H$_4$ | CH$_3$ | m.p.: 111–113° C. |
| I.13 | NOCH$_3$ | (E) | NH | Cl | 4-F—C$_6$H$_4$ | CH$_3$ | m.p.: 121–124° C. |

| No. | X | Y | | R¹ | R² | R³ | Physical data |
|---|---|---|---|---|---|---|---|
| I.14 | CHCH$_3$ | (E) | O | Cl | 4-F—C$_6$H$_4$ | CH$_3$ | m.p.: 52–55° C. |
| I.15 | CH(OCH$_3$) | (E) | O | Cl | CH$_2$CH$_3$ | CH$_3$ | m.p.: 75–80° C. |
| I.16 | CHCH$_3$ | (E) | O | Cl | CH$_2$CH$_3$ | CH$_3$ | IR(film): 1718, 1435, 1254, 1208, 1048, 1037, 1001, 946, 849, 762 cm$^{-1}$ |
| I.17 | NOCH$_3$ | (E) | O | Cl | CH$_2$CH$_2$CH$_3$ | CH$_3$ | IR(film): 2940, 1728, 1438, 1320, 1306, 1221, 1070, 1048, 1020, 967 cm$^{-1}$ |
| I.18 | NOCH$_3$ | (E) | O | Cl | CH$_3$CHCH$_3$ | CH$_3$ | m.p.: 98–101° C. |
| I.19 | CH(OCH$_3$) | (E) | O | Cl | 4-Cl—C$_6$H$_4$ | propargyl | IR(film): 3280, 2940, 1708, 1634, 1491, 1286, 1257, 1131, 1112, 1092, 1004, 939 cm$^{-1}$ |
| I.20 | NOCH$_3$ | (E) | O | Cl | CH$_3$CHCH$_2$CH$_3$ | CH$_3$ | IR(film): 2925, 2853, 1729, 1461, 1220, 1069, 1047, 1018, 969, 952 cm$^{-1}$ |
| I.21 | NOCH$_3$ | (E) | NH | Cl | CH$_3$CHCH$_2$CH$_3$ | CH$_3$ | IR(film): 2959, 2925, 2872, 2854, 1672 1526, 1462, 1042, 1008, 979 cm$^{-1}$ |
| I.22 | NOCH$_3$ | (E) | NH | Cl | CH$_2$CH$_2$CH$_3$ | CH$_3$ | m.p.: 78–81° C. |

Examples for the Action Against Harmful Fungi

The improved fungicidal action of the compounds of the general formula I was demonstrated by the following experiments. The known active ingredients A.1 and A.2 were used as comparison compounds of the prior art in accordance with WO-A 95/21,153 and WO-A 95/21,154.

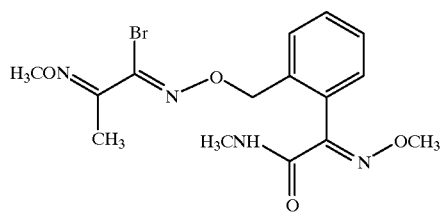

(A.1)

-continued

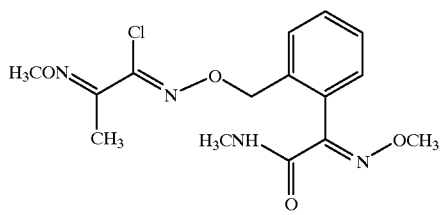

(A.2)

The active ingredients were formulated separately as a 10% emulsion in a mixture of 63% by weight of cyclohexanone and 27% by weight of emulsifier and diluted with water to give the desired concentration.

Activity Against Puccinia recondita on Wheat (Leaf Rust of Wheat)

Leaves of wheat seedlings "Fruhgold" in pots were dusted with leaf rust spores (Puccinia recondita). The pots were then placed for 24 hours into a chamber with high atmospheric humidity (90 to 95%) at 20 to 22° C. During this time, the spores germinated, and the germinal tubes penetrated the leaf tissue. The next day, the infected plants were sprayed to run-off with an aqueous preparation of the active ingredient. After the spray coating had dried on, the test plants were grown for 7 days in a greenhouse at from 20 to 22° C. and a relative atmospheric humidity of 65 to 70%. The extent of rust development on the leaves was then determined.

In this test, the plants which had been treated with 16 ppm of the compounds I.3, I.6, I.7, I.10 to I.17, I.21 and I.22 according to the invention showed no disease or a disease level of not more than 5%, while the disease level of the plants which had been treated with the same amount of the comparison compounds A.1 and A.2 was 15 and 80%, respectively. The disease level of the untreated (control) plants was 80%.

In a similar test, the plants which had been treated with 4 ppm of the compounds I.3, I.6, I.7, I.10 to I.17, I.21 and I.22 according to the invention showed a disease level of 5 to 40%, while the disease level of the comparison compounds A.1 and A.2 was 60 and 80%, respectively. The disease level of the untreated (control) plants was 80%.

Activity Against Pyricularia oryzae (Protective)

Leaves of rice seedlings cv. "Tai-Nong 67" in pots were sprayed to run-off with an aqueous preparation of the active ingredient. The next day, the plants were infected with an aqueous spore suspension of Pyricularia oryzae. The test plants were subsequently placed for 6 days into controlled-environment cabinets at 22–24° C. and a relative atmospheric humidity of 95–99%. The extent of the disease development on the leaves was then determined visually.

In this test, the plants which had been treated with 250 ppm of the compounds I.1, I.2, I.3, I.4, I.5, I.6, I.7, I.8, I.10, I.11, I.14 to I.17 and I.20 to I.22 according to the invention showed a disease level of not more than 15%, while the disease level of the plants which had been treated with the same amount of the comparison compounds A.1 and A.2 was 80 and 25%, respectively. The disease level of the untreated (control) plants was 80%.

Examples of the Action Against Animal Pests

The improved action of the compounds of the formula I against animal pests was demonstrated by the following experiments.

The active ingredients were formulated
a. as a 0.1% strength solution in acetone or
b. as a 10% strength emulsion in a mixture of 70% by weight of cyclohexanone, 20% by weight of Nekanil® LN (Lutensol® AP6, wetter with emulsifying and dispersant action based on ethoxylated alkylphenols) and 10% by weight of Wettol® EM (non-ionic emulsifier based on ethoxylated castor oil)

and the formulations were diluted to give the desired concentration, using acetone in the case of a. or water in the case of b.

After the experiments had been concluded, in each case the lowest concentration was determined at which the compounds still caused an 80 to 100% inhibition or mortality in comparison with untreated controls (limit or minimal concentration).

We claim:

1. A hydroximic acid halide compound I

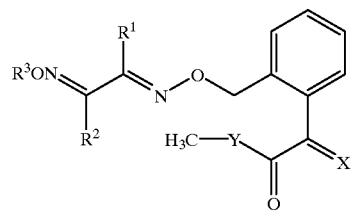

(I)

wherein the substituents have the following meanings:
X is $NOCH_3$, $CHOCH_3$ or $CHCH_3$;
Y is O or NH;
$R^1$ is halogen;
$R^2$ is
  $C_2$–$C_6$-alkyl, $C_2$–$C_6$-alkenyl and $C_2$–$C_6$-alkynyl, it being possible for these groups to be partially or fully halogenated and/or to have attached to them one or two of the following radicals: cyano, $C_1$–$C_4$-alkoxy, $C_1$–$C_4$-haloalkoxy and phenyl, it being possible for the phenyl, in turn, to be partially or fully halogenated and/or to have attached to it one to three of the following groups: cyano, nitro, $C_1$–$C_4$-alkyl, $C_1$–$C_4$-haloalkyl, $C_1$–$C_4$-alkoxy and $C_1$–$C_4$-haloalkoxy;
  methyl which is partially or fully halogenated and/or has attached to it one of the following radicals: cyano, $C_1$–$C_4$-alkoxy or $C_1$–$C_4$-haloalkoxy;
  $C_5$–$C_6$-cycloalkyl which can be partially or fully halogenated and/or can have attached to it one to three $C_1$–$C_4$-alkyl groups;
  aryl or arylmethylene which can be partially or fully halogenated in the aryl moiety and/or can have attached to it one to three of the following radicals: cyano, nitro, $C_1$–$C_4$-alkyl, $C_1$–$C_4$-haloalkyl, $C_1$–$C_4$-alkoxy and $C_1$–$C_4$-haloalkoxy;
$R^3$ is $C_1$–$C_6$-alkyl, $C_1$–$C_3$-alkoxy-$C_1$–$C_6$-alkyl, $C_3$–$C_6$-cycloalkyl-$C_1$–$C_6$-alkyl, $C_3$–$C_6$-alkenyl and $C_3$–$C_6$-alkynyl, it being possible for these groups to be partially or fully halogenated and it being possible for the cycloalkyl groups additionally to have attached to them one to three $C_1$–$C_4$-alkyl radicals, or a salt thereof.

2. A process for the preparation of the compound I defined in claim 1, which comprises first converting a carboxylic ester IIa (IIa)

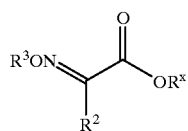

wherein R$^x$ is C$_1$–C$_6$-alkyl or phenyl, with hydroxylamine to give the corresponding hydroxamic acid IIc (IIc)

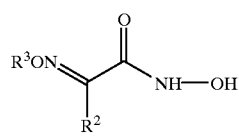

subsequently reacting IIc with a benzyl compound IIIa (IIIa)

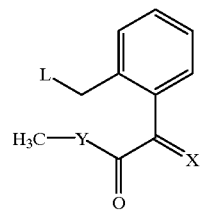

wherein L is a nucleofugic leaving group, to give a hydroxamic ester compound IV (IV)

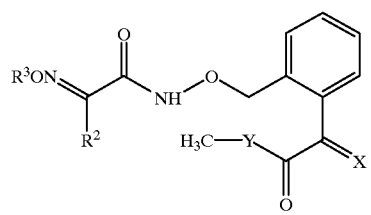

and converting IV with a halogenating agent to give the compound I.

3. A process for the preparation of the compound IV set forth in claim 2, which comprises reacting a carboxylic acid IIb (IIb)

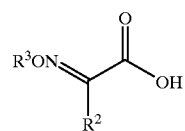

with a benzylhydroxylamine IIIb (IIIb)

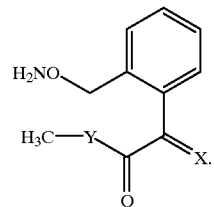

4. A process for the preparation of the compound I defined in claim 1, which comprises converting an amidoxime IId (IId)

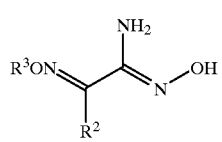

with a benzyl compound IIIa (IIIa)

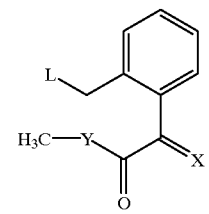

to give a compound V (V)

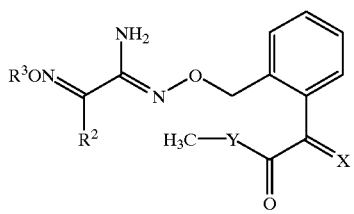

and exchanging the amino group of V for halogen via a diazotization reaction.

5. A composition which is suitable for controlling animal pests or harmful fungi, comprising a solid or liquid carrier and the compound I defined in claim 1.

6. A method of controlling harmful fungi, which comprises treating the fungi, or the materials, plants, soil or seeds to be protected against fungal infection with an effective amount of the compound I defined in claim 1.

7. A method of controlling animal pests, which comprises treating the pests or the materials, plants, soil or seeds to be protected against the animal pests with an effective amount of the compound I defined in claim 1.

8. The compound I defined in claim 1, wherein X is NOCH$_3$, Y is NH, R$^1$ is chlorine and R$^3$ is C$_1$–C$_3$-alkyl.

9. The compound I defined in claim 1, wherein R$^2$ is C$_2$–C$_6$-alkyl.

10. The compound I defined in claim 1, wherein R$^2$ is phenyl which is unsubstituted, or is partially halogenated and/or carries one to three radicals selected from the group consisting of cyano, $C_1$–$C_4$-alkyl, $C_1$–$C_4$-haloalkyl, $C_1$–$C_4$-alkoxy and $C_1$–$C_4$-haloalkoxy, or which phenyl is fully halogenated.

11. The compound I defined in claim 8, wherein $R^2$ is $C_2$–$C_6$-alkyl.

12. The compound I defined in claim 8, wherein $R^2$ is phenyl which is unsubstituted, or is partially halogenated and/or carries one to three radicals selected from the group consisting of cyano, $C_1$–$C_4$-alkyl, $C_1$–$C_4$-haloalkyl, $C_1$–$C_4$-alkoxy and $C_1$–$C_4$-haloalkoxy, or which phenyl is fully halogenated.

* * * * *